United States Patent
Vidlund et al.

(10) Patent No.: US 8,070,805 B2
(45) Date of Patent: *Dec. 6, 2011

(54) DEVICES AND METHODS FOR HEART VALVE TREATMENT

(75) Inventors: Robert M. Vidlund, Maplewood, MN (US); Jason E. Kalgreen, Plymouth, MN (US); Todd J. Mortier, Minneapolis, MN (US); Cyril J. Schweich, Jr., Mapple Grove, MN (US); Richard Schroeder, Fridley, MN (US); David Kusz, Minneapolis, MN (US)

(73) Assignee: Edwards Lifesciences LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/693,002

(22) Filed: Jan. 25, 2010

(65) Prior Publication Data

US 2010/0185276 A1    Jul. 22, 2010

Related U.S. Application Data

(63) Continuation of application No. 11/171,677, filed on Jul. 1, 2005, now Pat. No. 7,678,145, which is a continuation of application No. 10/866,990, filed on Jun. 15, 2004, now Pat. No. 7,077,862, which is a continuation of application No. 10/040,784, filed on Jan. 9, 2002, now Pat. No. 6,764,510.

(51) Int. Cl.
*A61F 2/24* (2006.01)

(52) U.S. Cl. ........................................ 623/2.36

(58) Field of Classification Search ........... 623/2.1–2.37
See application file for complete search history.

(56) References Cited

U.S. PATENT DOCUMENTS

| 963,899 A | 7/1910 | Kistler |
|---|---|---|
| 3,019,790 A | 2/1962 | Militana |
| 3,656,185 A | 4/1972 | Carpentier |
| 3,980,086 A | 9/1976 | Kletschka et al. |
| 4,035,849 A | 7/1977 | Angell et al. |
| 4,055,861 A | 11/1977 | Carpentier et al. |
| 4,192,293 A | 3/1980 | Asrican |
| 4,217,665 A | 8/1980 | Bex et al. |
| 4,261,342 A | 4/1981 | Aranguren Duo |
| 4,281,659 A | 8/1981 | Farrar et al. |
| 4,300,564 A | 11/1981 | Furihata |

(Continued)

FOREIGN PATENT DOCUMENTS

DE    32 27 984 A1    2/1984

(Continued)

OTHER PUBLICATIONS

Carpentier et al., "Myocardial Substitution with a Stimulated Skeletal Muscle: First Successful Clinical Case," Letter to the Editor, p. 1267, Sep. 25, 1996.

(Continued)

*Primary Examiner* — Suzette J Gherbi
(74) *Attorney, Agent, or Firm* — Melinda Michalerya

(57) ABSTRACT

Devices and methods for treating heart valves include members that assist the valve in closing during at least a portion of the cardiac cycle. Such devices include members configured to alter the shape of a valve annulus, reposition at least one papillary muscle, and/or plug an orifice of the valve so as to provide a coaptation surface for the valve leaflets.

24 Claims, 39 Drawing Sheets

U.S. PATENT DOCUMENTS

| | | | |
|---|---|---|---|
| 4,306,319 A | 12/1981 | Kaster | |
| 4,343,048 A | 8/1982 | Ross et al. | |
| 4,372,293 A | 2/1983 | Vijil-Rosales | |
| 4,409,974 A | 10/1983 | Freedland | |
| 4,536,893 A | 8/1985 | Parravicini | |
| 4,548,203 A | 10/1985 | Tacker, Jr. et al. | |
| 4,554,929 A | 11/1985 | Samson et al. | |
| 4,579,120 A | 4/1986 | MacGregor | |
| 4,592,342 A | 6/1986 | Salmasian | |
| 4,629,459 A | 12/1986 | Ionescu et al. | |
| 4,632,101 A | 12/1986 | Freedland | |
| 4,690,134 A | 9/1987 | Snyders | |
| 4,705,040 A | 11/1987 | Mueller et al. | |
| 4,936,857 A | 6/1990 | Kulik | |
| 4,944,753 A | 7/1990 | Burgess et al. | |
| 4,960,424 A | 10/1990 | Grooters | |
| 4,991,578 A | 2/1991 | Cohen | |
| 4,997,431 A | 3/1991 | Isner et al. | |
| 5,061,277 A | 10/1991 | Carpentier et al. | |
| 5,104,407 A | 4/1992 | Lam et al. | |
| 5,106,386 A | 4/1992 | Isner et al. | |
| 5,131,905 A | 7/1992 | Grooters | |
| RE34,021 E | 8/1992 | Mueller et al. | |
| 5,152,765 A | 10/1992 | Ross et al. | |
| 5,156,621 A | 10/1992 | Navia et al. | |
| 5,169,381 A | 12/1992 | Snyders | |
| 5,192,314 A | 3/1993 | Daskalakis | |
| 5,250,049 A | 10/1993 | Michael | |
| 5,256,132 A | 10/1993 | Snyders | |
| 5,258,015 A | 11/1993 | Li et al. | |
| 5,284,488 A | 2/1994 | Sideris | |
| 5,300,087 A | 4/1994 | Knoepfler | |
| 5,312,642 A | 5/1994 | Chesterfield et al. | |
| 5,350,399 A | 9/1994 | Erlebacher et al. | |
| 5,360,444 A | 11/1994 | Kusuhara | |
| 5,376,112 A | 12/1994 | Duren | |
| 5,383,840 A | 1/1995 | Heilman et al. | |
| 5,385,528 A | 1/1995 | Wilk | |
| 5,389,096 A | 2/1995 | Aita et al. | |
| 5,397,331 A | 3/1995 | Himpens et al. | |
| 5,417,709 A | 5/1995 | Slater | |
| 5,433,727 A | 7/1995 | Sideris | |
| 5,445,600 A | 8/1995 | Abdulla | |
| 5,450,860 A | 9/1995 | O'Connor | |
| 5,452,733 A | 9/1995 | Sterman et al. | |
| 5,458,574 A | 10/1995 | Machold et al. | |
| 5,496,305 A | 3/1996 | Kittrell et al. | |
| 5,509,428 A | 4/1996 | Dunlop | |
| 5,522,884 A | 6/1996 | Wright | |
| 5,533,958 A | 7/1996 | Wilk | |
| 5,571,215 A | 11/1996 | Sterman et al. | |
| 5,584,803 A | 12/1996 | Stevens et al. | |
| 5,593,424 A | 1/1997 | Northrup, III | |
| 5,607,471 A | 3/1997 | Seguin et al. | |
| 5,655,548 A | 8/1997 | Nelson et al. | |
| 5,665,092 A | 9/1997 | Mangiardi et al. | |
| 5,674,279 A | 10/1997 | Wright et al. | |
| 5,682,906 A | 11/1997 | Sterman et al. | |
| 5,683,364 A | 11/1997 | Zadini et al. | |
| 5,702,343 A | 12/1997 | Alferness | |
| 5,713,954 A | 2/1998 | Rosenberg et al. | |
| 5,718,725 A | 2/1998 | Sterman et al. | |
| 5,738,649 A | 4/1998 | Macoviak | |
| 5,749,839 A | 5/1998 | Kovacs | |
| 5,755,783 A | 5/1998 | Stobie et al. | |
| 5,758,663 A | 6/1998 | Wilk et al. | |
| 5,766,234 A | 6/1998 | Chen et al. | |
| 5,776,189 A | 7/1998 | Khalid et al. | |
| 5,792,179 A | 8/1998 | Sideris | |
| 5,800,334 A | 9/1998 | Wilk | |
| 5,800,528 A | 9/1998 | Lederman et al. | |
| 5,800,531 A | 9/1998 | Cosgrove et al. | |
| 5,807,384 A | 9/1998 | Mueller | |
| 5,814,097 A | 9/1998 | Sterman et al. | |
| 5,824,066 A | 10/1998 | Gross | |
| 5,824,069 A | 10/1998 | Lemole | |
| 5,840,059 A | 11/1998 | March et al. | |
| 5,849,005 A | 12/1998 | Garrison et al. | |
| 5,855,601 A | 1/1999 | Bessler et al. | |
| 5,855,614 A | 1/1999 | Stevens et al. | |
| 5,865,791 A | 2/1999 | Whayne et al. | |
| 5,876,436 A | 3/1999 | Vanney et al. | |
| 5,888,240 A | 3/1999 | Carpentier et al. | |
| 5,902,229 A | 5/1999 | Tsitlik et al. | |
| 5,928,281 A | 7/1999 | Huynh et al. | |
| 5,944,738 A | 8/1999 | Amplatz et al. | |
| 5,957,977 A | 9/1999 | Melvin | |
| 5,961,440 A | 10/1999 | Schweich, Jr. et al. | |
| 5,961,539 A | 10/1999 | Northrup, III et al. | |
| 5,961,549 A | 10/1999 | Nguyen et al. | |
| 5,967,990 A | 10/1999 | Thierman et al. | |
| 5,971,910 A | 10/1999 | Tsitlik et al. | |
| 5,971,911 A | 10/1999 | Wilk | |
| 5,972,022 A | 10/1999 | Huxel | |
| 5,972,030 A | 10/1999 | Garrison et al. | |
| 5,984,857 A | 11/1999 | Buck et al. | |
| 5,984,917 A | 11/1999 | Fleischman et al. | |
| 5,999,678 A | 12/1999 | Murphy-Chutorian et al. | |
| 6,001,126 A | 12/1999 | Nguyen-Thien-Nhon | |
| 6,019,722 A | 2/2000 | Spence et al. | |
| 6,024,096 A | 2/2000 | Buckberg | |
| 6,024,756 A | 2/2000 | Huebsch et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,071,303 A | 6/2000 | Laufer | |
| 6,077,214 A | 6/2000 | Mortier et al. | |
| 6,077,218 A | 6/2000 | Alferness | |
| 6,079,414 A | 6/2000 | Roth | |
| 6,085,754 A | 7/2000 | Alferness et al. | |
| 6,086,532 A | 7/2000 | Panescu et al. | |
| 6,090,096 A | 7/2000 | St. Goar et al. | |
| 6,095,968 A | 8/2000 | Snyders | |
| 6,102,944 A | 8/2000 | Huynh et al. | |
| 6,110,100 A | 8/2000 | Talpade | |
| 6,113,536 A | 9/2000 | Aboul-Hosn et al. | |
| 6,117,159 A | 9/2000 | Huebsch et al. | |
| 6,120,520 A | 9/2000 | Saadat et al. | |
| 6,123,662 A | 9/2000 | Alferness et al. | |
| 6,125,852 A | 10/2000 | Stevens et al. | |
| 6,126,590 A | 10/2000 | Alferness | |
| 6,129,758 A | 10/2000 | Love | |
| 6,132,438 A | 10/2000 | Fleischman et al. | |
| 6,143,025 A | 11/2000 | Stobie et al. | |
| 6,152,144 A | 11/2000 | Lesh et al. | |
| 6,155,968 A | 12/2000 | Wilk | |
| 6,155,972 A | 12/2000 | Nauertz et al. | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,165,121 A | 12/2000 | Alferness | |
| 6,165,122 A | 12/2000 | Alferness | |
| 6,165,183 A | 12/2000 | Kuehn et al. | |
| 6,169,922 B1 | 1/2001 | Alferness et al. | |
| 6,174,279 B1 | 1/2001 | Girard | |
| 6,174,332 B1 | 1/2001 | Loch et al. | |
| 6,179,791 B1 | 1/2001 | Krueger | |
| 6,182,664 B1 | 2/2001 | Cosgrove | |
| 6,183,411 B1 | 2/2001 | Mortier et al. | |
| 6,183,512 B1 | 2/2001 | Howanec, Jr. et al. | |
| 6,190,408 B1 | 2/2001 | Malvin | |
| 6,193,648 B1 | 2/2001 | Krueger | |
| 6,197,053 B1 | 3/2001 | Cosgrove et al. | |
| 6,206,004 B1 | 3/2001 | Schmidt et al. | |
| 6,206,820 B1 | 3/2001 | Kazi et al. | |
| 6,210,432 B1 | 4/2001 | Solem et al. | |
| 6,217,610 B1 | 4/2001 | Carpentier et al. | |
| 6,221,013 B1 | 4/2001 | Panescu et al. | |
| 6,221,103 B1 | 4/2001 | Melvin | |
| 6,221,104 B1 | 4/2001 | Buckberg et al. | |
| 6,224,540 B1 | 5/2001 | Lederman et al. | |
| 6,230,714 B1 | 5/2001 | Alferness et al. | |
| 6,231,518 B1 | 5/2001 | Grabek et al. | |
| 6,231,561 B1 | 5/2001 | Frazier et al. | |
| 6,231,602 B1 | 5/2001 | Carpentier et al. | |
| 6,238,334 B1 | 5/2001 | Easterbrook, III et al. | |
| 6,241,654 B1 | 6/2001 | Alferness | |

| | | |
|---|---|---|
| 6,245,102 B1 | 6/2001 | Jayaraman |
| 6,245,105 B1 | 6/2001 | Nguyen et al. |
| 6,250,308 B1 | 6/2001 | Cox |
| 6,251,061 B1 | 6/2001 | Hastings et al. |
| 6,258,021 B1 | 7/2001 | Wilk |
| 6,258,023 B1 | 7/2001 | Rogers et al. |
| 6,260,552 B1 | 7/2001 | Mortier et al. |
| 6,260,820 B1 | 7/2001 | Chowdhury |
| 6,261,222 B1 | 7/2001 | Schweich, Jr. et al. |
| 6,264,602 B1 | 7/2001 | Mortier et al. |
| 6,266,550 B1 | 7/2001 | Selmon et al. |
| 6,269,819 B1 | 8/2001 | Oz et al. |
| 6,283,993 B1 | 9/2001 | Cosgrove et al. |
| 6,290,674 B1 | 9/2001 | Roue et al. |
| 6,293,906 B1 | 9/2001 | Vanden Hock et al. |
| 6,309,370 B1 | 10/2001 | Haim et al. |
| 6,312,447 B1 | 11/2001 | Grimes |
| 6,314,322 B1 | 11/2001 | Rosenberg |
| 6,328,727 B1 | 12/2001 | Frazier et al. |
| 6,331,157 B2 | 12/2001 | Hancock |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,338,712 B2 | 1/2002 | Spence et al. |
| 6,343,605 B1 | 2/2002 | Lafontaine |
| 6,360,749 B1 | 3/2002 | Jayaraman |
| 6,361,545 B1 | 3/2002 | Macoviak et al. |
| 6,370,429 B1 | 4/2002 | Alferness et al. |
| 6,375,608 B1 | 4/2002 | Alferness |
| 6,379,366 B1 | 4/2002 | Fleischman et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,406,422 B1 | 6/2002 | Landesberg |
| 6,409,759 B1 | 6/2002 | Peredo |
| 6,409,760 B1 | 6/2002 | Melvin |
| 6,416,459 B1 | 7/2002 | Haindl |
| 6,419,669 B1 | 7/2002 | Frazier et al. |
| 6,419,695 B1 | 7/2002 | Gabbay |
| 6,423,051 B1 | 7/2002 | Kaplan et al. |
| 6,425,856 B1 | 7/2002 | Shapland et al. |
| 6,432,039 B1 | 8/2002 | Wardle |
| 6,432,059 B2 | 8/2002 | Hickey |
| 6,436,088 B2 | 8/2002 | Frazier et al. |
| 6,439,237 B1 | 8/2002 | Buckberg et al. |
| 6,443,949 B2 | 9/2002 | Altman |
| 6,450,171 B1 | 9/2002 | Buckberg et al. |
| 6,458,100 B2 | 10/2002 | Roue et al. |
| 6,461,366 B1 | 10/2002 | Seguin |
| 6,478,729 B1 | 11/2002 | Rogers et al. |
| 6,482,146 B1 | 11/2002 | Alferness et al. |
| 6,488,706 B1 | 12/2002 | Solymar |
| 6,494,825 B1 | 12/2002 | Talpade |
| 6,508,756 B1 | 1/2003 | Kung et al. |
| 6,511,426 B1 | 1/2003 | Hossack et al. |
| 6,514,194 B2 | 2/2003 | Schweich, Jr. et al. |
| 6,520,904 B1 | 2/2003 | Melvin |
| 6,537,198 B1 | 3/2003 | Vidlund et al. |
| 6,537,203 B1 | 3/2003 | Alferness et al. |
| 6,537,314 B2 | 3/2003 | Langberg et al. |
| 6,544,167 B2 | 4/2003 | Buckberg et al. |
| 6,544,180 B1 | 4/2003 | Doten et al. |
| 6,547,821 B1 | 4/2003 | Taylor et al. |
| 6,569,198 B1 | 5/2003 | Wilson et al. |
| 6,572,529 B2 | 6/2003 | Wilk |
| 6,582,355 B2 | 6/2003 | Alferness et al. |
| 6,587,734 B2 | 7/2003 | Okuzumi |
| 6,589,160 B2 | 7/2003 | Schweich, Jr. et al. |
| 6,592,619 B2 | 7/2003 | Melvin |
| 6,595,912 B2 | 7/2003 | Lau et al. |
| 6,602,182 B1 | 8/2003 | Milbocker |
| 6,602,184 B2 | 8/2003 | Lau et al. |
| 6,612,278 B2 | 9/2003 | Kampichler |
| 6,612,978 B2 | 9/2003 | Lau et al. |
| 6,612,979 B2 | 9/2003 | Lau et al. |
| 6,616,596 B1 | 9/2003 | Milbocker |
| 6,616,684 B1 | 9/2003 | Vidlund et al. |
| 6,619,291 B2 | 9/2003 | Hlavka |
| 6,622,730 B2 | 9/2003 | Ekvall et al. |
| 6,626,821 B1 | 9/2003 | Kung et al. |
| 6,626,930 B1 | 9/2003 | Allen et al. |
| 6,629,534 B1 | 10/2003 | Dell et al. |
| 6,629,921 B1 | 10/2003 | Schweich, Jr. et al. |
| 6,645,139 B2 | 11/2003 | Haindl |
| 6,651,671 B1 | 11/2003 | Donlon et al. |
| 6,656,221 B2 | 12/2003 | Taylor et al. |
| 6,663,558 B2 | 12/2003 | Lau et al. |
| 6,669,708 B1 | 12/2003 | Nissenbaum et al. |
| 6,673,009 B1 | 1/2004 | Vanden Hoek et al. |
| 6,676,702 B2 | 1/2004 | Mathis |
| 6,681,773 B2 | 1/2004 | Murphy et al. |
| 6,682,474 B2 | 1/2004 | Lau et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,685,646 B2 | 2/2004 | Cespedes et al. |
| 6,689,048 B2 | 2/2004 | Vanden Hoek et al. |
| 6,695,768 B1 | 2/2004 | Levine et al. |
| 6,695,866 B1 | 2/2004 | Kuehn et al. |
| 6,701,929 B2 | 3/2004 | Hussein |
| 6,702,732 B1 | 3/2004 | Lau et al. |
| 6,702,763 B2 | 3/2004 | Murphy et al. |
| 6,702,826 B2 | 3/2004 | Liddicoat et al. |
| 6,706,065 B2 | 3/2004 | Langberg et al. |
| 6,709,456 B2 | 3/2004 | Langberg et al. |
| 6,712,804 B2 | 3/2004 | Roue et al. |
| 6,716,158 B2 | 4/2004 | Raman et al. |
| 6,719,767 B1 | 4/2004 | Kimblad |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,016 B1 | 5/2004 | Walsh et al. |
| 6,733,525 B2 | 5/2004 | Pease et al. |
| 6,740,107 B2 | 5/2004 | Graham et al. |
| 6,752,813 B2 | 6/2004 | Goldfarb et al. |
| 6,755,777 B2 | 6/2004 | Schweich, Jr. et al. |
| 6,755,779 B2 | 6/2004 | Vanden Hoek et al. |
| 6,767,362 B2 | 7/2004 | Schreck |
| 6,769,434 B2 | 8/2004 | Liddicoat et al. |
| 6,776,754 B1 | 8/2004 | Wilk |
| 6,790,231 B2 | 9/2004 | Liddicoat et al. |
| 6,793,673 B2 | 9/2004 | Kowalsky et al. |
| 6,800,090 B2 | 10/2004 | Alferness et al. |
| 6,805,710 B2 | 10/2004 | Bolling et al. |
| 6,810,882 B2 | 11/2004 | Langberg et al. |
| 6,814,700 B1 | 11/2004 | Mueller et al. |
| 6,837,247 B2 | 1/2005 | Buckberg et al. |
| 6,846,296 B1 | 1/2005 | Milbocker et al. |
| 6,869,444 B2 | 3/2005 | Gabbay |
| 6,875,224 B2 | 4/2005 | Grimes |
| 6,876,887 B2 | 4/2005 | Okuzumi |
| 6,881,185 B2 | 4/2005 | Vanden Hock et al. |
| 6,887,192 B1 | 5/2005 | Whayne et al. |
| 6,890,353 B2 | 5/2005 | Cohn et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,908,426 B2 | 6/2005 | Shapland et al. |
| 6,908,478 B2 | 6/2005 | Alferness et al. |
| 6,913,608 B2 | 7/2005 | Liddicoat et al. |
| 6,918,917 B1 | 7/2005 | Nguyen et al. |
| 6,921,407 B2 | 7/2005 | Nguyen et al. |
| 6,949,122 B2 | 9/2005 | Adams et al. |
| 6,955,689 B2 | 10/2005 | Ryan et al. |
| 6,959,711 B2 | 11/2005 | Murphy et al. |
| 6,960,229 B2 | 11/2005 | Mathis et al. |
| 6,962,605 B2 | 11/2005 | Cosgrove et al. |
| 6,966,926 B2 | 11/2005 | Mathis |
| 6,976,995 B2 | 12/2005 | Mathis et al. |
| 6,989,028 B2 | 1/2006 | Lashinski et al. |
| 6,994,093 B2 | 2/2006 | Murphy et al. |
| 6,997,865 B2 | 2/2006 | Alferness et al. |
| 6,997,951 B2 | 2/2006 | Solem et al. |
| 7,004,958 B2 | 2/2006 | Adams et al. |
| 7,011,682 B2 | 3/2006 | Lashinski et al. |
| 7,022,064 B2 | 4/2006 | Alferness et al. |
| 7,025,719 B2 | 4/2006 | Alferness et al. |

| | | |
|---|---|---|
| 7,037,334 B1 | 5/2006 | Hlavka et al. |
| 7,044,967 B1 | 5/2006 | Solem et al. |
| 7,052,487 B2 | 5/2006 | Cohn et al. |
| 7,056,280 B2 | 6/2006 | Buckberg et al. |
| 7,060,021 B1 | 6/2006 | Wilk |
| 7,063,722 B2 | 6/2006 | Marquez |
| 7,070,618 B2 | 7/2006 | Streeter |
| 7,090,695 B2 | 8/2006 | Solem et al. |
| 7,112,207 B2 | 9/2006 | Allen et al. |
| 7,115,110 B2 | 10/2006 | Frazier et al. |
| 7,153,258 B2 | 12/2006 | Alferness et al. |
| 7,163,507 B2 | 1/2007 | Alferness |
| 7,166,071 B2 | 1/2007 | Alferness |
| 7,166,126 B2 | 1/2007 | Spence et al. |
| 7,179,282 B2 | 2/2007 | Alferness et al. |
| 7,186,264 B2 | 3/2007 | Liddicoat et al. |
| 7,189,199 B2 | 3/2007 | McCarthy et al. |
| 7,192,442 B2 | 3/2007 | Solem et al. |
| 7,214,181 B2 | 5/2007 | Shapland et al. |
| 7,226,467 B2 | 6/2007 | Lucatero et al. |
| 7,229,469 B1 | 6/2007 | Witzel et al. |
| 7,241,310 B2 | 7/2007 | Taylor et al. |
| 7,252,632 B2 | 8/2007 | Shapland et al. |
| 7,255,674 B2 | 8/2007 | Alferness |
| 7,261,684 B2 | 8/2007 | Alferness |
| 7,264,587 B2 | 9/2007 | Chin |
| 7,270,676 B2 | 9/2007 | Alferness et al. |
| 7,275,546 B2 | 10/2007 | Buckberg et al. |
| 7,278,964 B2 | 10/2007 | Alferness |
| 7,291,168 B2 | 11/2007 | Macoviak et al. |
| 7,296,577 B2 | 11/2007 | Lashinski et al. |
| 7,300,462 B2 | 11/2007 | Swinford et al. |
| 7,311,728 B2 | 12/2007 | Solem et al. |
| 7,311,731 B2 | 12/2007 | Lesniak et al. |
| 7,326,174 B2 | 2/2008 | Cox et al. |
| 7,329,280 B2 | 2/2008 | Bolling et al. |
| 7,351,260 B2 | 4/2008 | Nieminen et al. |
| 7,361,137 B2 | 4/2008 | Taylor et al. |
| 7,371,259 B2 | 5/2008 | Ryan et al. |
| 7,373,207 B2 | 5/2008 | Lattouf |
| 7,377,940 B2 | 5/2008 | Ryan et al. |
| 7,381,182 B2 | 6/2008 | Raman et al. |
| 7,381,220 B2 | 6/2008 | Macoviak et al. |
| 7,390,293 B2 | 6/2008 | Jayaraman |
| 7,404,824 B1 | 7/2008 | Webler et al. |
| 7,410,461 B2 | 8/2008 | Lau et al. |
| 7,419,466 B2 | 9/2008 | Vanden Hoek et al. |
| 7,678,145 B2 * | 3/2010 | Vidlund et al. ............... 623/2.36 |
| 2001/0003986 A1 | 6/2001 | Cosgrove |
| 2001/0005787 A1 | 6/2001 | Oz et al. |
| 2001/0009976 A1 | 7/2001 | Panescu et al. |
| 2001/0014800 A1 | 8/2001 | Frazier et al. |
| 2001/0014811 A1 | 8/2001 | Hussein |
| 2001/0018611 A1 | 8/2001 | Solem et al. |
| 2001/0021874 A1 | 9/2001 | Carpentier et al. |
| 2001/0029314 A1 | 10/2001 | Alferness et al. |
| 2001/0034551 A1 | 10/2001 | Cox |
| 2001/0037123 A1 | 11/2001 | Hancock |
| 2001/0039434 A1 | 11/2001 | Frazier et al. |
| 2001/0039435 A1 | 11/2001 | Roue et al. |
| 2001/0039436 A1 | 11/2001 | Frazier et al. |
| 2001/0041821 A1 | 11/2001 | Wilk |
| 2001/0041914 A1 | 11/2001 | Frazier et al. |
| 2001/0041915 A1 | 11/2001 | Roue et al. |
| 2001/0044568 A1 | 11/2001 | Langberg et al. |
| 2001/0047122 A1 | 11/2001 | Vanden Hoek et al. |
| 2001/0049492 A1 | 12/2001 | Frazier et al. |
| 2002/0007216 A1 | 1/2002 | Melvin |
| 2002/0013571 A1 | 1/2002 | Goldfarb et al. |
| 2002/0016628 A1 | 2/2002 | Langberg et al. |
| 2002/0019580 A1 | 2/2002 | Lau et al. |
| 2002/0022880 A1 | 2/2002 | Melvin |
| 2002/0026092 A1 | 2/2002 | Buckberg et al. |
| 2002/0026094 A1 | 2/2002 | Roth |
| 2002/0028981 A1 | 3/2002 | Lau et al. |
| 2002/0029783 A1 | 3/2002 | Stevens et al. |
| 2002/0032364 A1 | 3/2002 | Lau et al. |
| 2002/0042554 A1 | 4/2002 | Alferness et al. |
| 2002/0045798 A1 | 4/2002 | Lau et al. |
| 2002/0045799 A1 | 4/2002 | Lau et al. |
| 2002/0045800 A1 | 4/2002 | Lau et al. |
| 2002/0052538 A1 | 5/2002 | Lau et al. |
| 2002/0056461 A1 | 5/2002 | Jayaraman |
| 2002/0058855 A1 | 5/2002 | Schweich, Jr. et al. |
| 2002/0065449 A1 | 5/2002 | Wardle |
| 2002/0065465 A1 | 5/2002 | Panescu et al. |
| 2002/0065554 A1 | 5/2002 | Streeter |
| 2002/0068850 A1 | 6/2002 | Vanden Hoek et al. |
| 2002/0077532 A1 | 6/2002 | Gannoe et al. |
| 2002/0082647 A1 | 6/2002 | Alferness et al. |
| 2002/0087173 A1 | 7/2002 | Alferness et al. |
| 2002/0091296 A1 | 7/2002 | Alferness |
| 2002/0103511 A1 | 8/2002 | Alferness et al. |
| 2002/0103532 A1 | 8/2002 | Langberg et al. |
| 2002/0103533 A1 | 8/2002 | Langberg et al. |
| 2002/0111533 A1 | 8/2002 | Melvin |
| 2002/0111567 A1 | 8/2002 | Vanden Hoek et al. |
| 2002/0111636 A1 | 8/2002 | Fleischman et al. |
| 2002/0133055 A1 | 9/2002 | Haindl |
| 2002/0143250 A1 | 10/2002 | Panescu et al. |
| 2002/0151766 A1 | 10/2002 | Shapland et al. |
| 2002/0151961 A1 | 10/2002 | Lashinski et al. |
| 2002/0161275 A1 | 10/2002 | Schweich, Jr. et al. |
| 2002/0169358 A1 | 11/2002 | Mortier et al. |
| 2002/0169359 A1 | 11/2002 | McCarthy et al. |
| 2002/0169360 A1 | 11/2002 | Taylor et al. |
| 2002/0169502 A1 | 11/2002 | Mathis |
| 2002/0169504 A1 | 11/2002 | Alferness et al. |
| 2002/0173694 A1 | 11/2002 | Mortier et al. |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2002/0188350 A1 | 12/2002 | Arru et al. |
| 2003/0004396 A1 | 1/2003 | Vanden Hock et al. |
| 2003/0009081 A1 | 1/2003 | Rogers et al. |
| 2003/0023132 A1 | 1/2003 | Melvin et al. |
| 2003/0028077 A1 | 2/2003 | Alferness et al. |
| 2003/0032979 A1 | 2/2003 | Mortier et al. |
| 2003/0045771 A1 | 3/2003 | Schweich, Jr. et al. |
| 2003/0045776 A1 | 3/2003 | Alferness et al. |
| 2003/0045896 A1 | 3/2003 | Murphy et al. |
| 2003/0050529 A1 | 3/2003 | Vidlund et al. |
| 2003/0050659 A1 | 3/2003 | Murphy et al. |
| 2003/0060674 A1 | 3/2003 | Gifford, III et al. |
| 2003/0065248 A1 | 4/2003 | Lau et al. |
| 2003/0069467 A1 | 4/2003 | Lau et al. |
| 2003/0078465 A1 | 4/2003 | Pai et al. |
| 2003/0078653 A1 | 4/2003 | Vesely et al. |
| 2003/0078671 A1 | 4/2003 | Lesniak et al. |
| 2003/0093104 A1 | 5/2003 | Bonner et al. |
| 2003/0105519 A1 | 6/2003 | Fasol et al. |
| 2003/0120340 A1 | 6/2003 | Liska et al. |
| 2003/0130730 A1 | 7/2003 | Cohn et al. |
| 2003/0130731 A1 | 7/2003 | Vidlund et al. |
| 2003/0135267 A1 | 7/2003 | Solem et al. |
| 2003/0144697 A1 | 7/2003 | Mathis et al. |
| 2003/0149333 A1 | 8/2003 | Alferness |
| 2003/0153946 A1 | 8/2003 | Kimblad |
| 2003/0158570 A1 | 8/2003 | Ferrazzi |
| 2003/0166992 A1 | 9/2003 | Schweich, Jr. et al. |
| 2003/0171641 A1 | 9/2003 | Schweich, Jr. et al. |
| 2003/0171776 A1 | 9/2003 | Adams et al. |
| 2003/0171806 A1 | 9/2003 | Mathis et al. |
| 2003/0181928 A1 | 9/2003 | Vidlund et al. |
| 2003/0191538 A1 | 10/2003 | Buckberg et al. |
| 2003/0199733 A1 | 10/2003 | Shapland et al. |
| 2003/0212453 A1 | 11/2003 | Mathis et al. |
| 2003/0225454 A1 | 12/2003 | Mathis et al. |
| 2003/0229260 A1 | 12/2003 | Girard et al. |
| 2003/0229261 A1 | 12/2003 | Girard et al. |
| 2003/0229265 A1 | 12/2003 | Girard et al. |
| 2003/0229266 A1 | 12/2003 | Cox et al. |
| 2003/0233022 A1 | 12/2003 | Vidlund et al. |
| 2003/0233142 A1 | 12/2003 | Morales et al. |
| 2003/0236569 A1 | 12/2003 | Mathis et al. |

| Publication No. | Date | Inventors |
|---|---|---|
| 2004/0002719 A1 | 1/2004 | Oz et al. |
| 2004/0003819 A1 | 1/2004 | St. Goar et al. |
| 2004/0010305 A1 | 1/2004 | Alferness et al. |
| 2004/0015039 A1 | 1/2004 | Melvin |
| 2004/0015040 A1 | 1/2004 | Melvin |
| 2004/0015041 A1 | 1/2004 | Melvin |
| 2004/0019377 A1 | 1/2004 | Taylor et al. |
| 2004/0019378 A1 | 1/2004 | Hlavka et al. |
| 2004/0024286 A1 | 2/2004 | Melvin |
| 2004/0030382 A1 | 2/2004 | St. Goar et al. |
| 2004/0034271 A1 | 2/2004 | Melvin et al. |
| 2004/0039442 A1 | 2/2004 | St. Goar et al. |
| 2004/0039443 A1 | 2/2004 | Solem et al. |
| 2004/0044365 A1 | 3/2004 | Bachman |
| 2004/0049115 A1 | 3/2004 | Murphy et al. |
| 2004/0049116 A1 | 3/2004 | Murphy et al. |
| 2004/0059180 A1 | 3/2004 | Melvin |
| 2004/0059181 A1 | 3/2004 | Alferness |
| 2004/0059182 A1 | 3/2004 | Alferness |
| 2004/0059187 A1 | 3/2004 | Alferness |
| 2004/0059188 A1 | 3/2004 | Alferness |
| 2004/0059189 A1 | 3/2004 | Alferness |
| 2004/0059351 A1 | 3/2004 | Eigler et al. |
| 2004/0064014 A1 | 4/2004 | Melvin et al. |
| 2004/0073302 A1 | 4/2004 | Rourke et al. |
| 2004/0092962 A1 | 5/2004 | Thornton et al. |
| 2004/0093023 A1 | 5/2004 | Allen et al. |
| 2004/0102678 A1 | 5/2004 | Haindl |
| 2004/0102679 A1 | 5/2004 | Alferness et al. |
| 2004/0102839 A1 | 5/2004 | Cohn et al. |
| 2004/0102840 A1 | 5/2004 | Solem et al. |
| 2004/0111101 A1 | 6/2004 | Chin |
| 2004/0127983 A1 | 7/2004 | Mortier et al. |
| 2004/0133063 A1 | 7/2004 | McCarthy et al. |
| 2004/0133069 A1 | 7/2004 | Shapland et al. |
| 2004/0152947 A1 | 8/2004 | Schroeder et al. |
| 2004/0158123 A1 | 8/2004 | Jayaraman |
| 2004/0162610 A1 | 8/2004 | Liska et al. |
| 2004/0167374 A1 | 8/2004 | Schweich et al. |
| 2004/0167539 A1 | 8/2004 | Kuehn et al. |
| 2004/0171907 A1 | 9/2004 | Alferness et al. |
| 2004/0171908 A1 | 9/2004 | Alferness et al. |
| 2004/0171909 A1 | 9/2004 | Alferness |
| 2004/0176678 A1 | 9/2004 | Murphy et al. |
| 2004/0176679 A1 | 9/2004 | Murphy et al. |
| 2004/0176840 A1 | 9/2004 | Langberg et al. |
| 2004/0181121 A1 | 9/2004 | Alferness et al. |
| 2004/0181122 A1 | 9/2004 | Alferness et al. |
| 2004/0181123 A1 | 9/2004 | Alferness et al. |
| 2004/0181124 A1 | 9/2004 | Alferness |
| 2004/0181125 A1 | 9/2004 | Alferness et al. |
| 2004/0181126 A1 | 9/2004 | Buckberg et al. |
| 2004/0186342 A1 | 9/2004 | Vanden Hock et al. |
| 2004/0193260 A1 | 9/2004 | Alferness et al. |
| 2004/0199183 A1 | 10/2004 | Oz et al. |
| 2004/0210240 A1 | 10/2004 | Saint |
| 2004/0210304 A1 | 10/2004 | Seguin et al. |
| 2004/0225300 A1 | 11/2004 | Goldfarb et al. |
| 2004/0249452 A1 | 12/2004 | Adams et al. |
| 2004/0267083 A1 | 12/2004 | McCarthy et al. |
| 2005/0004428 A1 | 1/2005 | Cox et al. |
| 2005/0004666 A1 | 1/2005 | Alfieri et al. |
| 2005/0021056 A1 | 1/2005 | St. Goar et al. |
| 2005/0021057 A1 | 1/2005 | St. Goar et al. |
| 2005/0021135 A1 | 1/2005 | Ryan et al. |
| 2005/0027351 A1 | 2/2005 | Reuter et al. |
| 2005/0027353 A1 | 2/2005 | Alferness et al. |
| 2005/0033419 A1 | 2/2005 | Alferness et al. |
| 2005/0033446 A1 | 2/2005 | Deem et al. |
| 2005/0038507 A1 | 2/2005 | Alferness et al. |
| 2005/0043792 A1 | 2/2005 | Solem et al. |
| 2005/0049679 A1 | 3/2005 | Taylor et al. |
| 2005/0049698 A1 | 3/2005 | Bolling et al. |
| 2005/0060030 A1 | 3/2005 | Lashinski et al. |
| 2005/0071000 A1 | 3/2005 | Liddicoat et al. |
| 2005/0075723 A1 | 4/2005 | Schroeder et al. |
| 2005/0075727 A1 | 4/2005 | Wheatley |
| 2005/0080402 A1 | 4/2005 | Santamore et al. |
| 2005/0080483 A1 | 4/2005 | Solem et al. |
| 2005/0085688 A1 | 4/2005 | Girard et al. |
| 2005/0095268 A1 | 5/2005 | Walsh et al. |
| 2005/0096740 A1 | 5/2005 | Langberg et al. |
| 2005/0107810 A1 | 5/2005 | Morales et al. |
| 2005/0113635 A1 | 5/2005 | Whayne et al. |
| 2005/0113811 A1 | 5/2005 | Houser et al. |
| 2005/0119519 A9 | 6/2005 | Girard et al. |
| 2005/0131533 A1 | 6/2005 | Alfier et al. |
| 2005/0149182 A1 | 7/2005 | Alferness et al. |
| 2005/0197528 A1 | 9/2005 | Vanden Hock et al. |
| 2005/0197692 A1 | 9/2005 | Pai et al. |
| 2005/0197693 A1 | 9/2005 | Pai et al. |
| 2005/0209690 A1 | 9/2005 | Mathis et al. |
| 2005/0216077 A1 | 9/2005 | Mathis et al. |
| 2005/0228217 A1 | 10/2005 | Alferness et al. |
| 2005/0261704 A1 | 11/2005 | Mathis et al. |
| 2005/0267574 A1 | 12/2005 | Cohn et al. |
| 2005/0272969 A1 | 12/2005 | Alferness et al. |
| 2006/0004443 A1 | 1/2006 | Liddicoat et al. |
| 2006/0009842 A1 | 1/2006 | Huynh et al. |
| 2006/0020336 A1 | 1/2006 | Liddicoat |
| 2006/0025856 A1 | 2/2006 | Ryan et al. |
| 2006/0041306 A1 | 2/2006 | Vidlund et al. |
| 2006/0052868 A1 | 3/2006 | Mortier et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0069430 A9 | 3/2006 | Rahdert et al. |
| 2006/0106456 A9 | 5/2006 | Machold et al. |
| 2006/0111607 A1 | 5/2006 | Alferness et al. |
| 2006/0116756 A1 | 6/2006 | Solem et al. |
| 2006/0116757 A1 | 6/2006 | Lashinski et al. |
| 2006/0137697 A1 | 6/2006 | Murphy et al. |
| 2006/0142854 A1 | 6/2006 | Alferness et al. |
| 2006/0149122 A1 | 7/2006 | Shapland et al. |
| 2006/0149123 A1 | 7/2006 | Vidlund et al. |
| 2006/0149368 A1 | 7/2006 | Spence |
| 2006/0155165 A1 | 7/2006 | Vanden Hock et al. |
| 2006/0161040 A1 | 7/2006 | McCarthy et al. |
| 2006/0184241 A1 | 8/2006 | Marquez |
| 2006/0195012 A1 | 8/2006 | Mortier et al. |
| 2006/0212114 A1 | 9/2006 | Menicanti et al. |
| 2006/0229717 A1 | 10/2006 | Cohn et al. |
| 2006/0235265 A1 | 10/2006 | Alferness et al. |
| 2006/0241340 A1 | 10/2006 | Schroeder et al. |
| 2006/0247492 A1 | 11/2006 | Streeter |
| 2006/0252984 A1 | 11/2006 | Rahdert et al. |
| 2006/0258900 A1 | 11/2006 | Buckberg et al. |
| 2007/0004962 A1 | 1/2007 | Alferness et al. |
| 2007/0038293 A1 | 2/2007 | St. Goar et al. |
| 2007/0050020 A1 | 3/2007 | Spence |
| 2007/0055303 A1 | 3/2007 | Vidlund et al. |
| 2007/0066879 A1 | 3/2007 | Mathis et al. |
| 2007/0100442 A1 | 5/2007 | Solem et al. |
| 2007/0112244 A1 | 5/2007 | McCarthy et al. |
| 2007/0118155 A1 | 5/2007 | Goldfarb et al. |
| 2007/0129598 A1 | 6/2007 | Raman et al. |
| 2007/0129737 A1 | 6/2007 | Goldfarb et al. |
| 2007/0161846 A1 | 7/2007 | Nikolic et al. |
| 2007/0208211 A1 | 9/2007 | Shapland et al. |
| 2007/0213814 A1 | 9/2007 | Liddicoat et al. |
| 2007/0225547 A1 | 9/2007 | Alferness |
| 2007/0288090 A1 | 12/2007 | Solem et al. |
| 2008/0033235 A1 | 2/2008 | Shapland et al. |
| 2008/0051807 A1 | 2/2008 | St. Goar et al. |
| 2008/0065047 A1 | 3/2008 | Sabbah et al. |
| 2008/0091191 A1 | 4/2008 | Witzel et al. |
| 2008/0097489 A1 | 4/2008 | Goldfarb et al. |
| 2008/0097593 A1 | 4/2008 | Bolling et al. |
| 2008/0125622 A1 | 5/2008 | Walsh et al. |
| 2008/0140191 A1 | 6/2008 | Mathis et al. |
| 2008/0147184 A1 | 6/2008 | Lattouf |
| 2008/0154359 A1 | 6/2008 | Salgo et al. |
| 2008/0161638 A1 | 7/2008 | Taylor et al. |
| 2008/0167714 A1 | 7/2008 | St. Goar et al. |
| 2008/0183194 A1 | 7/2008 | Goldfarb et al. |
| 2008/0183284 A1 | 7/2008 | Ryan et al. |
| 2008/0188861 A1 | 8/2008 | Ryan et al. |

| | | | |
|---|---|---|---|
| 2008/0195200 A1 | 8/2008 | Vidlund et al. | |
| 2008/0208331 A1 | 8/2008 | McCarthy et al. | |
| 2008/0215008 A1 | 9/2008 | Nance et al. | |

FOREIGN PATENT DOCUMENTS

| | | |
|---|---|---|
| DE | 36 14 292 C1 | 11/1987 |
| DE | 42 34 127 A1 | 5/1994 |
| DE | 295 00 381 U1 | 7/1995 |
| DE | 195 38 796 A1 | 4/1997 |
| DE | 296 19 294 U1 | 7/1997 |
| DE | 298 24 017 U1 | 6/1998 |
| DE | 198 26 675 | 3/1999 |
| DE | 199 47 885 A1 | 4/2000 |
| EP | 0 583 012 A1 | 2/1994 |
| EP | 0 792 621 A1 | 9/1997 |
| EP | 0 820 729 A1 | 1/1998 |
| EP | 1 129 736 A1 | 9/2001 |
| GB | 2214428 | 9/1989 |
| NL | 9 200 878 | 12/1993 |
| SU | 1335260 A1 | 9/1987 |
| WO | WO 91/19465 A1 | 12/1991 |
| WO | WO 95/06447 A1 | 3/1995 |
| WO | WO 95/16407 A1 | 6/1995 |
| WO | WO 95/16476 A1 | 6/1995 |
| WO | WO 96/02197 A1 | 2/1996 |
| WO | WO 96/04852 A1 | 2/1996 |
| WO | WO 96/40356 A1 | 12/1996 |
| WO | WO 97/14286 A2 | 4/1997 |
| WO | WO 97/24082 A1 | 7/1997 |
| WO | WO 97/24083 A1 | 7/1997 |
| WO | WO 97/24101 A1 | 7/1997 |
| WO | WO 97/41779 A1 | 11/1997 |
| WO | WO 98/03213 A1 | 1/1998 |
| WO | WO 98/14136 A1 | 4/1998 |
| WO | WO 98/17347 A1 | 4/1998 |
| WO | WO 98/18393 A1 | 5/1998 |
| WO | WO 98/26738 A1 | 6/1998 |
| WO | WO 98/29041 A1 | 7/1998 |
| WO | WO 98/32382 A1 | 7/1998 |
| WO | WO 98/44969 A1 | 10/1998 |
| WO | WO 98/58598 A1 | 12/1998 |
| WO | WO 99/00059 A1 | 1/1999 |
| WO | WO 99/11201 A2 | 3/1999 |
| WO | WO 99/13777 A1 | 3/1999 |
| WO | WO 99/13936 A1 | 3/1999 |
| WO | WO 99/16350 A1 | 4/1999 |
| WO | WO 99/22784 A1 | 5/1999 |
| WO | WO 99/30647 A1 | 6/1999 |
| WO | WO 99/44534 A1 | 9/1999 |
| WO | WO 99/44680 A1 | 9/1999 |
| WO | WO 99/52470 A1 | 10/1999 |
| WO | WO 99/53977 A1 | 10/1999 |
| WO | WO 99/56655 A1 | 11/1999 |
| WO | WO 99/66969 A1 | 12/1999 |
| WO | WO 00/02500 A1 | 1/2000 |
| WO | WO 00/03759 A2 | 1/2000 |
| WO | WO 00/06026 A2 | 2/2000 |
| WO | WO 00/06028 A1 | 2/2000 |
| WO | WO 00/13722 A1 | 3/2000 |
| WO | WO 00/18320 A1 | 4/2000 |
| WO | WO 00/25842 A1 | 5/2000 |
| WO | WO 00/25853 A2 | 5/2000 |
| WO | WO 00/27304 A1 | 5/2000 |
| WO | WO 00/28912 A1 | 5/2000 |
| WO | WO 00/28918 A1 | 5/2000 |
| WO | WO 00/36995 A2 | 6/2000 |
| WO | WO 00/42919 A1 | 7/2000 |
| WO | WO 00/42950 A2 | 7/2000 |
| WO | WO 00/42951 A1 | 7/2000 |
| WO | WO 00/45735 A1 | 8/2000 |
| WO | WO 00/60995 A2 | 10/2000 |
| WO | WO 00/61033 A1 | 10/2000 |
| WO | WO 00/62715 A1 | 10/2000 |
| WO | WO 00/62727 A1 | 10/2000 |
| WO | WO 01/00111 A1 | 1/2001 |
| WO | WO 01/03608 A1 | 1/2001 |
| WO | WO 01/19291 A1 | 3/2001 |
| WO | WO 01/19292 A1 | 3/2001 |
| WO | WO 01/21070 A1 | 3/2001 |
| WO | WO 01/21098 A1 | 3/2001 |
| WO | WO 01/21099 A1 | 3/2001 |
| WO | WO 01/21247 A1 | 3/2001 |
| WO | WO 01/26557 A1 | 4/2001 |
| WO | WO 01/28432 A1 | 4/2001 |
| WO | WO 01/49217 A2 | 7/2001 |
| WO | WO 01/50981 A1 | 7/2001 |
| WO | WO 01/54562 A2 | 8/2001 |
| WO | WO 01/54618 A1 | 8/2001 |
| WO | WO 01/54745 A2 | 8/2001 |
| WO | WO 01/67985 A1 | 9/2001 |
| WO | WO 01/70116 A1 | 9/2001 |
| WO | WO 01/78625 A1 | 10/2001 |
| WO | WO 01/85061 A2 | 11/2001 |
| WO | WO 01/91667 A2 | 12/2001 |
| WO | WO 01/95830 A2 | 12/2001 |
| WO | WO 01/95831 A2 | 12/2001 |
| WO | WO 01/95832 A1 | 12/2001 |
| WO | WO 02/11625 A2 | 2/2002 |
| WO | WO 02/13726 A2 | 2/2002 |
| WO | WO 02/19917 A1 | 3/2002 |
| WO | WO 02/28450 A2 | 4/2002 |
| WO | WO 02/30292 A1 | 4/2002 |
| WO | WO 02/30335 A2 | 4/2002 |
| WO | WO 02/34167 A2 | 5/2002 |
| WO | WO 02/38081 A2 | 5/2002 |
| WO | WO 02/43617 A2 | 6/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/064035 A1 | 8/2002 |
| WO | WO 02/076284 A2 | 10/2002 |
| WO | WO 02/078576 A2 | 10/2002 |
| WO | WO 02/085251 A1 | 10/2002 |
| WO | WO 02/096275 A2 | 12/2002 |
| WO | WO 03/001893 A2 | 1/2003 |
| WO | WO 03/007778 A2 | 1/2003 |
| WO | WO 03/015611 A2 | 2/2003 |
| WO | WO 03/022131 A2 | 3/2003 |
| WO | WO 03/059209 A2 | 7/2003 |
| WO | WO 03/066147 A1 | 8/2003 |

OTHER PUBLICATIONS

Ianuzzo et at "Preservation of the Latissimus Dorsi Muscle During Cardiomyoplasty Surgery " *J. Card. Surg*, 1996:11:99-108.

Ianuzzo et al., "On Preconditioning of Skeletal Muscle: Application to Dynamic Cardiomyoplasty," Invited Commentary, *J. Card. Surg.*, 1996:11:109-110.

Chachques et al., "Latissimus Dorsi Dynamic Cardiomyoplasty," *Ann. Thorac. Surg.*, 1989:47:600-604.

Moreira et al., "Latissimus Dorsi Cardiomyoplasty in the Treatment of Patients with Dilated Cardiomyopathy," Supplement IV Circulation, Sep. 25, 1996, 7 pgs.

Lucas et al., "Long-Term Follow-Up (12 to 35 Weeks) After Dynamic Cardiomyoplasty," *JACC*, vol. 22, No. 3, Sep. 1993:758-67.

Batista et al., "Partial Left Ventriculectomy to Improve Left Ventricular Function in End-Stage Heart Disease," *J. Card. Surg.*, 1996:11:96-98.

"Congestive Heart Failure in the United States: A New Epidemic" Data Fact Sheet, National Heart, Lung, and Blood Institute, National Institutes of Health, Dec. 9, 1996, pp. 1-6.

Kormos et al., "Experience with Univentricular Support in Mortally Ill Cardiac Transplant Candidates," *Ann. Thorac. Surg.*, 1990:49:261-71.

Wampler et al., "Treatment of Cardiogenic Shock with the Hemopump Left Ventricular Assist Device," *Ann. Thorac. Surg.*, 1991:52:506-13.

McCarthy et al., "Clinical Experience with the Novacor Ventricular Assist System," *J. Thorac. Cardiovasc. Surg.*, 1991:102-578-87.

Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626-628.

Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629-631.

Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632-636.

Bearnson et al., "Development of a Prototype Magnetically Suspended Rotor Ventricular Assist Device," *ASAIO Journal*, 1996, pp. 275-280.

Sakakibara et al., "A Muscle Powered Cardiac Assist Device for Right Ventricular Support: Total Assist or Partial Assist?," *Trans. Am.Soc. Artif. Intern. Organs*, vol. XXXVI, 1990, pp. 372-375.

Medtronic, Inc. 1996 Annual Shareholders Report, 79 pages.

ABIOMED, Inc. Annual Report 1996, 32 pages.

Press Release dated Sep. 16, 1996, "ABIOMED Wins $8.5 Million Federal Contract to Qualify its Artificial Heart for Human Trials," 5 pages.

Press Release dated Sep. 26, 1996, ABIOMED's Temporary Artificial Heart System Reaches 200 U.S. Medical Center Milestone, 1 page.

Press Release dated May 17, 1996, "ABIOMED Receives FDA Approval to Expand Indications for Use of Cardiac Assist System," 1 page.

Press Release dated Oct. 3, 1995, "ABIOMED Wins $4.35 Million Contract from the National Heart, Lung and Blood Institutes to Develop Implantable Heart Booster," 1 page.

Press Release dated Sep. 29, 1995, "ABIOMED Wins NIH Grant to Develop Calcification-Resistant Plastic Heart Valve," 1 page.

Press Release dated Aug. 25, 1995, "ABIOMED Wins Research Grant from NIH to Develop Suturing Instrument for Abdominal surgery," 1 page.

Press Release dated Aug. 11, 1995, "ABIOMED Receives Grant from NIH to Develop Disposable Bearingless Centrifugal Blood Pump," 1 page.

Press Release dated Jun. 9, 1995, "ABIOMED Receives Grant from National Institutes of Health to Develop a Laser Welding Technique for Tissue Repair," 1 page.

Press Release dated Apr. 27, 1995, "ABIOMED's Temporary Artificial Heart System Reaches 1,000 Patient Milestone; BVS-5000 in More Than 100 U.S. Medical Centers," 1 page.

"Reversible Cardiomyopathy," *Thoratec's Heartbeat*, vol. 10.2, Aug. 1996, 4 pages.

Tsai et al., "Surface Modifying Additives for Improved Device-Blood Compatibility," *ASAIO Journal*, 1994, pp. 61-624.

Farrar et al., "A New Skeletal Muscle Linear-Pull Energy Convertor as a Power Source for Prosthetic Support Devices," *The Journal of Heart & Lung Transplantation*, vol. 11, No. 5, Sep. 1992, pp. 341-349.

Brochure entitled "Thoratec Ventricular Assist Device System—Because Heart Patients Come in All Sizes," date even with or prior to Jan. 2, 1997, 5 pages.

Press Release dated Oct. 3, 1994, "Heartmate System Becomes First Implantable Cardiac-Assist Device to be Approved for Commercial Sale in the U.S.," 2 pages.

Bocchi et al., "Clinical Outcome after Surgical Remodeling of Left Ventricle in Candidates to Heart Transplantation with Idiopathic Dilated Cardiomypathy—Short Term Results," date even with or prior to Jan. 2, 1997, 1 page.

Bach et al., "Early Improvement in Congestive Heart Failure after Correction of Secondary Mitral Regurgitation in End-Stage Cardiomyopathy," *American Heart Journal*, Jun. 1995, pp. 1165-1170.

Schuler et al., "Temporal Response of Left Ventricular Performance to Mitral Valve Surgery," vol. 59, No. 6, Jun. 1979, pp. 1218-1231.

Huikuri, "Effect of Mitral Valve Replacement on Left Ventricular Function in Mitral Regurgitation," *Br. Heart. J.*, vol. 49, 1983, pp. 328-333.

Pitarys II et al., "Long-Term Effects of Excision of the Mitral Apparatus on Global and Regional Ventricular Function in Humans," *JACC*, vol. 15, No. 3, Mar. 1, 1990, pp. 557-563.

Bolling et al., "Surgery for Acquired Heart Disease/Early Outcome of Mitral Valve Reconstruction in Patients with End-Stage Cardiomyopathy," *The Journal of Thoracic and Cardiovascular Surgery*, vol. 109, No. 4, Apr. 1995, pp. 676-683.

Masahiro et al., "Surgery for Acquired Heart Disease/Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138-1146.

Dickstein et al., "Heart Reduction Surgery: An Analysis of the Impact on Cardiac Function " *The Journal of Thoracic and Cardiovascular Surgery*, vol. 113, No. 6, Jun. 1997, 9 pages.

McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.

Alonso-Lej, M.D., "Adjustable Annuloplasty for Tricuspid Insufficiency," *The Annals of Thoracic Surgery*, vol. 46, No. 3, Sep. 1988, 2 pages.

Kurlansky et al., "Adjustable Annuloplasty for Tricuspid Insufficiency," *Ann. Thorac. Surg.*, 44:404-406, Oct. 1987.

Boyd et al., "Tricuspid Annuloplasty," *The Journal of Thoracic Cardiovascular Surgery*, vol. 68, No. 3, Sep. 1974, 8 pages.

Edie, M.D. et al., "Surgical repair of single ventricle," *The Journal of Thoracic and Cardiovascular Surgery*, vol. 66, No. 3, Sep. 1973, pp. 350-360.

McGoon, M.D. et al., "Correction of the univentricular heart having two atrioventricular valves," *The Journal of Thoracic and Cardiovascular Surgery*, vol. 74, No. 2, Aug. 1977, pp. 218-226.

Lev, M.D., et al., "Single (Primitive) Ventricle," *Circulation*, vol. 39, May 1969, pp. 577-591.

Westaby with Bosher, "Landmarks in Cardiac Surgery," 1997, pp. 198-199.

Shumacker, "Cardiac Aneurysms," *The Evolution of Cardiac Surgery*, 1992, pp. 159-165.

Feldt, M.D., "Current status of the septation procedure for univentricular heart," *The Journal of Thoracic and Cardiovascular Surgery*, vol. 82, No. 1, Jul. 1981, pp. 93-97.

Doty, M.D., "Septation of the univentricular heart," *The Journal of Thoracic and Cardiovascular Surgery*, vol. 78, No. 3, Sep. 1979, pp. 423-430.

Savage, M.D., "Repair of left ventricular aneurysm," *The Journal of Thoracic and Cardiovascular Surgery*, vol. 104, No. 3, Sep. 1992, pp. 752-762.

Cox, "Left Ventricular Aneurysms: Pathophysiologic Observations and Standard Resection," *Seminars in Thoracic and Cardiovascular Surgery*, vol. 9, No. 2, Apr. 1997, pp. 113-122.

Melvin, "Ventricular Radius Reduction Without Resection: A Computational Analysis," *ASAIO Journal*, 45:160-165, 1999.

"Heart 'jacket' could help stop heart failure progress," *Clinica*, Jul. 10, 2000.

McCarthy et al., "Device Based Left Ventricular Shape Change Immediately Reduces Left Ventricular Volume and Increases Ejection Fraction in a Pacing Induced Cardiomyopathy Model in Dogs: A Pilot Study," JACC, Feb. 2000.

McCarthy, Transcription of Mar. 13, 2000 presentation given at ACC.

Acorn cardiovascular, inc., "Acorn Cardiovascular Abstracts", Nov. 13, 2000.

Nation's First "Heart Jacket" Surgery to Treat Heart Failure Performed at HUP: Novel "Cardiac Support Device" Comes to America After Promising Results in Europe, Jun. 26, 2000.

Acorn cardiovascular, inc., Acorn Cardiovascular Company Overview, Jun. 2000.

Acorn cardiovascular, inc., Acorn Cardiovascular Business Plan, May 2000.

Acorn cardiovascular, inc., "Acorn Cardiovascular Highlights Abstracts", Mar. 10, 1999.

Acorn cardiovascular, inc., "Acorn Cardiovascular Highlights Abstracts", Apr. 19, 1999.

Acorn cardiovascular, inc., "Acorn Cardiovascular Highlights Abstracts", Oct. 1, 1999.

Acorn cardiovascular, inc., "Acorn Cardiovascular Highlights Abstracts", Nov. 9, 1999.

Batista, MD et al., "Partial Left Ventriculectomy to Treat End-Stage Heart Disease", *Ann. Thorac. Surg.*, 64:634-8, 1997.

Melvin DB et al., Reduction of Ventricular Wall Tensile Stress by Geometric Remodeling Device, *Poster text, ASAIO* 1999.

Kay et al., "Surgical Treatment of Mitral Insufficiency", *The Journal of Thoracic Surgery*, 1955, 29:618-620.

Harken et al., "The Surgical Correction of Mitral Insufficiency", *The Journal of Thoracic Surgery*, 1954, 28:604-627.

Bailey et al., "Closed Intracardiac Tactile Surgery", *Diseases of the Chest*, 1952, XXII:1-24.

Sakakibara, "A Surgical Approach to the Correction of Mitral Insufficiency", *Annals of Surgery*, 1955, 142:196-203.

Glenn et al., "The Surgical Treatment of Mitral Insufficiency: The Fate of a Vascularized Transchamber Intracardiac Graft", *Annals of Surgery*, 1955, 141:4:510-518.

Kay et al., "Surgical Treatment of Mitral Insufficiency", *Surgery*, 1955, 37:5:697-706.

Bailey et al., "The Surgical Correction of Mitral Insufficiency by the Use of Pericardial Grafts" *The Journal of Thoracic Surgery*, 1954, 28:6:551-603.

Harken et al., "The Surgical Correction of Mitral Insufficency", *Surgical Forum*, 1953, 4:4-7.

Shumacker, Jr., "Attempts to Control Mitral Regurgitation", *The Evolution of Cardiac Surgery*, 1992, 203-210.

Timek, Thomasz A. et al, Department of Cardiothoracic Surgery and Division of Cardiovascular Medicine, Stanford University School of Medicine, Stanford, CA, *Septal-Lateral Annular Cinching ('SLAC') reduces Mitral Annular Size without Perturbing Normal Annular Dynamics*, 2002.

Hung, Judy MD et al., *Reverse Ventricular Remodeling Reduces Ischemic Mitral Regurgitation: Echo-Guided Device Application in the Beating Hear*, Circulation, www.circulationaha.org, Nov. 12, 2002.

Baim, Donald S., MD, Brigham and Women's Hospital, Harvard Medical School, *Percutaneous Treatment of Mitral Regurgitation*, 2005.

Dullum, Mercedes K.C., *Update on Restraint Devices for Congestive Heart Failure*, Abstract and presentation slides given at Tech-Con 2005 for Society of Thoracic Surgeons, Jan. 23, 2005, 11 pages.

Alonso-Lej, *The Journal of Thoracic and Cardiovascular Surgery*, vol. 68, No. 3, Sep. 1974, p. 349.

Hayden et al., "Scintiphotographic Studies of Acquired Cardiovascular Disease," *Seminars in Nuclear Medicine*, vol. III, No. 2, Apr. 1973, pp. 177-190.

Benichoux et al., "A Method for the Surgical Correction of Mitral Insufficiency," *The Journal of Thoracic Surgery*, vol. 30, Jun.-Dec. 1955, pp. 148-158.

Carter et al., "Surgical Treatment of Mitral Insufficiency, An Experimental Study," *The Journal of Thoracic Surgery*, pp. 574-583.

Eisenhauer et al., "Closure of Prosthetic Paravalvular Mitral Regurgitation With the Gianturco-Grifka Vascular Occlusion Device," *Catheterization and Cardiovascular Interventions*, vol. 54, 2001, pp. 234-238.

Glenn et al., "The Implantation of a Vascularized Graft in the Chambers of the Heart, an Experimental Approach to the Correction of Valvular Insufficiency by Means of a Vertically Suspended Graft," *Surgical Forum*, Nov. 1954, pp. 5-11.

Johns et al., "Mitral Insufficiency: The Experimental Use of a Mobile Polyvinyl Sponge Prosthesis," Presented before the American Surgical Association, Cleveland, Ohio, Apr. 28, 1954, pp. 335-341.

Moscucci et al., "Coil Embolization of a Periprosthetic Mitral Valve Leak Associated with Severe Hemolytic Anemia," *Circulation*, 2001, pp. 1-2.

Rashkind et al., "Nonsurgical Closure of Patent Ductus Arteriosus: Clinical Application of the Rashkind PDA Occluder System," *Circulation*, vol. 75, No. 3, Mar. 1987, pp. 583-592.

\* cited by examiner

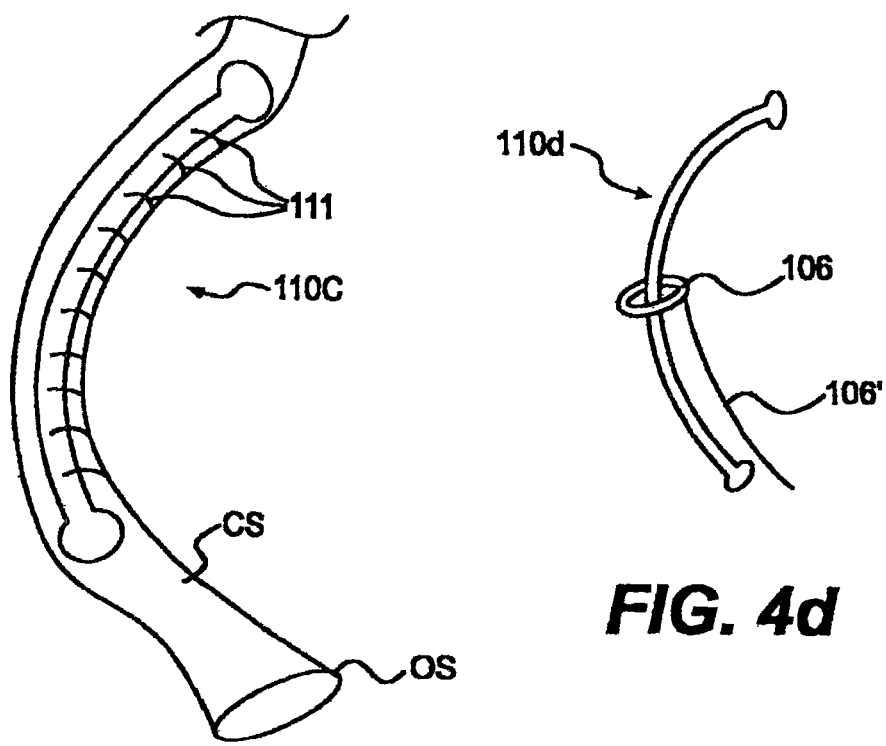
FIG. 4c
FIG. 4d
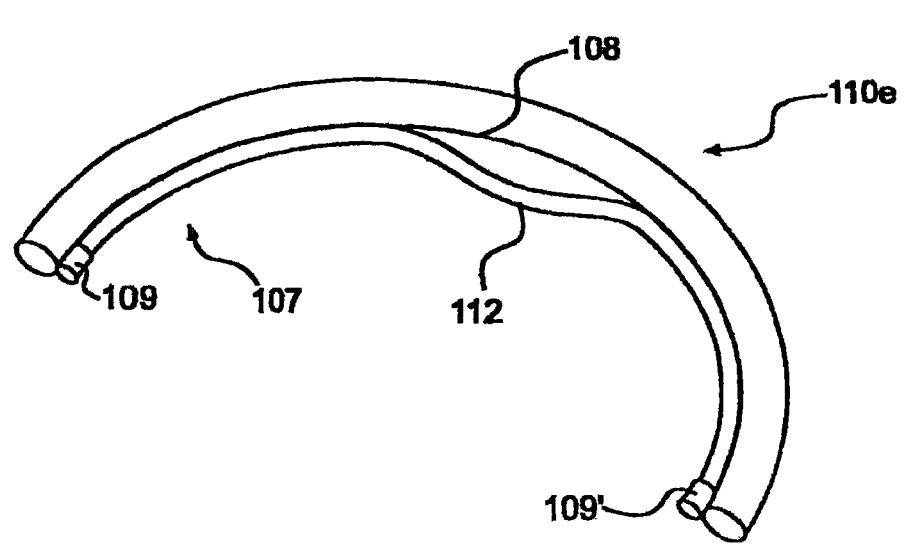
FIG. 4e

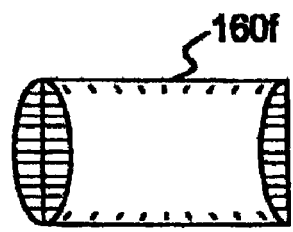
FIG. 11f
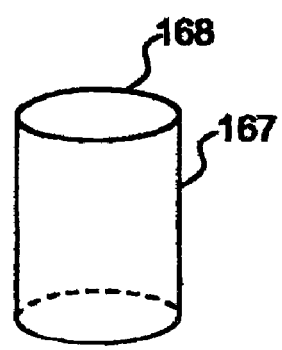 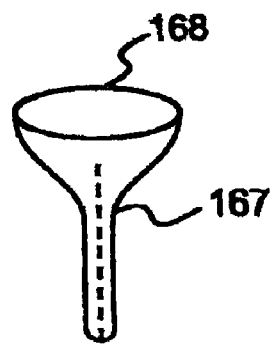
FIG. 11g(i)         FIG. 11g(ii)

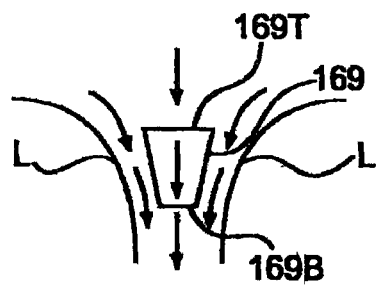
FIG. 11h(i)
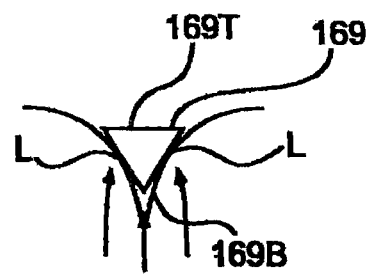
FIG. 11h(ii)
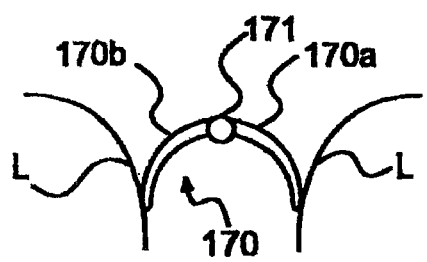
FIG. 11i(i)
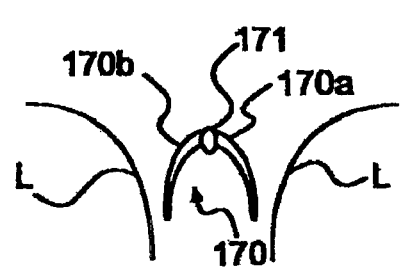
FIG. 11i(ii)
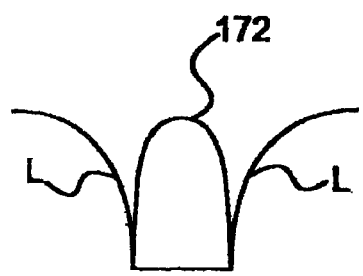
FIG. 11j(i)
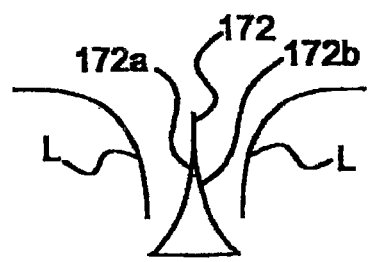
FIG. 11j(ii)

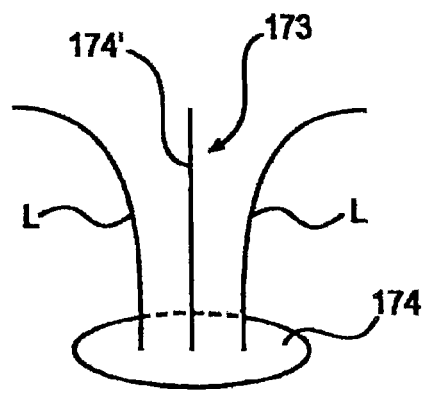
FIG. 11k
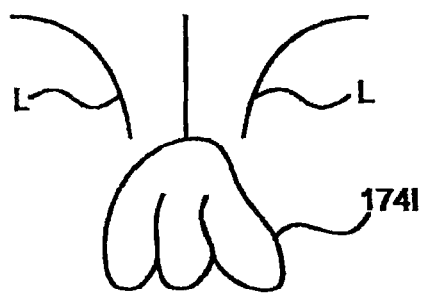 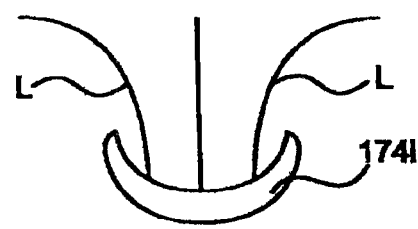
FIG. 11l(i)  FIG. 11l(ii)
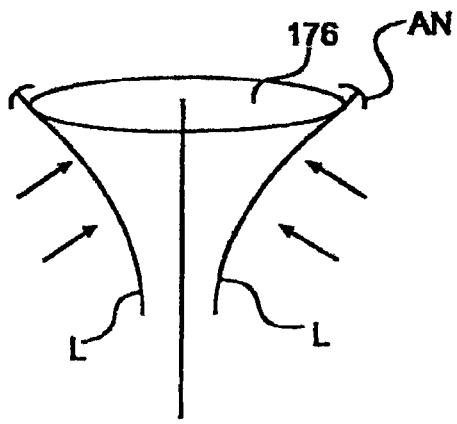 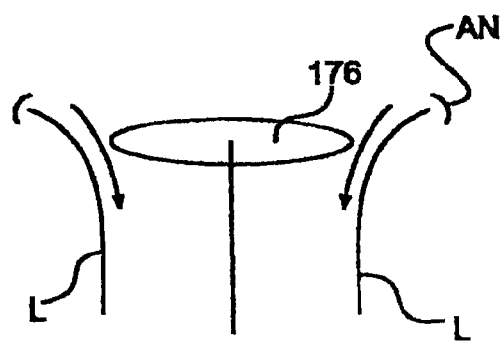
FIG. 11m(i)  FIG. 11m(ii)

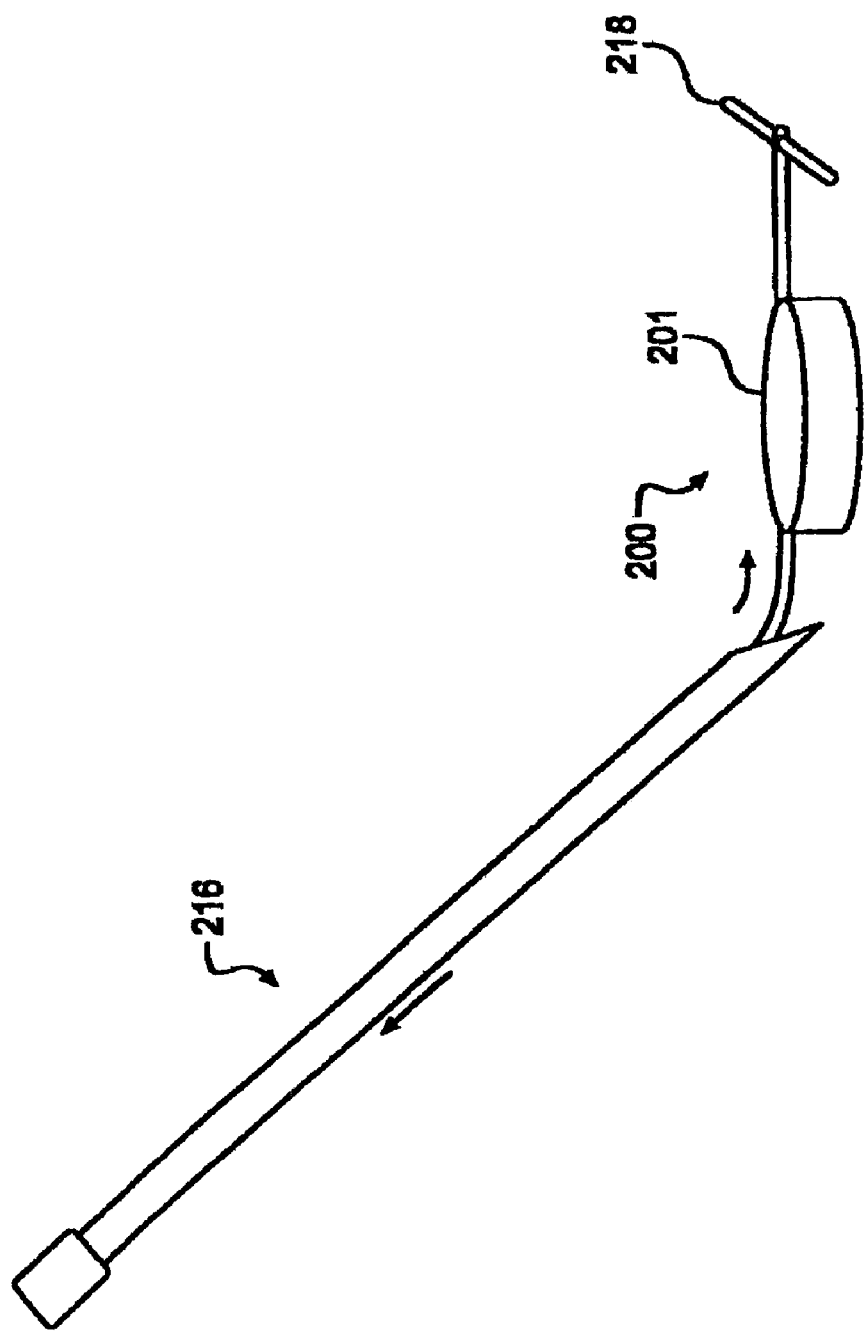

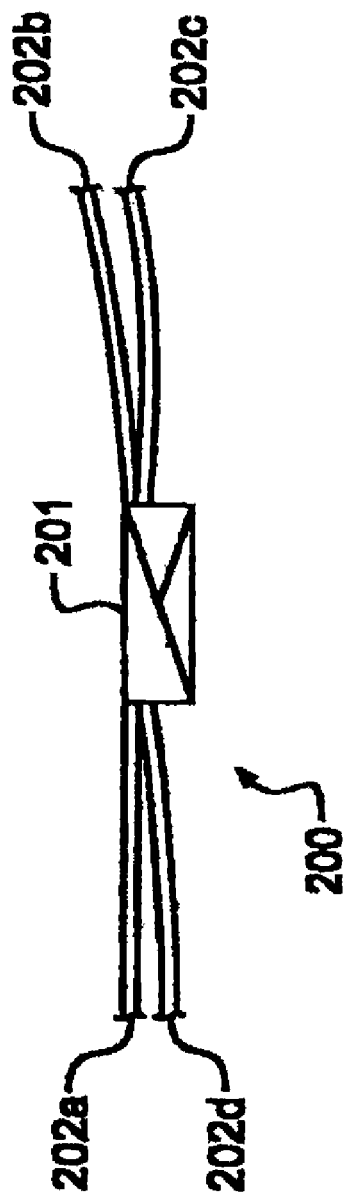

DEVICES AND METHODS FOR HEART VALVE TREATMENT

CROSS-REFERENCE TO RELATED APPLICATIONS

This application is a continuation of application Ser. No. 11/171,677, filed Jul. 1, 2005, now U.S. Pat. No. 7,678,145 now pending, which is a continuation of application Ser. No. 10/866,990, filed on Jun. 15, 2004, now U.S. Pat. No. 7,077,862, which is a continuation of application Ser. No. 10/040,784, filed on Jan. 9, 2002, now U.S. Pat. No. 6,764,510, all of which are incorporated herein by reference.

BACKGROUND OF THE INVENTION

1. Field of the Invention

The present invention relates to devices and related methods for treating and improving the function of dysfunctional heart valves. More particularly, the invention relates to devices and related methods that passively assist to dose a heart valve to improve valve function of poorly functioning valves.

2. Description of the Related Art

Various etiologies may result in heart valve insufficiency depending upon both the particular valve as well as the underlying disease state of the patient. For instance, a congenital defect may be present resulting in poor coaptation of the valve leaflets, such as in the case of a monocusp aortic valve, for example. Valve insufficiency also may result from an infection, such as rheumatic fever, for example, which may cause a degradation of the valve leaflets. Functional regurgitation also may be present. In such cases, the valve components may be normal pathologically, yet may be unable to function properly due to changes in the surrounding environment. Examples of such changes include geometric alterations of one or more heart chambers and/or decreases in myocardial contractility. In any case, the resultant volume overload that exists as a result of an insufficient valve may increase chamber wall stress. Such an increase in stress may eventually result in a dilatory process that further exacerbates valve dysfunction and degrades cardiac efficiency.

Mitral valve regurgitation often may be driven by the functional changes described above. Alterations in the geometric relationship between valvular components may occur for numerous reasons, including events ranging from focal myocardial infarction to global ischemia of the myocardial tissue. Idiopathic dilated cardiomyopathy also may drive the evolution of functional mitral regurgitation. These disease states often lead to dilatation of the left ventricle. Such dilatation may cause papillary muscle displacement and/or dilatation of the valve annulus. As the papillary muscles move away from the valve annulus, the chordae connecting the muscles to the leaflets may become tethered. Such tethering may restrict the leaflets from closing together, either symmetrically or asymmetrically, depending on the relative degree of displacement between the papillary muscles. Moreover, as the annulus dilates in response to chamber enlargement and increased wall stress, increases in annular area and changes in annular shape may increase the degree of valve insufficiency. Annular dilatation is typically concentrated on the posterior aspect, since this aspect is directly associated with the expanding left ventricular free wall and not directly attached to the fibrous skeleton of the heart. Annular dilatation also may result in a flattening of the valve annulus from its normal saddle shape.

Alterations in functional capacity also may cause valve insufficiency. In a normally functioning heart, the mitral valve annulus contracts during systole to assist in leaflet coaptation. Reductions in annular contractility commonly observed in ischemic or idiopathic cardiomyopathy patients therefore hamper the closure of the valve. Further, in a normal heart, the papillary muscles contract during the heart cycle to assist in maintaining proper valve function. Reductions in or failure of the papillary muscle function also may contribute to valve regurgitation. This may be caused by infarction at or near the papillary muscle, ischemia, or other causes, such as idiopathic dilated cardiomyopathy, for example.

The degree of valve regurgitation may vary, especially in the case of functional insufficiency. In earlier stages of the disease, the valve may be able to compensate for geometric and/or functional changes in a resting state. However, under higher loading resulting from an increase in output requirement, the valve may become incompetent. Such incompetence may only appear during intense exercise, or alternatively may be induced by far less of an exertion, such as walking up a flight of stairs, for example.

Conventional techniques for managing mitral valve dysfunction include either surgical repair or replacement of the valve or medical management of the patient. Medical management typically applies only to early stages of mitral valve dysfunction, during which levels of regurgitation are relatively low. Such medical management tends to focus on volume reductions, such as diuresis, for example, or afterload reducers, such as vasodilators, for example.

Early attempts to surgically treat mitral valve dysfunction focused on replacement technologies. In many of these cases, the importance of preserving the native subvalvular apparatus was not fully appreciated and many patients often acquired ventricular dysfunction or failure following the surgery. Though later experience was more successful, significant limitations to valve replacement still exist. For instance, in the case of mechanical prostheses, lifelong therapy with powerful anticoagulants may be required to mitigate the thromboembolic potential of these devices. In the case of biologically derived devices, in particular those used as mitral valve replacements, the long-term durability may be limited. Mineralization induced valve failure is common within ten years, even in older patients. Thus, the use of such devices in younger patient groups is impractical.

Another commonly employed repair technique involves the use of annuloplasty rings. These rings originally were used to stabilize a complex valve repair. Now, they are more often used alone to improve mitral valve function. An annuloplasty ring has a diameter that is less than the diameter of the enlarged valve annulus. The ring is placed in the valve annulus and the tissue of the annulus sewn or otherwise secured to the ring. This causes a reduction in the annular circumference and an increase in the leaflet coaptation area. Such rings, however, generally flatten the natural saddle shape of the valve and hinder the natural contractility of the valve annulus. This may be true even when the rings have relatively high flexibility.

To further reduce the limitations of the therapies described above, purely surgical techniques for treating valve dysfunction have evolved. Among these surgical techniques is the Alfiere stitch or so-called bowtie repair. In this surgery, a suture is placed substantially centrally across the valve orifice between the posterior and anterior leaflets to create leaflet apposition. Another surgical technique includes application of the posterior annular space to reduce the cross-sectional area of the valve annulus. A limitation of each of these techniques is that they typically require opening the heart to gain direct access to the valve and the valve annulus. This generally necessitates the use of cardiopulmonary bypass, which may introduce additional morbidity and mortality to the surgical procedures. Additionally, for each of these procedures, it is very difficult, if not impossible, to evaluate the efficacy of the repair prior to the conclusion of the operation.

Due to these drawbacks, devising effective techniques that could improve valve function without the need for cardiopulmonary bypass and without requiring major remodeling of the valve may be advantageous. In particular, passive techniques to change the shape of the heart chamber and associated valve and/or reduce regurgitation while maintaining substantially normal leaflet motion may be desirable. Further, advantages may be obtained by a technique that reduces the overall time a patient is in surgery and under the influence of anesthesia. It also may be desirable to provide a technique for treating valve insufficiency that reduces the risk of bleeding associated with anticoagulation requirements of cardiopulmonary bypass. In addition, a technique that can be employed on a beating heart would allow the practitioner an opportunity to assess the efficacy of the treatment and potentially address any inadequacies without the need for additional bypass support.

SUMMARY OF THE INVENTION

A recently developed passive technique that addresses at least some of the drawbacks discussed above includes applying passive devices to the heart, for example the left ventricle, to change the shape of the ventricle and concomitantly to improve coaptation of the mitral valve leaflets. In one embodiment, the technique involves implanting splints across the left ventricle. Examples of various splinting approaches are disclosed in U.S. application Ser. No. 09/680, 435, filed Oct. 6, 2000, entitled "Methods and Devices for the Improvement of Mitral Valve Function," which is assigned to the same assignee as the present application and which is incorporated by reference in its entirety herein.

The devices and related methods which will be disclosed herein also operate passively to treat valve insufficiency, by altering the shape of the valve annulus and/or repositioning the papillary muscles, for example. Some of the devices of the present invention may be used in combination with the splinting treatments disclosed in U.S. application Ser. No. 09/680, 435, incorporated by reference herein.

It should be understood that the invention disclosed herein could be practiced without performing one or more of the objects and/or advantages described above. Other aspects will become apparent from the detailed description which follows. As embodied and broadly described herein, the invention includes a method for treating a heart valve comprising providing a device having an arcuate portion and at least one elongate portion configured to extend from the arcuate portion. The method may further comprise encircling at least a portion of an annulus of a heart valve with the arcuate portion and adjusting a size of at least one of the arcuate portion and the elongate portion so as to alter a shape of the portion of the annulus. The method also may include securing the at least one elongate portion to an exterior surface of the heart.

According to another aspect, a method of treating a heart valve comprises providing a device having an arcuate portion and at least one elongate member configured to extend from the arcuate portion. The method further comprises placing the arcuate portion proximate an annulus of a heart valve and extending the at least one elongate member from the arcuate portion. The method also may comprise securing the at least one elongate member to an exterior surface of the heart, wherein the at least one elongate member extends from the arcuate portion to the heart wall in substantially the same plane as the arcuate portion.

Yet another aspect includes a device for treating a heart valve comprising an arcuate portion configured to at least partly encircle an annulus of the heart valve and at least one elongate portion extending from the arcuate portion and configured to be secured to an exterior surface of a heart wall surrounding a heart chamber associated with the valve. At least one of the arcuate portion and the elongate portion is configured to be adjusted in size so as to alter a shape of at least a portion of the annulus.

In yet another aspect, a device for treating a heart valve comprises an arcuate portion configured to be positioned proximate an annulus of the heart valve and at least one elongate member extending from the arcuate portion and configured to be secured to an exterior surface of the heart wall. The at least one elongate member extends from the arcuate portion to the heart wall in substantially the same plane as the arcuate portion.

According to yet another aspect, the invention includes a device for treating a heart valve comprising at least one substantially elongate member configured to be implanted in a lumen of a coronary vessel so as to encircle at least a portion of an annulus of the heart valve and alter a shape of at least the portion of the annulus. The device may further comprise a shape change element associated with the elongate member and configured to impart a local shape change to a portion of the valve annulus at a location corresponding to the shape change element.

Yet another aspect includes a device for treating a heart valve comprising at least one substantially elongate member configured to be implanted in a lumen of a coronary vessel so as to encircle at least a portion of an annulus of the heart valve and alter a shape of at least the portion of the valve annulus. The shape of at least a portion of the elongate member may be configured to be adjustable so as to impart a local shape change to a portion of the valve annulus at a location corresponding to at least the adjustable portion.

Yet another aspect of the invention includes a method for treating a heart valve comprising providing at least one substantially elongate member and extending at least a portion of the elongate member within a heart wall surrounding a chamber of the heart associated with the heart valve so as to encircle at least a portion of the heart chamber. The method may further comprise securing the elongate member in place with respect to the heart and compressing at least a portion of a heart wall surrounding at least the portion of the heart chamber so as to move leaflets of the valve toward each other so as to assist the valve in closing during at least a portion of the cardiac cycle.

In yet another aspect, a method for treating a heart valve comprises providing at least one substantially elongate member and extending at least a portion of the elongate member within a lumen of a coronary sinus so as to encircle at least a portion of a heart chamber. The method further comprises securing the elongate member in place with respect to the heart via securement mechanisms and compressing at least a portion of a heart wall surrounding the portion of the heart chamber so as to move leaflets of the valve toward each other so as to assist the valve in closing during at least a portion of the cardiac cycle.

Yet another aspect of the invention includes a device for treating a heart valve comprising an elongate member having first and second oppositely disposed ends, with the elongate member being relatively rigid, a first anchoring member configured to be attached to the first end of the elongate member, and a second anchoring member configured to be attached to the second end of the elongate member. The first anchoring member may be configured to engage a first exterior surface of a wall of the heart and the second anchoring member may be configured to engage a second exterior surface of the wall of the heart to maintain a position of the elongate member transverse a heart chamber associated with the valve and substantially along a line of coaptation of the valve. The length of the elongate member may be such that the elongate member is capable of maintaining a substantially normal distance between trigones of the valve.

In yet another aspect, a method for treating a heart valve comprises providing a relatively rigid elongate member having first and second oppositely disposed ends, securing the first end of the elongate member to a first exterior heart wall surface, and securing the second end of the elongate member to a second exterior heart wall surface, the second exterior surface being located substantially opposite to the first exterior surface such that the elongate member extends substantially transverse a heart chamber associated with the valve and substantially along a line of coaptation of the valve. The method also may comprise maintaining a substantially normal distance between the trigones of the valve via the elongate member.

Yet another aspect of the invention includes a device for treating leakage of a heart valve comprising an expandable plug member having an external surface, with at least a portion of the plug member being configured to be positioned proximate leaflets of the heart valve. The device also may comprise a securement mechanism attached to the plug member and configured to secure the plug member with respect to the heart such that during at least a portion of the cardiac cycle, the leaflets abut the external surface of the plug member to restrict bloodflow through the valve.

According to another aspect, a device for treating leakage of a heart valve comprises a plug member having a piston-like configuration and an external surface being configured to abut free ends of leaflets of the valve to restrict bloodflow through the valve during at least the portion of the cardiac cycle. The device may further comprise a securement mechanism attached to the plug member and configured to secure the plug member with respect to the heart.

Yet another aspect of the invention includes a method of preventing leakage in a heart valve comprising providing an expandable plug member having an external surface, delivering the plug member to a heart chamber containing a valve, and positioning the plug member proximate leaflets of the valve such that the leaflets contact the external surface of the plug member during at least a portion of the cardiac cycle so as to restrict bloodflow through the valve.

BRIEF DESCRIPTION OF THE DRAWINGS

The accompanying drawings, which are incorporated in and constitute a part of this specification, illustrate several embodiments of the invention and together with the description, serve to explain certain principles. In the drawings.

FIG. 4c is a perspective view of yet another exemplary embodiment of a curved frame member implanted in a coronary sinus according to an aspect of the invention;

FIG. 4d is a perspective view of yet another exemplary embodiment of a curved frame member for implantation in a coronary sinus according to an optional aspect of the invention;

FIG. 4e is a perspective view of yet another exemplary embodiment of a curved frame member for implantation in a coronary sinus according to an aspect of the invention;

FIG. 11f is an exemplary embodiment of an inflatable sheet-like plug device configured to be implanted in the valve orifice between the valve leaflets according to an aspect of the invention;

FIG. 11g(i) is a perspective view of an exemplary embodiment of collapsible tube plug device in its expanded configuration according to an aspect of the invention;

FIG. 11g(ii) is a perspective view of the collapsible tube plug device of FIG. 11g (i) in its collapsed configuration according to an aspect of the invention;

FIG. 11h(i) is another exemplary embodiment of a collapsible plug device in its expanded configuration implanted in the valve according to an aspect of the invention;

FIG. 11h(ii) shows the collapsible plug device of FIG. 11h(i) in its collapsed configuration implanted in the valve according to an aspect of the invention;

FIG. 11i(i) is yet another exemplary embodiment of a collapsible plug device in its expanded configuration implanted in the valve according to an aspect of the invention;

FIG. 11i(ii) shows the collapsible plug device of FIG. 11i(i) in its collapsed configuration implanted in the valve according to an aspect of the invention;

FIG. 11j (i) is yet another exemplary embodiment of a collapsible plug device in its expanded configuration implanted in the valve according to an aspect of the invention;

FIG. 11j(ii) shows the collapsible plug device of FIG. 11j(i) in its collapsed configuration implanted in the valve according to an aspect of the invention;

FIG. 11k is an exemplary embodiment of a piston-like plug device implanted in the valve according to an aspect of the invention;

FIG. 11l(i) is another exemplary embodiment of a piston-like plug device shown in a collapsed configuration implanted in the valve according to an aspect of the invention;

FIG. 11l(ii) shows the piston-like plug device of FIG. 11l(i) shown in an expanded configuration implanted in the valve according to an aspect of the invention;

FIG. 11m(i) is yet another exemplary embodiment of a plug device shown implanted in the heart during systole according to an aspect of the invention;

FIG. 11m(ii) shows the plug device of FIG. 11m(i) shown implanted in the heart during diastole according to an aspect of the invention;

FIG. 15c is a perspective view of the trocar and needle assembly of FIG. 15a with an exemplary embodiment of plug member advanced out of the trocar and needle assembly according to an aspect of the invention;

FIG. 16a is a perspective view of an exemplary embodiment of a plug device with a plug member in a folded configuration according to an aspect of the invention;

DESCRIPTION OF THE PREFERRED EMBODIMENTS

Figure 1A:
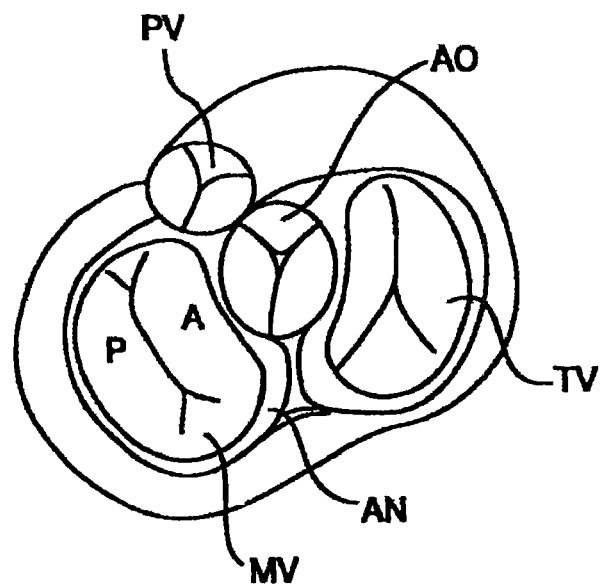
FIG. 1a is a short-axis cross-sectional view of the heart.

Certain aspects of the invention that will be discussed herein generally pertain to devices and methods for treating valve insufficiency arising from heart conditions, including, for example, ventricle dilatation, valve incompetencies, congenital defects, and other conditions. The various devices to be described may operate passively in that, once implanted in the heart, they do not require an active stimulus, either mechanical, electrical, or otherwise, to function. Implanting one or more of the devices of the present invention may assist in closing a valve to prevent regurgitation by, for example, assisting in the proper coaptation of the heart valve leaflets, either against one another or independently against another surface. Assisting this coaptation may be accomplished by directly geometrically altering the shape of the dysfunctional mitral valve annulus, by repositioning one or both of the papillary muscles to a more normal state, and/or by otherwise facilitating annular contraction during systole. In addition, these devices may be placed in conjunction with other devices that, or may themselves function to, alter the shape or geometry of one or more heart ventricles, locally and/or globally, and thereby further increase the heart's efficiency. That is, the heart may experience an increased pumping efficiency and concomitant reduction in stress on the heart walls through an alteration in the shape or geometry of one or more of the ventricles and through an improvement in valve function.

The inventive devices and related methods may offer numerous advantages over the existing treatments for various valve insufficiencies. The devices are relatively easy to manufacture and use, and the surgical techniques and tools for implanting the devices of the present invention do not require the invasive procedures of current surgical techniques. For instance, the surgical techniques do not require removing portions of the heart tissue, nor do they necessarily require opening the heart chamber or stopping the heart during operation. All of the techniques described may be performed without placing the patient on cardiopulmonary bypass, which, as discussed above, is routinely required for conventional procedures to repair and/or replace the mitral valve. Avoiding placing the patient on cardiopulmonary bypass may permit the inventive devices and related methods to be adjusted "real time" so as to optimize the performance of the valve. Furthermore, the inventive devices and related methods may avoid the need to place the patient on long-term anticoagulation, which currently is required for many current valve repair techniques. For these reasons, the surgical techniques for implanting the devices of the present invention also are less risky to the patient than other techniques. The less invasive nature of the surgical techniques and tools of the present invention may also allow for earlier intervention in patients with heart failure and/or valve incompetencies.

Although many of the methods and devices are discussed below in connection with their use in the left ventricle and for the mitral valve of the heart, these methods and devices may be used in other chambers and for other valves of the heart for similar purposes. The left ventricle and the mitral valve have been selected for illustrative purposes because a large number of the disorders that the present invention treats occur in connection with the mitral valve. Furthermore, as will be shown, certain devices disclosed herein for improving valve function can be used either as stand-alone devices (i.e., solely for treatment of valve insufficiency) or in conjunction with other devices for changing the shape of a heart chamber or otherwise reducing heart wall stress.

Reference will now be made in detail to some optional embodiments of the invention, examples of which are illustrated in the accompanying drawings. Wherever possible, the same reference numbers will be used throughout the drawings to refer to the same or like parts.

Figure 1B:
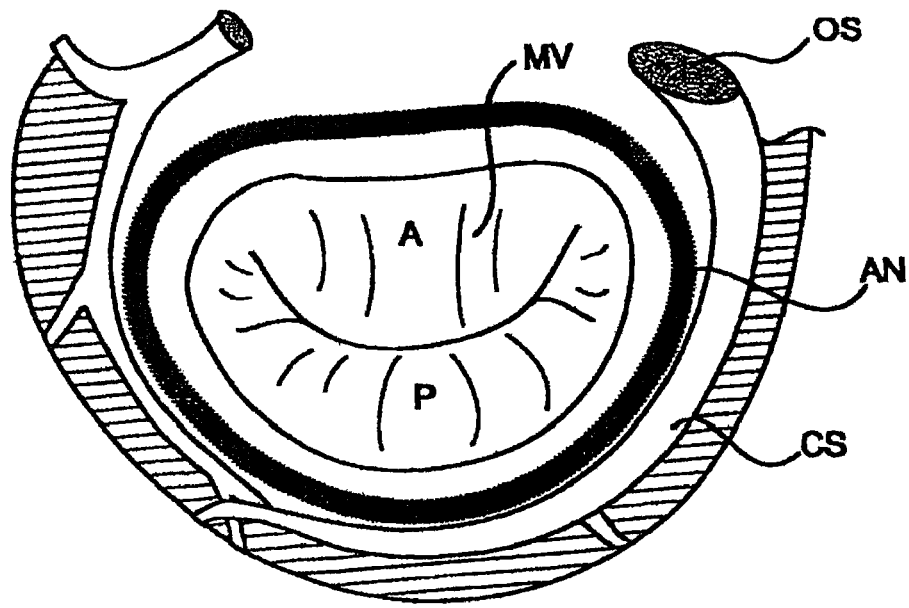
FIG. 1b is a partial short axis cross-sectional view of the heart.

FIG. 1a is a short-axis cross-sectional view of the heart illustrating the mitral valve MV in relation to the other valves of the heart, namely, the aortic valve AO, the tricuspid valve TV, and the pulmonary valve PV. The mitral valve has two leaflets, an anterior leaflet A and a posterior leaflet P. The anterior leaflet A is adjacent the aorta, AO, and the posterior leaflet P is opposite the aorta AO. An annulus AN surrounds the mitral valve leaflets. FIG. 1b is a partial short-axis cross-sectional view showing the mitral valve MV in relation to the coronary sinus CS. The coronary sinus CS wraps around a significant portion of the posterior aspect of the mitral valve annulus AN. The ostium OS of the coronary sinus CS drains into the right atrium RA.

Figure 2A:
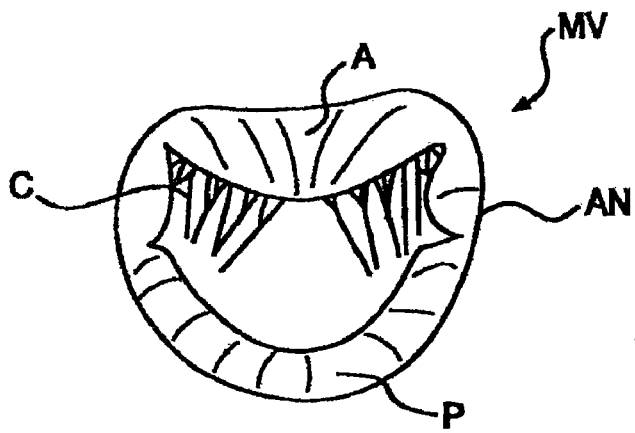
FIG. 2a is a top view of a properly functioning mitral valve in an open position.
Figure 2B:
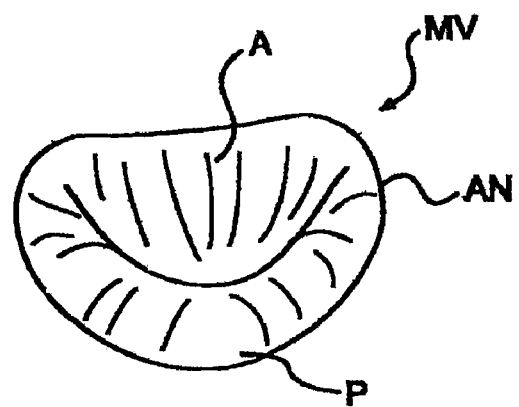
FIG. 2b is a top view of a properly functioning mitral valve in a closed position.

In FIGS. 2a and 2b, a top view of a properly functioning mitral valve MV is shown. FIG. 2a shows the valve MV in its open position during diastole in which the posterior leaflet P is separated from the anterior leaflet A. Portions of the chordae C also can be seen in FIG. 2a. FIG. 2b shows the properly functioning mitral valve MV in the closed position during systole. In this figure, the anterior leaflet A and the posterior leaflet P contact one another along a line of coaptation to close the mitral valve MV and prevent blood from flowing through the valve MV from the left atrium to the left ventricle.

Figure 2C:
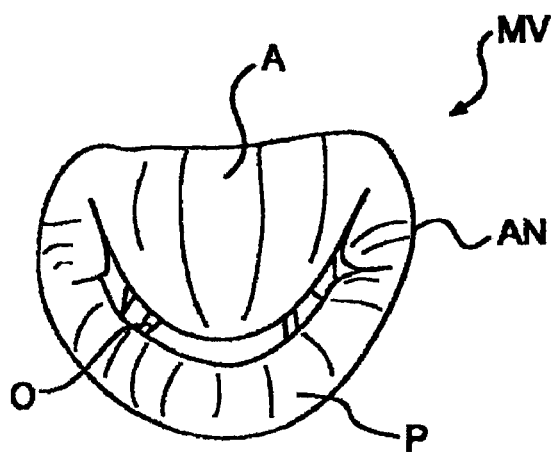
FIG. 2c is a top view of an improperly functioning mitral valve in a "closed" position.

FIG. 2c shows a top view of an improperly functioning mitral valve MV in the "closed" position (i.e., during systole). In FIG. 2c, the anterior leaflet A and the posterior leaflet P do not properly co-apt when the valve MV is in the closed position. This may be caused by, for example, a dilatation of the annulus AN caused by an enlargement of the left ventricle, or other similar mechanisms discussed above. As shown in FIG. 2c, this improper coaptation prevents the complete closure of the orifice O between the valve leaflets, thereby permitting blood to leak through the valve from the left ventricle to the left atrium during systole. In other words, although the mitral valve is in a contracted state, it is not actually closed so as to prevent blood flow therethrough since the leaflets are prevented from completely coming together.

Figure 3A:
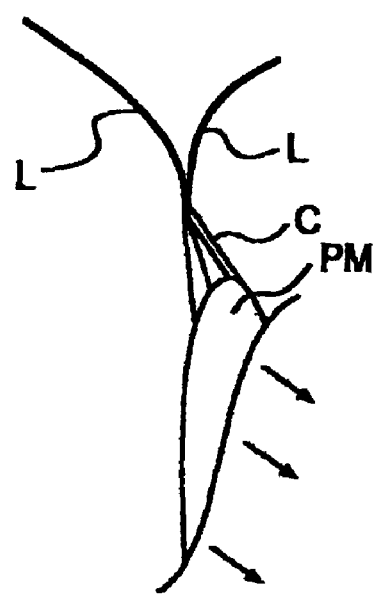
FIG. 3a is a side view of a properly functioning mitral valve shown with its connection to the papillary muscles.
Figure 3B:
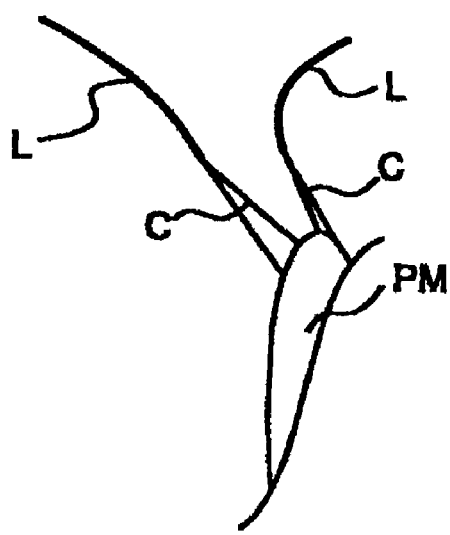
FIG. 3b is a side view of an improperly functioning mitral valve shown with its connection to the papillary muscles.

FIG. 3a shows a side view of a properly functioning mitral valve in the closed position with the valve leaflets L properly coapted so as to prevent blood flow through the valve. FIG. 3b shows a side view of an improperly functioning mitral valve in which the valve leaflets L are not properly coapted due to, for example, dislocation of the papillary muscles PM. Such dislocation of the papillary muscles also may be caused by enlargement of the left ventricle, for example. The arrows in FIG. 3a show the movement of the papillary muscles PM down and to the right resulting from such ventricle dilatation.

Such dysfunctioning valves, as shown in FIGS. 2c and 3b, may cause a reduction in forward stroke volume from the left ventricle. Also, a blood flow reversal into the pulmonary veins may occur. Mitral valve regurgitation may also arise from a combination of valve annulus dilation and papillary muscle dislocation.

It should be noted that dilatation of the left ventricle represents an example of a condition that can lead to improper valve function. Other conditions, discussed above, also may cause such valve dysfunction, and the devices and techniques discussed herein can be used to treat valve insufficiencies caused by these conditions.

Exemplary embodiments of a device for treating the mitral valve via a change in shape of the valve annulus, which may include a reduction in the effective circumference of the valve annulus, are shown in FIGS. 4a-4i. The devices of FIGS. 4a-4i may be implanted on a beating heart, without the need for cardiopulmonary bypass. The devices of FIGS. 4a-4i comprise curved frame members configured to be inserted into the coronary sinus to effect a shape change of the posterior aspect of the mitral valve annulus. In certain embodiments, as will be discussed, the frame members include mechanisms that allow for creating a focused shape change at selected locations along a portion of the mitral valve annulus adjacent the frame members. That is, the frame members may allow for differing shape change effects along the length of the frame member. The ability to selectively alter the shape in one region of the annulus differently than another region may be particularly advantageous when treating patients whose mitral valve insufficiency has arisen from local myocardial ischemia or infarction, since such patients may experience relatively localized geometrical alterations of the mitral valve annulus, as opposed to an overall radial increase of the annulus.

Figure 4A:
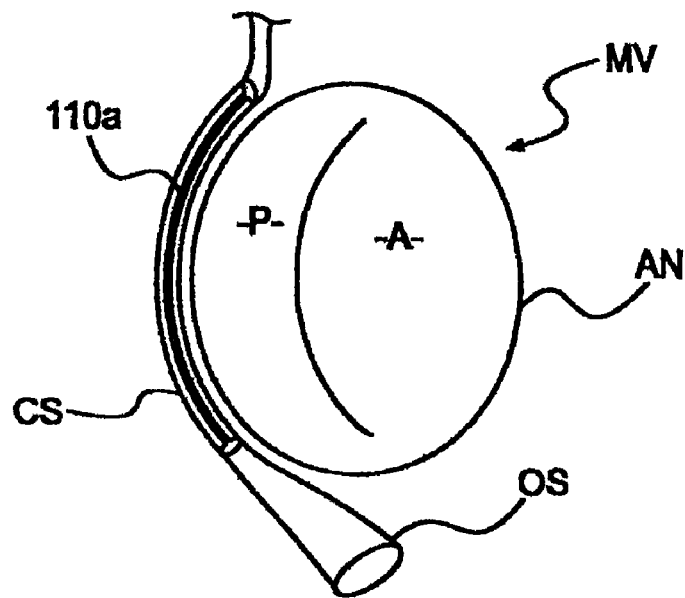
FIG. 4a is a cross-sectional view of a mitral valve and a coronary sinus with an exemplary embodiment of a curved frame member implanted in the coronary sinus according to an aspect of the invention.

As shown in FIG. 4a, a curved frame member 110a is configured to be delivered endovascularly to and implanted in the coronary sinus CS. The origin of the coronary sinus CS is located in the wall of the right atrium (not shown), and may be accessed by, for example, catheterization of the femoral, jugular, or subclavian veins, so as to endovascularly implant the frame member 110a. Alternatively, the frame member 110a could be implanted via a surgical approach. In any case, the frame member 110a may be positioned in the coronary sinus CS proximate the posterior aspect of the mitral valve annulus, as shown in FIG. 4a. In this position, the frame 110a may be used to alter the shape of the posterior aspect of the valve annulus, creating a configuration that effectively reduces the annular circumference and/or creates a greater degree of coaptation between the anterior and posterior leaflets A, P. Alternatively, the frame member 110a may be used to stabilize the shape of the posterior aspect of the valve annulus, thereby substantially preventing continued dilation or deformation of the valve annulus.

The frame member 110a may be made of a substantially rigid material such that the frame member 110a can be bent or otherwise formed into the desired shape and placed within the coronary sinus CS, causing the annulus of the mitral valve MV, or portions thereof, to change shape. The frame member 110a may engage within the coronary sinus CS via a friction fit to maintain its position within the coronary sinus CS. A further alternative is to fabricate the frame member 110a of a shape memory material, such as nickel-titanium alloy, for example. In this manner, the frame member 110a may be chilled prior to implantation such that it has some flexibility. This may permit the frame member 110a to be introduced into the coronary sinus CS in a relatively atraumatic manner. Once in place, the blood may warm the frame member 110a, causing a shape change to a preformed initial shape. This shape change of the frame member 110a may in turn alter the shape of the coronary sinus CS and thus the valve annulus.

Figure 4B:
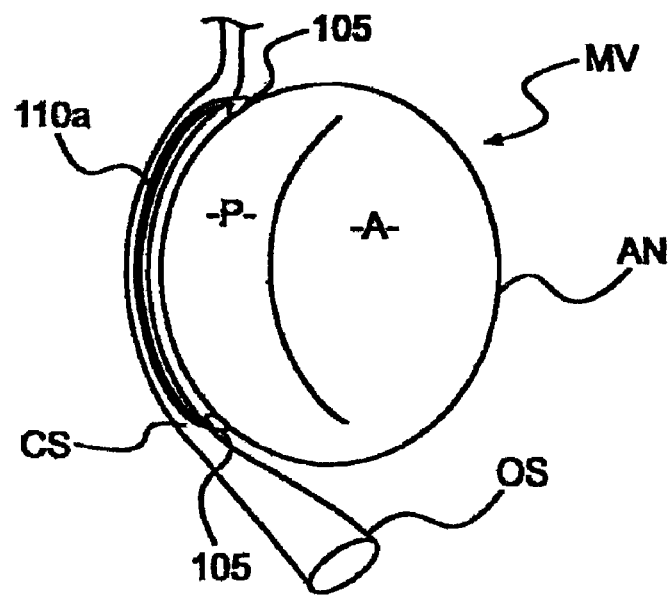
FIG. 4b is a cross-sectional view of another exemplary embodiment of a curved frame member implanted in a coronary sinus according to an aspect of the invention.

As shown in FIG. 4b, one or both ends of the frame member 110a may exit the coronary sinus CS and anchor assemblies 105 may be provided on the ends of the frame member 110a. This may allow the frame member 110a to impart a shape change to the valve annulus beyond the somewhat limited extent of the coronary sinus CS around the posterior aspect of the valve. The frame member 110a may be anchored to an exterior surface of the heart wall via the anchor assemblies 105. The ends of the frame member 110a may puncture through the coronary sinus CS to pass externally and allow connection of the anchor assemblies 105 to the exterior surface of the heart. The anchor assemblies 105 may be in the form of anchor pads. Some examples of such anchor pads are described in U.S. application Ser. No. 09/680,435, incorporated above. The anchor assemblies 105 may be sutured, or secured by other similar attachment mechanisms, such as by providing a surface of the anchor assemblies 105 with a tissue ingrowth promoting material, to an exterior surface of the heart wall to hold the frame 110a in place with respect thereto. To further facilitate obtaining the desired shape change of the mitral valve annulus, the anchor assemblies 105 may be positionable along the length of the frame member 110 prior to fixation of the frame member 110 with respect to the heart or the frame member 110 may have a variable length. For example, the frame member 110a may be provided with a telescoping mechanism or the like.

In yet another exemplary embodiment, as shown in FIG. 4c, the frame member 110c may be configured to anchor itself into the vessel wall in order to maintain its position. For example, in the optional configuration shown in FIG. 4c, the frame member 110c is provided with barbs 111 along its length. The frame member 110c may be delivered endovascularly such that the barbs 111 do not engage the wall of the coronary sinus CS. Once the frame member 110c is placed within the coronary sinus CS in the desired position, it may be manipulated, for example, by rotation or by moving the frame member 110c in a direction opposite to the direction of advancement through the coronary sinus CS, so as to engage the barbs 111 with the coronary sinus wall. This engagement helps to maintain the position of the frame member 110c.

FIG. 4d shows another embodiment of a curved frame member 110d configured to be implanted in the coronary sinus CS for treating the mitral valve. In this embodiment, the frame member 110d may support a shape change element 106 configured to move along a length of the frame member 110d. The shape change element 106 may be configured to protrude radially with respect to the frame 110d, thereby providing a more localized shape change in an area along the posterior aspect of the mitral valve. A desired location for the shape change may be determined by moving the shape change element 106 along the length of the frame member 110d to a particular position and viewing the effects on mitral valve function through real-time imaging techniques. The shape change element 106 also may be detachable from the frame member 110d for easy removal from the frame member 110d if the localized shape change is no longer desired. The shape change element 101 may be mechanically detachable or it may be detached electrolytically in a manner similar to the detachment mechanism of the Guglielmi detachable coil. A delivery tool, which may be in the form of a delivery wire 106', may be used to deliver the shape change element 101 over the frame member 110d.

FIG. 4e shows another exemplary embodiment of a curved frame for insertion into the coronary sinus proximate the posterior aspect of the mitral valve. In this embodiment, the frame member 110e serves as a support for an adjustable shape change member 107. As an example, the curved frame 110e may define at least one slot 108 extending along at least part of the length of the frame 110e. A moveable pin 109 may engage with the slot 108 so as to slide along the length of the slot 108. A wire 112 may extend along the portion of the curved frame 110e that lies adjacent the posterior aspect of the mitral valve annulus. The wire 112 may have one end attached to the pin 109 and an opposite end attached at an end of the frame 110e substantially opposite to the moveable pin 109. For example, as shown in FIG. 4e, the wire 112 may be attached to a fixed pin 109'. Alternatively, the wire may attach directly to the frame member 110e. Upon movement of the pin 109 toward a center of the frame member 110e, the wire 112 curves, forming a bulge that causes the mitral valve annulus to change shape.

The frame member 110e optionally may have two pins disposed at opposite ends of the frame in either a single slot running substantially the entire length of the frame 110e or two different slots disposed at substantially opposite ends of the frame 110e. In an exemplary embodiment, both of the pins 109, 109' shown in FIG. 4e, may be moveable. In either case, the movement of one pin or both pins may cause the wire 112 to bulge outward, thereby imparting a variable degree of shape change to the mitral valve annulus. Preferably, the wire 112 is sufficiently flexible so as to permit bending of the wire due to the movement of the pin 109 within the slot 108. However, the wire 112 also should be sufficiently rigid so as to maintain its bulged configuration and cause the desired shape change and/or repositioning of the valve annulus and/or papillary muscles.

Figure 4F:
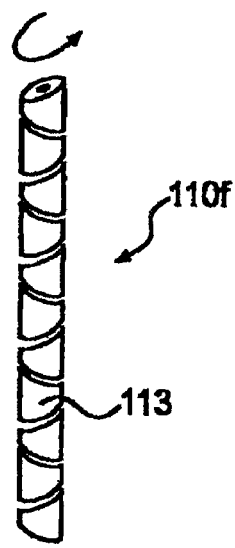
FIG. 4f is a perspective view of yet another embodiment of a curved frame member for implantation in a coronary sinus according to an aspect of the invention.
Figure 4G:
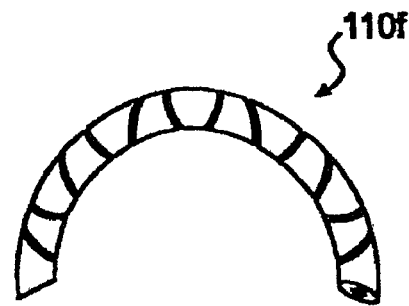
FIG. 4g is a perspective view of the curved frame member of FIG. 4f in a curved configuration.

FIGS. 4f and 4g illustrate yet another exemplary embodiment of a curved frame member 110f for implanting in the coronary sinus to alter the shape of the mitral valve annulus. FIG. 4f is a perspective view of the frame member 110f, which is formed from segments 113 configured to rotate relative to each other. Rotating the segments 113 about their respective longitudinal axes and relative to each other may alter the curvature of the frame 110f along its length so as to produce various degrees of curvature in particular locations as desired. Such curvature of the frame member 110f is illustrated in FIG. 4g. As a direct surgical implant, the curved frame member 110f can have its segments 113 individually manipulated via direct rotation to achieve a desired final shape prior to insertion into the coronary sinus CS. A wire (not shown) extending down the center of the segments 113 may hold the segments 113 in their final desired configuration, for example, due to frictional engagement.

Figure 4H:
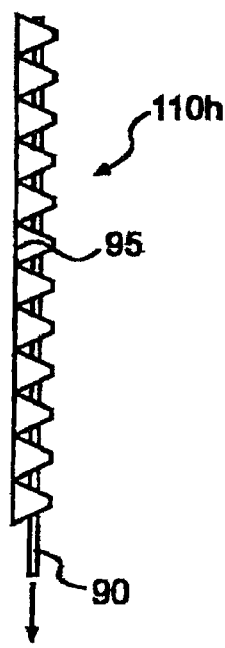
FIG. 4h is a perspective view of yet another exemplary embodiment of a curved frame member according to an aspect of the invention.
Figure 4I:
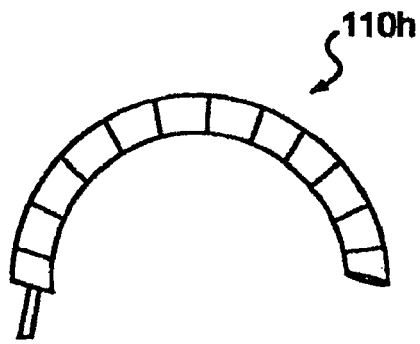
FIG. 4i is a perspective view of the curved frame member of FIG. 4h in a curved configuration.

In another contemplated embodiment, shown in FIGS. 4h and 4i, a curved frame member 110h may comprise an actuation mechanism 90 attached to a portion of the frame member 110h. For example, the actuation mechanism 90 may be attached to a distal end of the frame member 110h. The frame member 110h may be formed of a plurality of substantially wedge-shaped segments 95. Actuating the actuation mechanism 90, by, for example, pulling mechanism 90 proximally, causes the distal end to retract so as to change the shape of the frame member 110h, as shown in FIG. 4i. This in turn may alter the shape of the mitral valve annulus when the frame member 110h is implanted in the coronary sinus CS. The actuation mechanism 90 may comprise a pull-actuated wire attached to a distal end of the frame member, as shown in FIGS. 4h and 4i, or alternatively to an anchor assembly provided on the distal end of the frame member. The desired final shape of the frame member 110h may reduce or enlarge a radius of curvature of the valve annulus, or a combination of both, i.e., increasing the curvature in some regions and decreasing the curvature in other regions.

The various curved frame devices of FIGS. 4a-4i may be configured to be implanted on a beating heart. Optionally, the frame devices may be implanted during an open chest or minimally invasive thoracic surgical procedure. For example, the frame member may be directly inserted into the coronary sinus through an incision in either the right atrium or the coronary sinus. In an alternative exemplary embodiment, the frame devices could be implanted endovascularly into the coronary sinus using catheter-based delivery techniques. For example, a catheter may be inserted into either the jugular vein or the vena cava and into the right atrium and then the coronary sinus.

FIGS. 5a-5e show an exemplary embodiment of a floating ring device for treating mitral valve dysfunction by altering the shape of the mitral valve annulus. The floating ring device according to the invention may be implanted into the region of the mitral valve annulus itself (either above, at, or below the annulus) in order to effect the desired shape change of the mitral valve annulus.

Figure 5A:
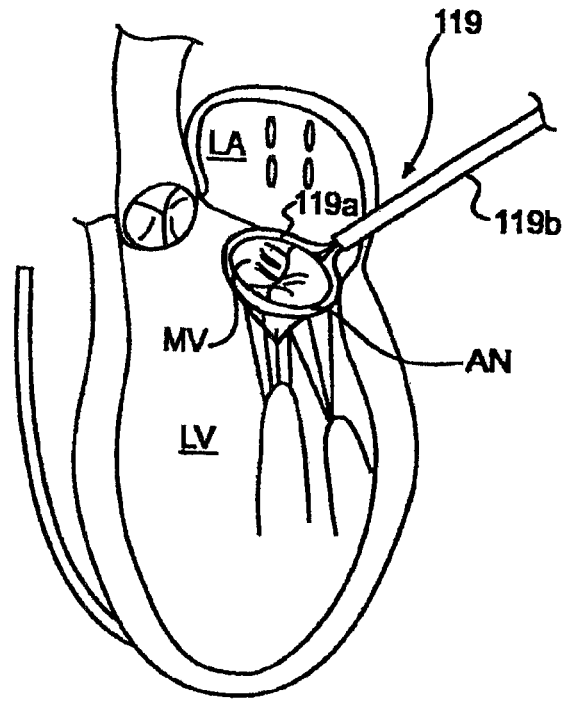
FIG. 5a is a long axis, partial, cross-sectional view of a heart with a snare device delivered to the mitral valve according to an exemplary embodiment of the invention.
Figure 5B:
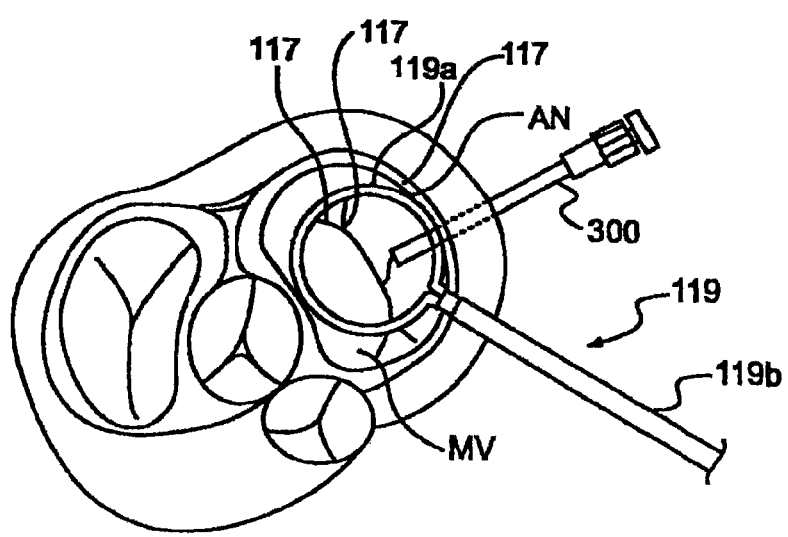
FIG. 5b is a short axis, cross-sectional view of a heart with filaments delivered to the mitral valve and captured by the snare device of FIG. 5a according to an exemplary embodiment of the invention.
Figure 5C:
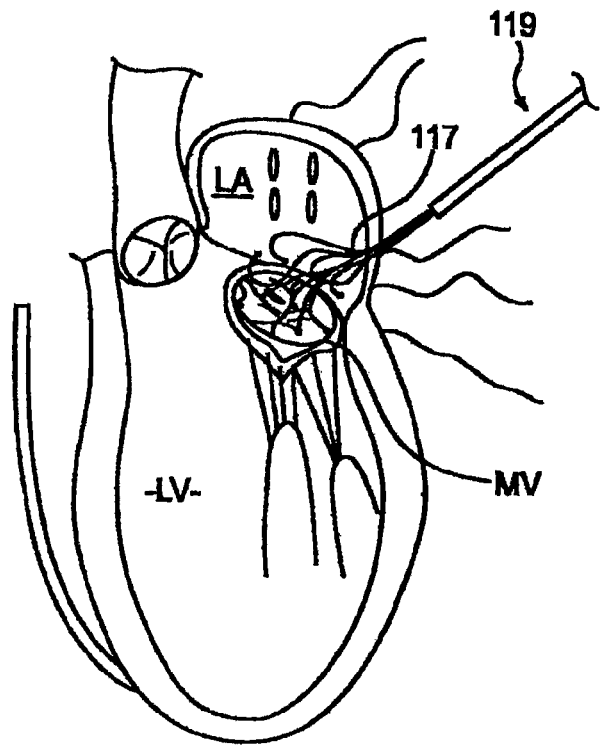
FIG. 5c is a long axis, partial, cross-sectional view of a heart with the filaments of FIG. 5b drawn through the left atrium by the snare device according to an exemplary embodiment of the invention.
Figure 5D:
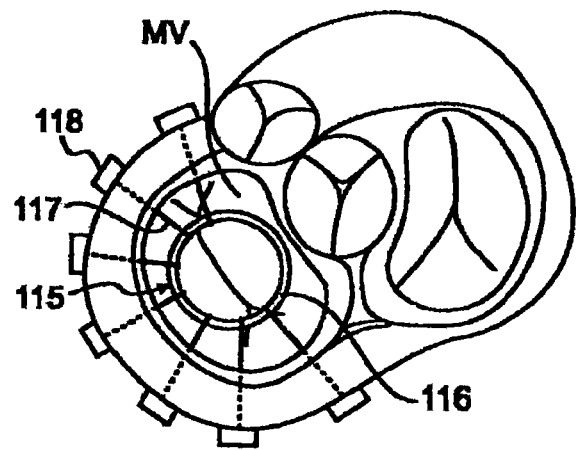
FIG. 5d is a short axis, cross-sectional view of a heart showing an embodiment of a floating ring device implanted to treat the mitral valve according to an optional aspect of the invention.

A short axis cross-sectional view of the heart implanted with an exemplary embodiment of a floating ring device 115 is shown in FIG. 5d. The device comprises a semi-flexible ring 116 configured to be placed in the left atrium LA, proximate the mitral valve annulus. A plurality of tightening members 117, which may have the form of tension members, are secured to the ring 116. An anchor mechanism, for example in the form of a pad 118, attaches to the free end of each tightening member 117 opposite to the ring 116. The anchor pads 118 are adapted to be secured to the tightening members 117 and placed externally of the heart wall, for example on the posterior wall of the left atrium LA, to secure the floating ring device 115 in place with respect to the heart. Prior to securing the anchor pads 118 to the tightening members 117, the tightening members 117 may be tightened (i.e., their lengths between the valve annulus and heart wall altered) until the desired annular shape of the mitral valve is obtained. The tightening members 117 may be individually tightened to produce differing effects on the shape of the mitral valve annulus depending on the position around the annulus. The flexibility of the ring 116 also may assist in producing a varying effect on the mital valve annulus geometry. It is contemplated that sutures or other attachment mechanisms may be employed instead of the anchor pads 118 to secure the tightening members 117 to the heart wall once the desired tensioning of the tightening members 117 has been achieved.

Referring to FIGS. 5a-5d, an exemplary delivery technique for implanting a floating ring device will be described. The technique described preferably is performed on a beating heart. As shown in FIG. 5a, a snare 119 is first delivered through a relatively small incision in the wall of the appendage of the left atrium LA. As an example, the incision may be made at a location superior to the mitral valve MV. A trocar (not shown) also may assist in the delivery of the snare 119 through the incision. The snare 119 comprises a loop portion 119a at a distal end of the device and a handling portion 119b extending from the loop portion 119a. The handling portion 119b forms a proximal end of the snare 119. The handling portion 119b may extend out of the left atrium upon deployment of the snare 119 within the heart. According to an alternative aspect, the snare 119 may be delivered through the venous system to the right atrium (not shown) and then into the left atrium LA via the atrial septum. In either case, once the snare 119 is delivered into the left atrium LA, the loop portion 119a may be positioned with its perimeter resting on substantially the outermost edges of the mitral valve annulus AN.

After appropriately positioning the snare 119 with respect to the mitral valve annulus AN, a plurality of tightening members 117, which may have a substantially filament-like structure, may be inserted from external the heart, through the wall of the left atrium LA, and into the left atrial chamber. For example, as shown in FIG. 5b, a hollow, needle-like delivery tool 300 may be used to insert the tightening members 117 through the heart wall by inserting the delivery tool 300 carrying the tightening members 117 through the heart wall and ejecting the members 117 out of the delivery tool 300.

As shown in FIG. 5b, the tightening members 117 may be positioned along the posterior aspect of the mitral valve MV approximately at the level of the mital valve annulus AN. As the tightening members 117 are inserted into the atrial chamber, they may be carried through the snare loop 119a via the blood flowing from the left atrium LA through the mitral valve MV and to the left ventride LV. To facilitate delivery of the tightening members 117; especially with regard to their insertion through the heart wall, the tightening members 117 optionally may be attached to needles which penetrate the heart wall first. In this case, the bloodflow would carry the needles with the tightening members 117 attached from the left atrium LA and through the snare loop portion 119a.

Once the tightening members 117 have been drawn through the snare loop portion 119a, the snare 119 may then be retracted and the tightening members 117 captured within the loop portion 119a. By pulling proximally on the handling member 119b, the snare 119 with the captured tightening members 117 may be retrieved from the left atrium LA. As shown in FIG. 5c, the free ends of the tightening members 117 may be pulled out of the left atrium appendage through the incision previously made to insert the snare device 119. The snare device 119 may be removed from the tightening members 117 once they are pulled out of the left atrium LA.

The free ends of the tightening members 117 may then be secured to the flexible ring 116, for example, by tying the ends to the ring. The flexible ring 116 may then be reinserted into the left atrium LA by pulling on the tightening members 117 at their respective insertion points in the left atrial wall. Thus, the flexible ring 116 may be inserted through the same delivery path that was used to insert the snare 119.

The flexible ring 116 preferably has enough flexibility so as to permit insertion of the ring 116 into a trocar and/or an incision made in the left atrial appendage and through the left atrium LA. Furthermore, the ring 116 and the tightening members 117 preferably are covered with a hemocompatible material, such as expanded PTFE, for example. This covering may facilitate the endothelialization of any portion of the ring 116 and tightening members 117 residing in the blood flow path near the mitral valve.

After tightening each tightening member 117 to a desired amount, a securing mechanism, such as the anchor pads 118 shown in FIG. 5d, may secure the tightening members 117 externally to the heart wall. Depending on the position and number of tightening members 117, and the relative degree of tightening of each, various annular geometries of the mitral valve may be obtained. Echocardiographic visualization may be employed to assist in adjusting the floating ring device. For example, the device can be selectively tightened in various locations and/or to various degrees until minimal or no mitral valve regurgitation is observed using the echocardiographic visualization.

Figure 5E:
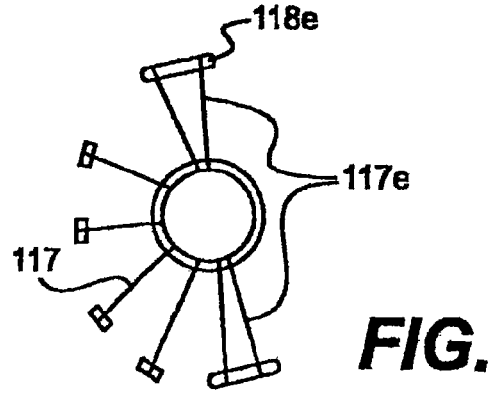
FIG. 5e is a perspective view of an exemplary embodiment of a floating ring device according to an aspect of the invention.

A further exemplary embodiment of a floating ring device is illustrated in FIG. 5e. In this embodiment, the anterior-most pairs of tightening members 117e are relatively rigid. A single elongate anchor pad 118e connects to the ends of each of the pairs of tightening members 117e. In this manner, the position of the ring 116 over the central portion of the mitral valve may be maintained, even as the posterior-oriented tightening members 117e are tightened.

Yet another optional embodiment of a device for treating the mitral valve is illustrated in FIGS. 6a-6d. The device shown in these figures is referred to herein as an "annular noose," so-named due to its noose-like configuration. The annular noose 120 is formed from a flexible rope-like member 121. The member 121 may be made of a braided polyester, or other similar material, that allows the member 121 to flex without forming kinks and/or permanent bends. The rope-like member 121 is shaped into a loop portion 122 that is placed around the exterior of the left atrium (not shown), as dose as possible to the atrioventricular groove (not shown), and in substantially the same plane as the mitral valve annulus AN. It may be necessary for the portion between the anterior leaflet and the aorta to be passed through the tissue of the left atrium. An adjusting mechanism manipulable from external the heart, such as a cinch ring 125, for example, may be used to adjust the size of the loop portion 122 and secure the free ends 123a, 123b of the member 121 that extend from the loop portion 122. After the loop portion 122 has been properly positioned with respect to the mitral valve annulus AN, the cinch ring 125 may be tightened, thereby permitting a reduction in the circumference of the mitral valve annulus AN.

Figure 6A:
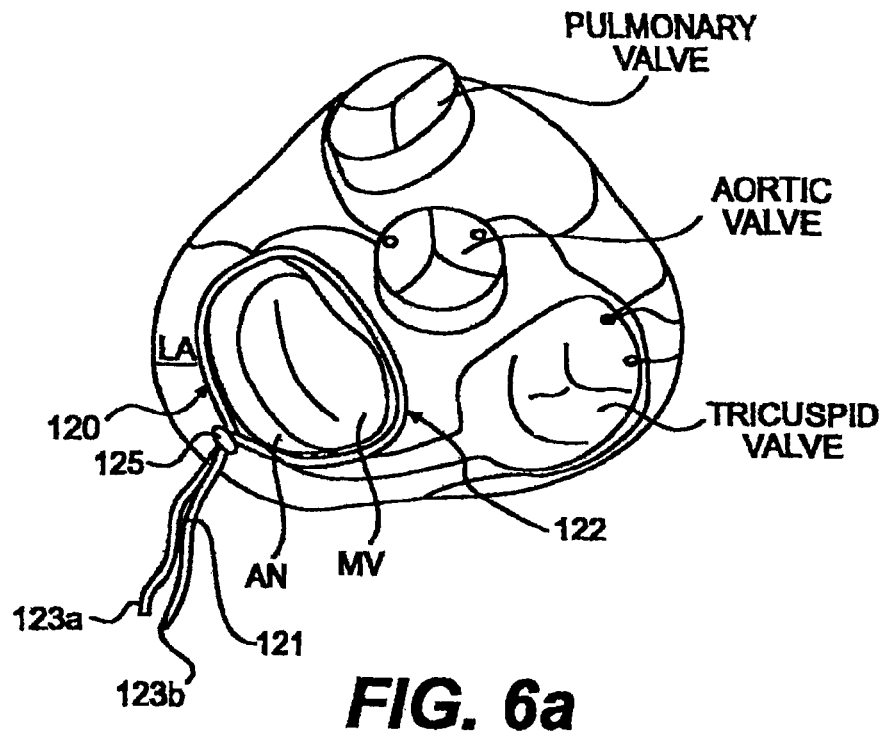
FIG. 6a is a short axis cross-sectional view of a heart showing an exemplary embodiment of an annular noose implanted to treat the mitral valve according to an aspect of the invention.
Figure 6B:
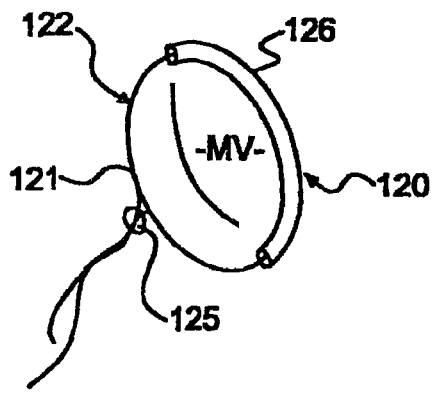
FIG. 6b is a cross-sectional view of a mitral valve with another exemplary embodiment of an annular noose implanted to treat the mitral valve according to an aspect of the invention.
Figure 6C:
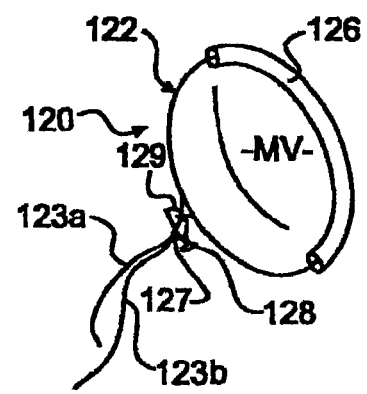
FIG. 6c is a cross-sectional view of a mitral valve with yet another exemplary embodiment of an annular noose implanted to treat the mitral valve according to an aspect of the invention.

FIGS. 6b and 6c show various elements that may be used in conjunction with the annular noose 120 of FIG. 6a so as to provide a more focused geometrical shape change in selected regions of the mitral valve. For example, as shown in both FIGS. 6b and 6c, a relatively rigid member 126 may be placed over the flexible member 121. In the optional embodiment shown in FIGS. 6b and 6c, the relatively rigid member 126 has a tubular configuration that may be advanced over either of the free ends of the flexible member 121 and positioned as desired along the loop portion 122. Alternatively, the relatively rigid member 126 may be permanently secured to the loop portion 122 of the flexible member 121. In the embodiment of FIG. 6b, the annular noose 120, with the relatively rigid member 126 disposed thereon, is positioned with respect to the mitral valve MV such that the relatively rigid member 126 rests by the anterior leaflet side of the mitral valve MV. This placement may permit a more focused circumferential reduction to take place at a location proximate the posterior leaflet, since this portion is more flexible and will tend to draw the noose down as it is tightened.

FIG. 6c shows another embodiment of an element for use in conjunction with the annular noose 120. A shape change securing pad 127 may be used for adjusting the size of the loop portion 122 and for securing the free ends 123a, 123b. As shown in FIG. 6c, the shape change pad 127 may have a substantially disk-like configuration with a central, substantially longitudinal passage through which the ends 123a, 123b of the flexible member 121 extend. A securing pin 128 may operate to move toward and away from the center of the pad to pass through the flexible members ends 123a, 123b and secure the annular noose 120 into position. A surface 129 of the pad 127 that faces the mitral valve annulus may have a substantially non-concave profile, for example the surface 129 may be either convex or flat. When the pad 127 is moved so as to tighten the annular noose 120, the pad 127 may press against the mitral valve annulus and thereby cause a relatively focused shape change in the region of the pad 127.

Figure 6D:
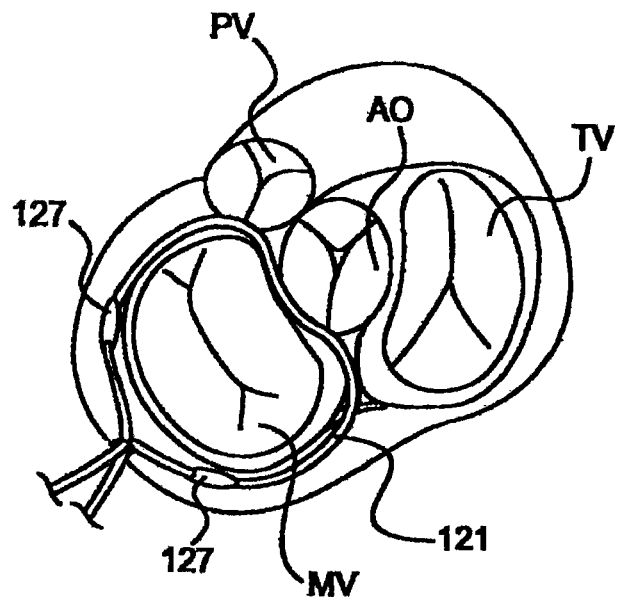
FIG. 6d is a short axis cross-sectional view of a heart with another exemplary embodiment of an annular noose implanted to treat the mitral valve according to an aspect of the invention.

As shown in FIG. 6d, a plurality of pads 127 may be used to change the shape of the mitral valve in the regions of the mitral valve proximate the pads. Such a focused change may permit increased co-aptation of the valve leaflets in the various regions of the focused shape change. The shape change pad 127 and the relatively rigid member 126 may be used either in combination, as shown in FIG. 6c, or individually to create a focused shape change of the mitral valve. Such a focused shape change is in addition to the overall circumferential reduction achieved by the annular noose 120 alone.

Figure 6E:
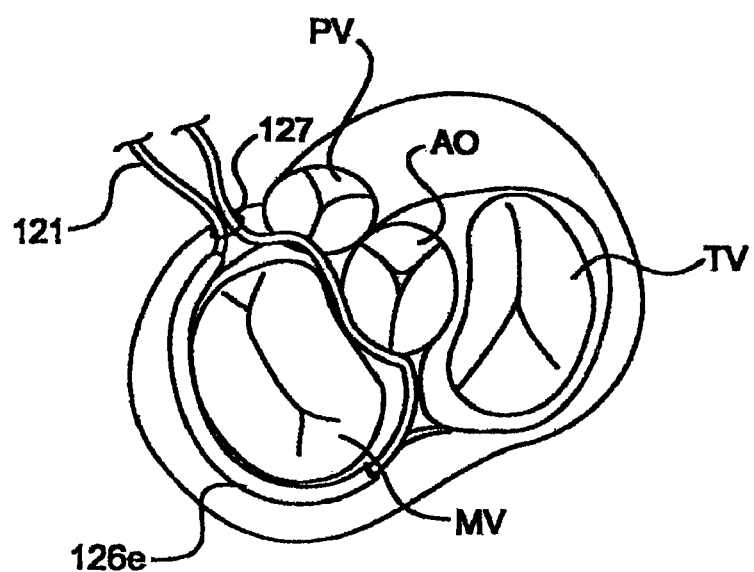
FIG. 6e is a short axis cross-sectional view of a heart with another exemplary embodiment of an annular noose according to an aspect of the invention.

FIG. 6e illustrates an alternative exemplary embodiment of a noose device. The noose device in FIG. 6e comprises a relatively rigid member 126e, similar to the relatively rigid member 126 of FIG. 6b. The member 126e is positioned on the posterior side of the mitral valve MV. Preferably, the rigid member 126e, which is placed on the loop portion 122, may be formed by bending or the like to a desired shape so as to impart a desired shape change to the posterior annulus. The rigid member 126e can be of any desired shape, and may include one or more local regions of indentations.

Another aspect of the present invention includes an internal strut device that operates to treat mitral valve dysfunction by causing a shape change to the mitral valve annulus while maintaining or restoring the normal distance between the trigones of the valve. The device also may move the posterior leaflet face closer to the anterior-leaflet face. Combined, these movements tend to increase the coaptation area of the mitral valve leaflets and improve mitral valve function. An exemplary embodiment of an internal strut device is shown in FIGS. 7a and 7b.

Figure 7A:
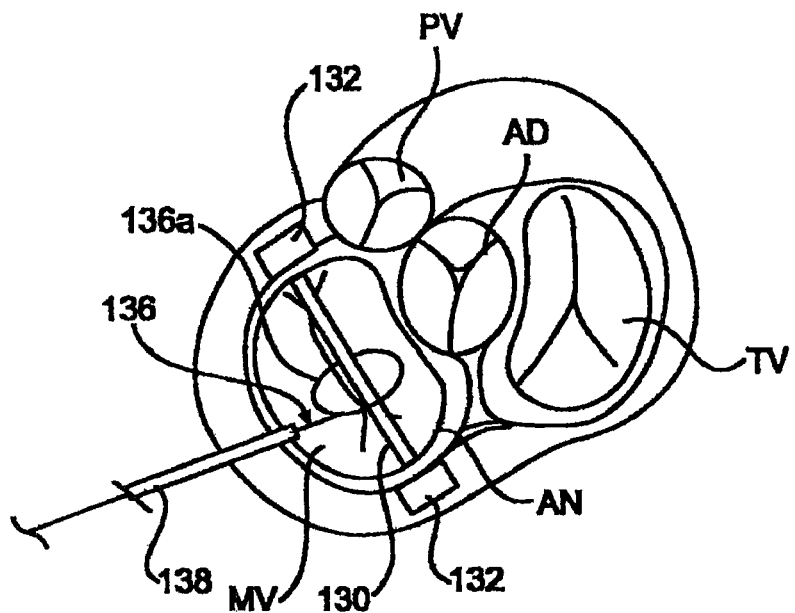
FIG. 7a is a short axis, cross-sectional view of a heart showing an exemplary embodiment of an elongate bar and a snare device around the elongate bar implanted to treat the mitral valve according to an aspect of the invention.
Figure 7B:
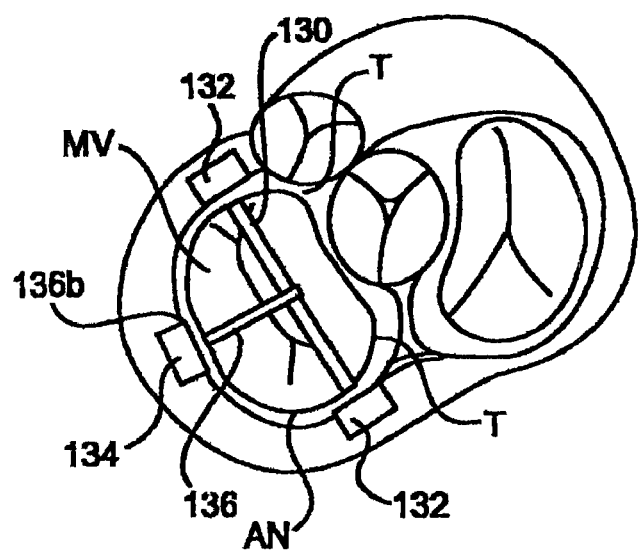
FIG. 7b is a short axis, cross-sectional view of a heart showing an embodiment of an internal strut device implanted to treat the mitral valve according to an optional aspect of the present invention.

The embodiment of the internal strut device shown in FIGS. 7a and 7b generally comprises a relatively rigid elongate member 130 positioned so as to extend substantially along the line of leaflet coaptation of the mitral valve. The relatively rigid elongate member 130 may be positioned in close proximity to the valve annulus AN, either slightly above or slightly below the annulus AN, so as to appropriately affect the valve leaflets and move them into a desired position. A second elongate member 136 may be provided so as to extend substantially perpendicular to the relatively rigid elongate member 130 and to the line of leaflet coaptation. The relatively rigid elongate member 130 may be fixed to the outer walls of the left atrium or the left ventricle, depending on the positioning of the member 130 with respect to the mitral valve MV. Sutures, anchor pads, or other similar mechanisms may secure the member 130 with respect to the leaf. FIGS. 7a and 7b illustrate the use of anchor pads 132 for securing the relatively rigid, elongate member 130.

Providing a relatively rigid elongate member 130 may substantially prevent the member from bending or buckling, which may in turn help to maintain the desired trigonal distance. The member 130 may be a rigid bar made from biocompatible metals, such as nitinol, titanium, chrome-alloys, MP-35N, and other similar metals, or from biocompatible polymers, such as PEEK, acetyl, or other similar materials. Optionally, the bar may be an extendable, telescoping bar (not shown). This may permit the length of the bar to be adjusted as necessary to optimize the trigonal distance.

The second elongate member 136 may optionally be in the form of a snare having a loop portion 136a that is secured around the relatively rigid member 130. The snare may be tightened as desired and the free end 136b may be secured via an anchor pad 134 placed adjacent an exterior surface of the heart wall. Once secured, the snare essentially forms a tension member anchored at one end to the relatively rigid member 130 and at the opposite end to the heart wall. Together, the relatively rigid member 130 and the second elongate member 136 impart a shape change to the mitral valve annulus, while maintaining the distance between the valve trigones T. Alternatively, the distance between the valve trigones also may be altered to achieve a more normal distance between them if necessary.

An exemplary embodiment for the delivery and implantation of the internal strut device of FIGS. 7a and 7b will now be explained. An introducer 138, such as a trocar or other suitable introducer mechanism, may be inserted through the heart wall proximate the level of the mitral valve annulus AN. As shown in FIG. 7a, the introducer 138 may be inserted in a substantially perpendicular direction relative to the line of coaptation of the mitral valve leaflets. Once the introducer is inserted, the second elongate member 136, in the form of a snare in FIGS. 7a and 7b, may be inserted through the introducer 138 and positioned with the loop portion 136a substantially in the middle of the mitral valve annulus AN. The relatively rigid elongate member 130 may then be inserted through the left atrial wall (not shown) at approximately the same annular level as the snare 136. However, the member 130 is advanced in a direction along the line of coaptation of the mitral valve leaflets and substantially perpendicular to the snare 136. The member 130 may be passed through the loop portion 136a of the snare 136 and through the wall surrounding the left atrium located substantially opposite to the wall through which the member 130 was inserted. Once extended transverse the left atrium LA, securing mechanisms, such as anchor pads 132, for example, may fix the member 130 with respect to the heart. Prior to securing the member 130, its length between the chamber walls may be adjusted, as described above, in order to alter the distance between the valve trigones as desired.

Once the relatively rigid elongate member 130 is secured into position, the snare loop portion 136a may be tightened around it and the snare 136 secured on the external surface of the atrial wall by a securing mechanism, such as anchor pad 134 as shown in FIG. 7b. Thus, the snare 136 also may induce a shape change to the mitral valve annulus AN, as shown by the indented region of the mitral valve annulus in FIG. 7b. Both the relatively rigid elongate member 130 and the snare 136 may have their lengths adjusted as necessary to provide the overall desired shape change of the mitral valve annulus.

The snare 136 may optionally be secured using a securing mechanism that extends from the annular level of the left atrium LA down the epicardial surface to a region proximate the left ventricle LV. This would allow the strut device to change the shape of the mitral valve both at a level of the valve annulus and at a subvalvular level.

In an alternate embodiment (not shown), the relatively rigid bar may be replaced by a splint assembly similar to the splint assemblies disclosed in U.S. application Ser. No. 09/680,435, incorporated by reference herein. Such a splint assembly would be relatively flexible and capable of adjusting in length by adjusting the position of the anchor members with respect to the tension member of the splint assembly. The splint assembly may extend along the line of coaptation of the valve leaflets. In this case, the length of the tension member between the heart walls may be adjusted in order to maintain or achieve a more desirable trigonal distance.

Yet another exemplary embodiment for treating a heart valve includes an intrawall splint comprising an elongate member configured to be implanted within the heart wall so as to extend around a portion of the chamber. The elongate member may optionally be either wire-like, similar to the braided tension members used with the splint assemblies of U.S. application Ser. No. 09/680,435, incorporated by reference herein, or tubular. Because the device of this optional embodiment is implanted within and exterior to the heart wall, there is substantially no blood contact with the device, reducing the risk of thrombus formation.

Figure 8:
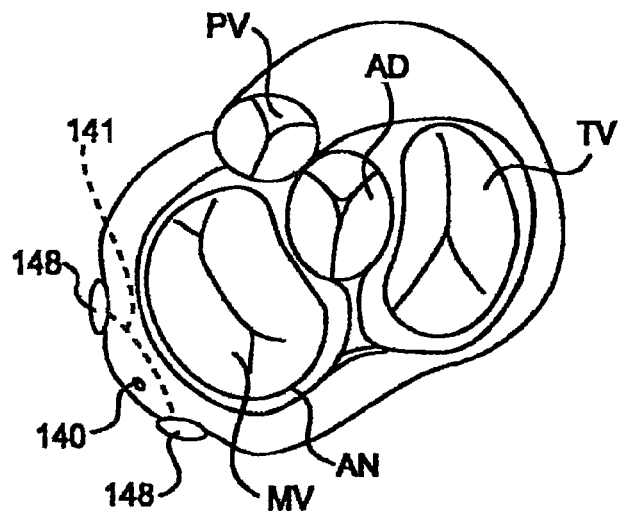
FIG. 8 is a short axis, cross-sectional view of a heart implanted with an exemplary embodiment of an intrawall splint according to an aspect of the invention.

An example of an intrawall splint 140 according to an exemplary embodiment of the invention is shown in FIG. 8. The intrawall splint 140 comprises an elongate member 141 that may be implanted within the lateral myocardial wall of the heart, optionally near the atrio-ventricular groove, in an area substantially coinciding with or slightly offset from the annular edge of the posterior leaflet. In the embodiment shown in FIG. 8, the elongate member 141 is secured to the heart using anchor assemblies 148, which may have configurations similar to those discussed with reference to FIGS. 4b, 5d, 7a, and 7b, for example. The anchor assemblies 148 attach to the end portions of the elongate member 141 at an exterior surface of the heart wall. The anchor assemblies 148 may move along the length of the elongate member 141 to adjust the degree of compression on the heart wall. By appropriately positioning the anchor assemblies 148 on the elongate member 141, the arc length of the mitral valve annulus along the posterior side of the valve may be reduced. This may increase the coaptation area between the valve leaflets and decrease the annular cross-section. Once a suitable degree of shape change of the valve annulus occurs, which may be determined by observing the mitral valve regurgitation through the use of echocardiagraphic or other similar visualization techniques, the anchor assemblies 148 may be fixed to the elongate member 141 to hold the elongate member 141 in place with respect to the heart. The elongate member 141 and the anchor assemblies 148 shown in FIG. 8 may be implanted in a manner similar to the implantation techniques for the splint assemblies of U.S. application Ser. No. 09/680,435, incorporated by reference herein.

The elongate member 141 may be made of bio-inert, biostable, and/or bio-resorbable materials. In each of these cases, the implantation of the elongate member 141 within the heart wall may provoke a healing response by the heart wall. This healing response may elicit a chronic process that results in the shrinkage of the tissue in a direction along the axis of the elongate member. In another exemplary configuration, the elongate member 141 may be configured so as to deliver heat to the heart wall during delivery. Such heat also may initiate a healing response in the heart wall tissue, resulting in tissue shrinkage along the elongate member. For example, the member 141 may be made of a conductive metal and be heated, such as by temporarily exposing it to an electrical current, preferably in the RF range. In an exemplary embodiment, the RF range will be chosen so as to minimize electrical interference with the heart's conduction system.

Figure 9:
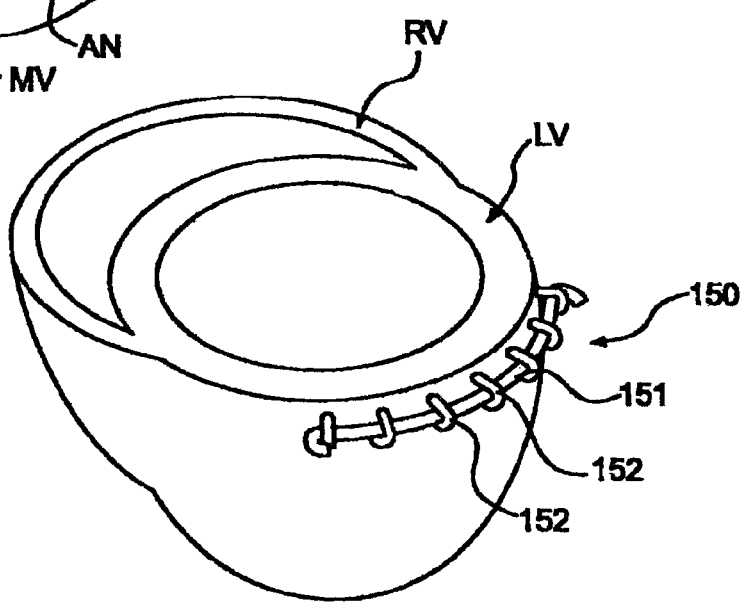
FIG. 9 is a partial perspective view of a heart implanted with an exemplary embodiment of an external plication device according to an aspect of the invention.

Another exemplary embodiment of the invention includes an external application device that may be positioned on an exterior surface of the heart wall near the posterior mitral valve annulus in substantially the same plane as the annulus. As with other devices discussed herein, such an external application device may be placed so as to reduce the valve annulus cross-section and increase the valve leaflet coaptation area. FIG. 9 shows an example of an external application device 150 according to an aspect of the invention. The external application device 150 comprises a curved rod 151 anchored on an exterior surface of the heart wall by a series of sutures 152. A series of tissue anchors may be used instead of sutures. The rod 151 may be shortened, for example, by telescoping, to a fixed length to provide a reduction of the lateral heart wall and/or posterior annular space. Alternatively, the external application device may be implanted so as to reposition the papillary muscles, such as by reducing the intrapapillary distance, for example.

The rod 151 may be either relatively rigid or relatively flexible. A relatively flexible rod 151 may take the form of a tension member, such as the tension members used with the splint assemblies of U.S. application Ser. No. 09/680,435, incorporated by reference herein. A relatively rigid rod may be preferable to provide a local shape change, while a relatively flexible rod may be preferable for changing the arc length of at least a portion of the valve annulus. The external application device may be made of biocompatible materials. Alternatively, the external application device may be made of bioresorbable materials that provoke a chronic healing response of the heart wall tissue. This healing response may result in a scarring, causing the tissue to shrink in a particular direction, thereby reducing the posterior annular arc length.

As with the intrawall splint device of FIG. 8, the external application device is implanted so as to substantially avoid blood contact within the heart chamber, which reduces the risk of thrombus formation.

The devices of FIGS. 8 and 9 are shown in position on the lateral wall of the heart proximate the posterior aspect of the mitral valve annulus. It is contemplated, however, that these devices may be implanted in other positions with respect to the heart while still helping to reduce mitral valve regurgitation or to treat other heart valves altogether.

Yet another aspect of the invention includes the use of so-called "plug" devices, for treating incompetent heart valves. These plug devices are intended assist in closing the mitral valve to prevent regurgitation by increasing the coaptation area of the mitral valve leaflets and/or decreasing the coaptation depth of the mitral valve leaflets. This generally may be accomplished by placing a plug device in the "hole" between the valve leaflets (i.e., the valve orifice), thereby providing a surface against which the valve leaflets may abut (i.e., coapt), in order to close the mitral valve during systole. The plug devices described herein assist in closing the mitral valve substantially without altering the shape of the valve annulus and/or repositioning the papillary muscles. To further understand how the plug devices according to optional aspects of the invention operate to improve mitral valve function, reference is made to the various optional embodiments of the device shown in FIGS. 10b-11m(ii).

Figure 10A:
FIG. 10a is a schematic side view of an improperly functioning mitral valve during systole.
Figure 10B:
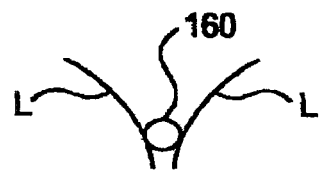
FIG. 10b is a schematic side view of the valve of FIG. 10a with an exemplary embodiment of a plug device implanted in the valve orifice according to an aspect of the invention.

FIG. 10a illustrates a schematic side view of the leaflets L of a dysfunctional mitral valve during systole. As seen in this figure, the leaflets L do not coapt so as to close the mitral valve orifice. Therefore, regurgitant flow will occur through the valve during systole. FIG. 10b illustrates the valve of FIG. 10a during systole with an exemplary embodiment of a plug member 160 of the present invention implanted in the valve leaflet coaptation space. As can be seen, the presence of the plug member 160 will block the regurgitant flow through the valve during systole as the leaflets L abut against the outer surface of the plug member 160. In other words, the plug member 160 "plugs" the valve orifice during systole to hinder or prevent blood from leaking through the valve.

In the exemplary embodiments of FIGS. 11a-11f, a plug member is suspended in the coaptation space substantially in the area where regurgitant blood flow occurs. The suspended plug member may have a variety of shapes depending on factors such as the mitral valve geometry, the alignment of the valve leaflets, and the size and shape of the regurgitant opening during systole. For example, the suspended plug member may have a spherical configuration (160a in FIG. 11a), an ellipsoidal configuration (160b in FIG. 11b), a disk-shaped configuration (160c in FIG. 11c), a wing-like configuration (160d in FIG. 11d), or a sheet-like configuration (160e in FIG. 11e, 160f in FIG. 11f). FIGS. 11a-11e show schematically a partial cross-sectional view of the mitral valve with the various plug members disposed between the valve leaflets L and within the valve orifice.

In FIGS. 11a-11d, the valve is shown in an open position, with a space between the valve leaflets L and the outer surface of the plug member 160a-160d to allow blood flow therethrough. During closure of the valve, the leaflets L abut against the outer surface of the plug member 160a-160d, thereby preventing regurgitation through the valve orifice, which may otherwise occur if the leaflets are unable to properly coapt against one another. FIG. 11e shows schematically a partial cross-sectional view of a mitral valve during systole with a plug member 160e disposed between the valve leaflets L. The presence of the plug member 160e permits the valve to close during systole as a result of the valve leaflets L coapting against the surface of the plug member 160e. This coaptation will substantially prevent regurgitant blood flow from occurring during systole.

Figure 11A:
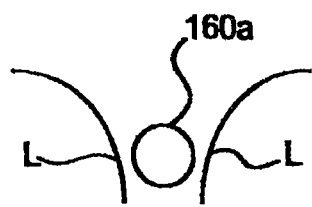
FIG. 11a is an exemplary embodiment of a spherical plug device implanted in the valve orifice between the valve leaflets according to an aspect of the invention.
Figure 11B:
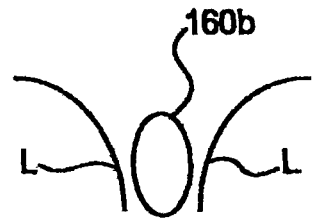
FIG. 11b is an exemplary embodiment of an ellipsoidal plug device implanted in the valve orifice between the valve leaflets according to an aspect of the invention.
Figure 11C:
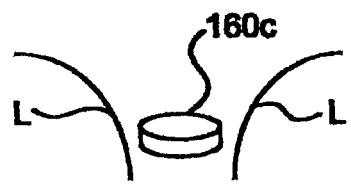
FIG. 11c is an exemplary embodiment of a disk-shaped plug device implanted in the valve orifice between the valve leaflets according to an aspect of the invention.
Figure 11D:
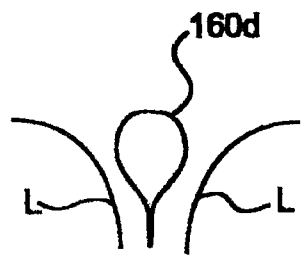
FIG. 11d is an exemplary embodiment of a wing-shaped plug device implanted in the valve orifice between the valve leaflets according to an aspect of the invention.
Figure 11E:
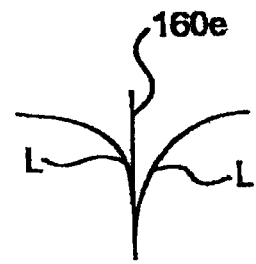
FIG. 11e is an exemplary embodiment of a sheet-like plug device implanted in the valve orifice between the valve leaflets according to an aspect of the invention.

A suspended member 160d having a wing-like configuration, as shown in FIG. 11d, may provide an advantageous surface for the valve leaflets L to close against due to its tapered configuration. The tapered configuration substantially mutually corresponds to the profile of the valve leaflets surfaces themselves. Such a tapered and mutually corresponding shape may help to reduce thrombus formation at the blood-surface contact points with the suspended member 160d. Moreover, this shape may reduce insult to the valve leaflets L as they close against the surface of the suspended member 160d.

A suspended member 160e having a substantially sheet-like configuration may be particularly suitable for use as a plug device in patients having misaligned leaflets. In this case, as shown in FIG. 11e, the ends of the valve leaflets L tend to reach the centerline of the valve as they come together during systole. However, the leaflets L are arranged such that the ends of the leaflets L are in different transverse planes upon closing of the valve, therefore hindering proper coaptation and valve closure. The substantially planar plug member 160e in FIG. 11e may be suspended substantially along the centerline of the valve, providing the misaligned valve ends with a surface to abut against. Due to its substantially planar configuration, the plug member 160e may minimize the cross-sectional area of the blood flow path that is blocked by the device, while also providing the desired closure of the valve. In an alternative embodiment, shown in FIG. 11f, the sheet-like plug 160f may be constructed of two layers sealed along their perimeters. This embodiment therefore may form an inflatable structure. Such an inflatable plug member may permit the cross-section of the member to be selected and varied according to the size of the "hole" between the improperly coapting valve leaflets.

As shown in the FIGS. 11a-11f, the plug members 160 operate to reduce mitral valve regurgitation and improve valve function by providing a surface against which the mitral valve leaflets may coapt during systole, thereby closing the valve to blood flow therethrough. Thus, these plug members 160 may operate as plugs to close the hole otherwise left open due to the inability of the valve leaflets to properly coapt. Providing such a surface against which the mitral valve leaflets may coapt may benefit both patients having valve leaflets with a reduced range of motion, for example, due to chordal tethering, and/or patients having leaflets unable to coapt due to left ventricular dilatation. The plug devices of FIGS. 11a-11f also may enhance coaptation in patients whose leaflets are misaligned, since each leaflet may coapt with the surface provided by the plug member independently of the other leaflet.

Materials suitable for construction of the various plug devices disclosed herein may be categorized generally into the following broad groups: synthetic polymers, biological polymers, metals, ceramics, and engineered tissues. Suitable synthetic polymers may include flouroethylenes, silicones, urethanes, polyamides, polyimides, polysulfone, poly-ether ketones, poly-methyl methacrylates, and other similar materials. Moreover, each of these compositions potentially may be configured from a variety of molecular weights or physical conformations.

Suitable metals may be composed from a variety of biocompatible elements or alloys. Examples include titanium, Ti-6AL-4V, stainless steel alloys, chromium alloys, and cobalt alloys. The stainless steel alloys may include, for example, 304 and 316 stainless steel alloys. The cobalt alloys may include Elgiloy, MP35N, and Stellite, for example.

Suitable ceramic materials may be fashioned from pyrolytic carbon and other diamond-like materials, such as zirconium, for example. These materials may be applied to a variety of core materials, such as graphite, for example.

As for biological materials for manufacturing the devices, a variety of fixed tissues may be useful in the fabrication process. Base materials, such as pericardium, facia mater, dura mater, and vascular tissues may be fixed with a variety of chemical additives, such as aldehydes and epoxies, for example, so as to render them nonimmunogenic and biologically stable.

Tissues also may be engineered to meet the intended purpose. Substrates may be constructed from a variety of materials, such as resorbable polymers (e.g., polylactic acid, polyglycolic acid, or collagen). These materials may be coated with biologically active molecules to encourage cellular colonization. Additionally, these tissues may be constructed in vitro, for example using the patient's own cells or using universal cell lines. In this way, the tissue may maintain an ability to repair itself or grow with the patient. This may be particularly advantageous in the case of pediatric patients, for example.

Each of the previously mentioned materials also may be subjected to surface modification techniques, for example, to make them selectively bioreactive or nonreactive. Such modification may include physical modification, such as texturing;

surface coatings, including hydrophilic polymers and ceramics (e.g., pyrolytic carbon, zirconium nitrate, and aluminum oxide); electrical modification, such as ionic modification, for example; or coating or impregnation of biologically derived coatings, such as heparin, albumin, a variety of growth healing modification factors, such as, for example, vascular endothelial growth factors (VEGF), or other cytokines.

The tethers used to suspend the plug members, which will be described in more detail shortly, may be constructed of either monofilament or multifilament constructions, such as braids or cables, for example. Materials such as high strength polymers, including liquid crystal polymers (Vectran) and ultra high molecular weight polyethylene fibers (Spectra) may be suitable to provide desirable mechanical and fatigue properties. Suitable metals may include stainless steel, titanium alloys, and cobalt-chrome alloys, for example.

The materials discussed above are exemplary and not intended to limit the scope of the invention. Those skilled in the art would recognize that a variety of other similar suitable materials may be used for the plug devices and suspension members disclosed herein.

Figure 12:
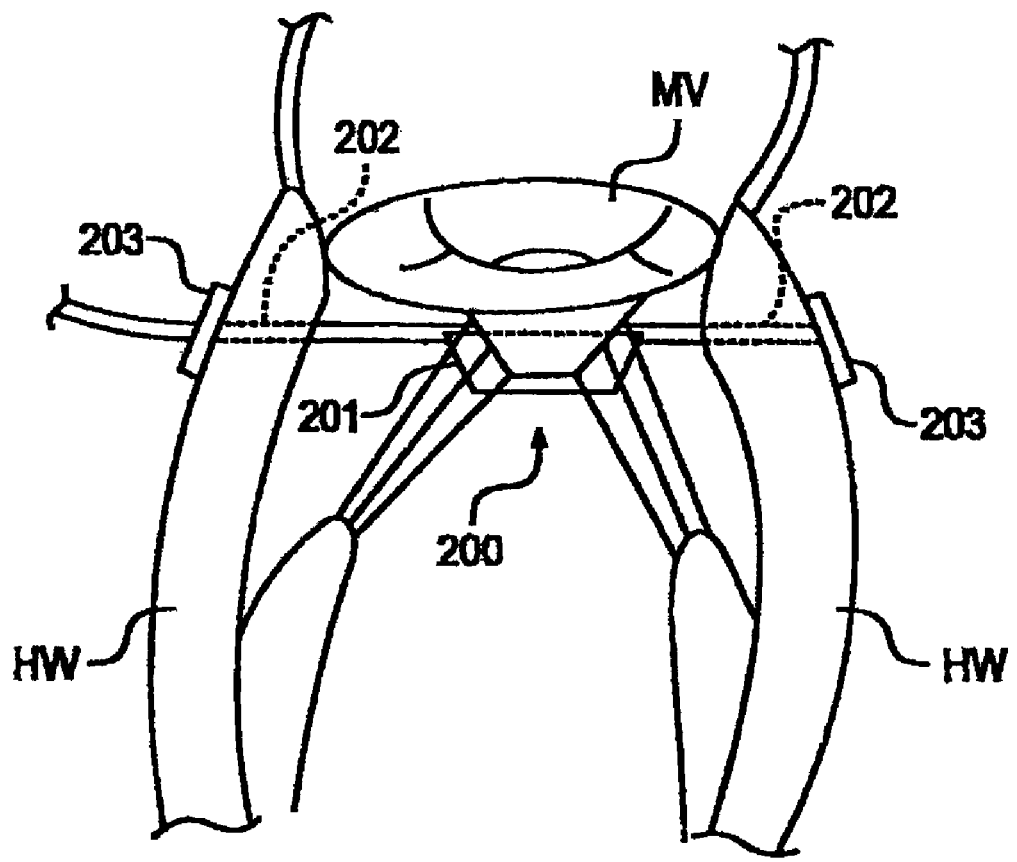
FIG. 12 is a partial perspective view of the heart showing a plug device implanted in the heart according to an optional aspect of the invention.

The suspended plug members 160a-160f of FIGS. 11a-11f may be anchored to the heart walls using anchoring members such as, for example, internal tissue anchors or anchor pads attached externally of the heart. An example of utilizing external anchor pads for suspending the plug members 160 within the valve orifice is illustrated in FIG. 12, which will be explained in more detail shortly.

Yet another exemplary embodiment of a plug device is illustrated in FIGS. 11g(i), 11g(ii). The device of FIGS. 11g(i), 11g(ii) comprises a tubular member 167 that may be at least partially collapsible and flexible. The top portion of the tubular member 167 may include a ring structure 168 that may be placed on the mitral valve annulus. The remaining portions of the tubular member 167 may be placed through the valve orifice between the valve leaflets such that the tubular member 167 extends at least partially into the left ventricular chamber. When pressure in the left ventricle increases, such as during systole, for example, the mitral valve leaflets may begin to close. As the leaflets begin to close, the tubular member 167 collapses, as shown in FIG. 11g(ii), so as to close the tube 167 at its distal end. This closure closes the blood flow path between the left atrium and the left ventricle. Once the pressure in the left atrium again becomes higher than the pressure in the left ventricle, the tubular member 167 may open to allow bloodflow therethrough. The tubular plug member 167 itself therefore provides a type of valving mechanism without the need to remove the natural valve or provide other mechanical valve devices.

Other embodiments of expandable/collapsible plug devices that operate to perform valving functions are shown in FIGS. 11h-11j. FIGS. 11h(i), 11h(ii) illustrate a collapsible plug member 169 that has a hollow, tapered configuration. During diastole, as shown in FIG. 11h(i), the plug member 169 has an expanded configuration so that blood can flow through the plug member 169 and also between the leaflets L and the outer surface of the plug member 169. The plug member 169 is configured to collapse during systole, as shown in FIG. 11h(ii), so that the bottom portion 169B of the plug facing the left ventricle is closed off to prevent blood flow through the plug 169. In the collapsed configuration, the member 169 maintains a relatively wide profile at a top portion 169T and tapers toward the bottom portion 169B where the sides of the plug member 169 come together to close the plug member 169 to flow therethrough. The tapered sides also allow the valve leaflets to close against the plug member 169 during systole. In this manner, blood is substantially prevented from flowing through the mitral valve during systole.

FIGS. 11i(i), 11i(ii) show yet another exemplary embodiment of a collapsible and expandable plug member 170. The plug member 170 includes two wing members 170a, 17b, and an articulation 171 connecting the two wing members 170a, 170b at their top ends. During systole, as shown in FIG. 11i(i), the pressure in the left ventricle acts on the wing members 170a, 170b, causing them to pivot about the articulation 171 in an outward direction (i.e., the wing members 170a, 170b pivot away from each other). This pivoting outward of the wing members 170a, 170b allows the wing members 170a, 170b to abut with the valve leaflets L, thus closing the valve orifice to prevent bloodflow through the valve.

During diastole, as shown in FIG. 11i(ii), pressure from the left atrium causes the wing members 170a, 170b to pivot about the articulation 171 in an inward direction (i.e., the wing members 170a, 170b pivot toward each other). Thus, the wing members 170a, 170b separate from the leaflets L, allowing blood to flow through the valve from the left atrium into the left ventricle.

Yet another exemplary embodiment of an expandable and collapsible plug device is shown in FIGS. 11j(i), 11j(ii). FIG. 11j(i) shows a collapsible plug member 172 during systole and FIG. 11j(ii) shows the collapsible plug device 172 during diastole. During systole, the plug member 172 essentially is in the form of a hollow cone with a base of the cone disposed proximate the free ends of the valve leaflets L. The sides 172a, 172b of the cone take on a concave configuration during systole, as shown in FIG. 11j(ii) so as to allow blood to flow between the sides 172a, 172b and the valve leaflets L. During diastole, the blood flow through the valve will cause the plug member 172 to expand, thereby billowing the side walls 172a, 172b outwardly such that they abut the valve leaflets L to restrict or prevent blood from flowing through the valve.

Another exemplary embodiment for a plug device may comprise a member that is suspended in place below the free edges of the valve leaflets in a plane substantially parallel to the valve annulus. Such a plug device is shown in FIG. 11k. In this embodiment, a piston-like plug device 173 having a disk member 174 suspended on the end of an elongate member 174' is movable along the longitudinal axis of the valve. The disk member 174, which preferably has a circular or oval shape, is movable into and out of contact with the free ends of the valve leaflets L in accordance with the bloodflow through the heart. In this manner, the piston-like plug device 173 may operate similar to a one-way check valve, reducing regurgitation during systole by moving to seal the free ends of the valve leaflets L with the disk-like member 174, as shown in FIG. 11k, for example. During diastole, the piston-like plug device 173 may move in a direction toward the left ventricle such that the disk member 174 moves out of contact with the free ends of the valve leaflets L. FIGS. 11l(i), 11l(ii) show an alternative arrangement of the piston-like plug device 173 of FIG. 11k. In this embodiment, the disk member 174l is made of a flexible or semi-flexible material. This material may allow the disk member 174l to obtain a reduced cross-sectional profile during diastole, as shown in FIG. 11l(i), allowing for a relatively normal size valve orifice blood flow area. During systole, the disk member 174l expands and inverts as pressure in the left ventricle increases causing blood to flow toward the valve. The disk member 174l envelops the ends of the valve leaflets L to substantially prevent regurgitant bloodflow through the valve, as shown in FIG. 11l(ii).

Yet another alternative arrangement of a plug device is shown in FIGS. 11m(i), 11m(ii). In this exemplary embodiment, the device 175 is implanted such that a disk-like member 176 is situated substantially above the level of the valve leaflets L proximate the valve annulus AN. As shown in the FIG. 11*m(i)*, the perimeter of the disk-like member 176 contacts the upper portions of the valve) leaflets L proximate the valve annulus AN as the pressure in the left ventricle increases during systole, moving the valve leaflets L toward one another. This contact facilitates closure of the mitral valve orifice. On the other hand, during diastole, as shown in FIG. 11*m(ii)*, the leaflets L move away from and out of contact with the disk-like member 176, allowing blood to flow between the disk-like member 176 and the valve leaflets L from the left atrium LA in to the left ventricle LV.

The various devices shown in FIGS. 11*a*-11*m(ii)* can be delivered and implanted in the heart using numerous approaches. FIG. 12 shows one example of an embodiment for implanting, a plug device of the invention, indicated generally as 200, in the heart. In FIG. 12, the plug member 201 is suspended from at least one elongate member 202. The elongate member 202 optionally has a tether-like structure. Anchors 203 are provided on the ends of the elongate member 202 to secure the device to exterior portions of the heart wall HW. The anchors 203 optionally may be similar to the anchors discussed above with reference to FIGS. 4*b* and 5*d*, for example. FIG. 12 shows an exemplary implantation position, namely a sub-annular position, for the plug device 200 with respect to the heart.

Figure 13A:
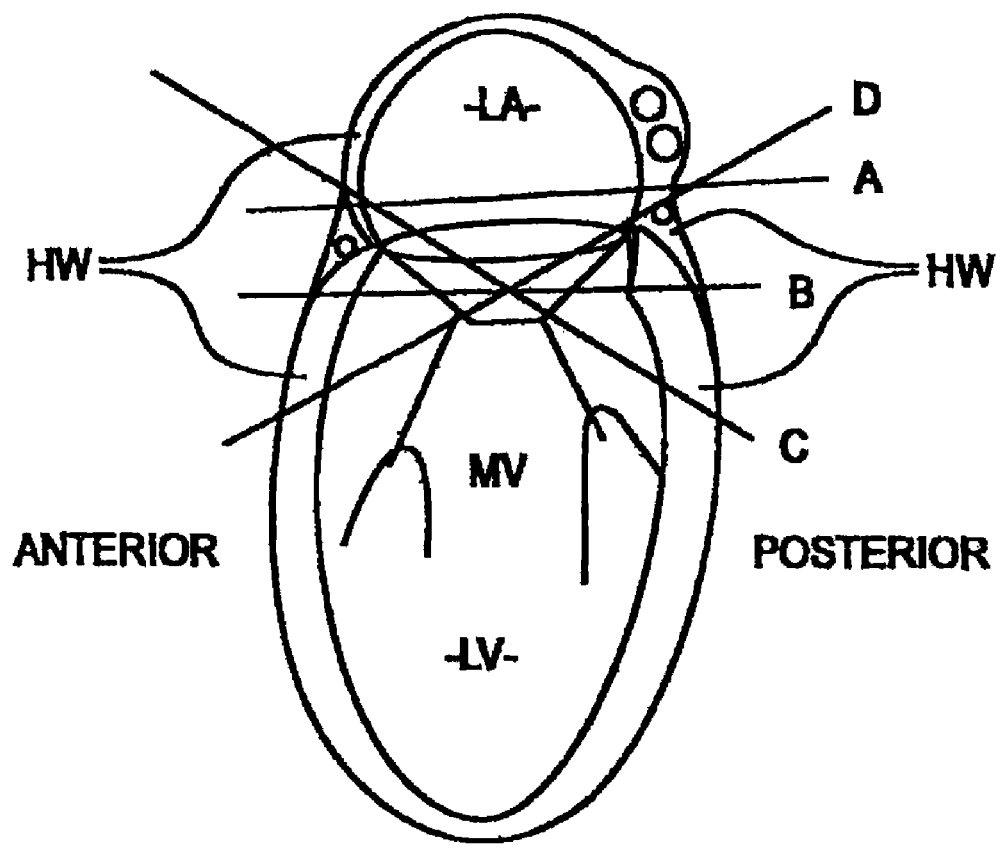
FIG. 13a is a long axis cross-sectional view of the left ventricle and left atrium of a heart showing schematically various exemplary positions for a plug device according to an optional aspect of the invention.
Figure 13B:
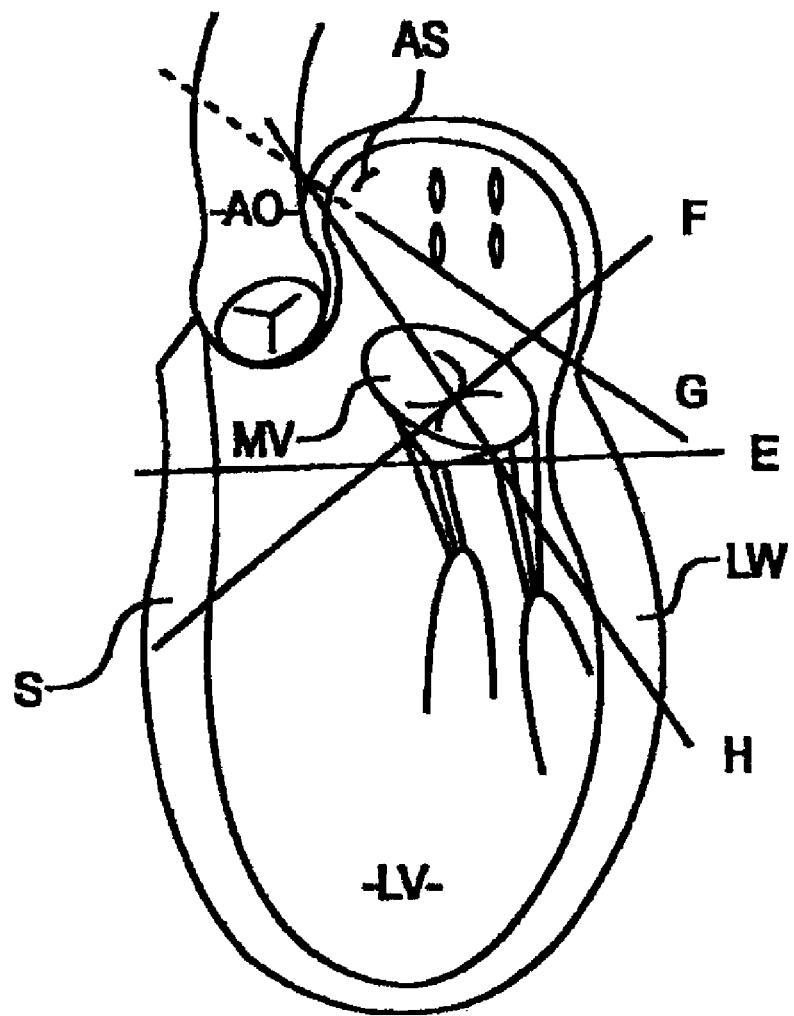
FIG. 13b is a long axis cross-sectional view of the left ventricle and left atrium of a heart showing schematically various exemplary positions for a plug device according to an aspect of the invention.
Figure 13C:
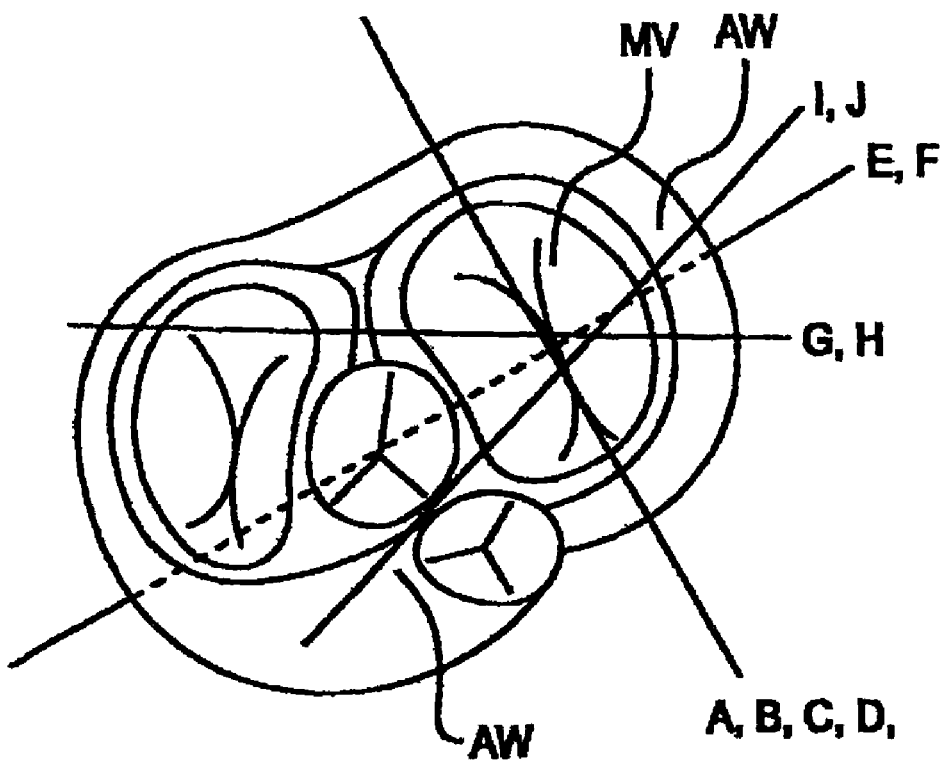
FIG. 13c is a basal cut away cross-sectional view of the heart showing schematically various exemplary positions for a plug device according to an aspect of the invention.
Figure 13D:
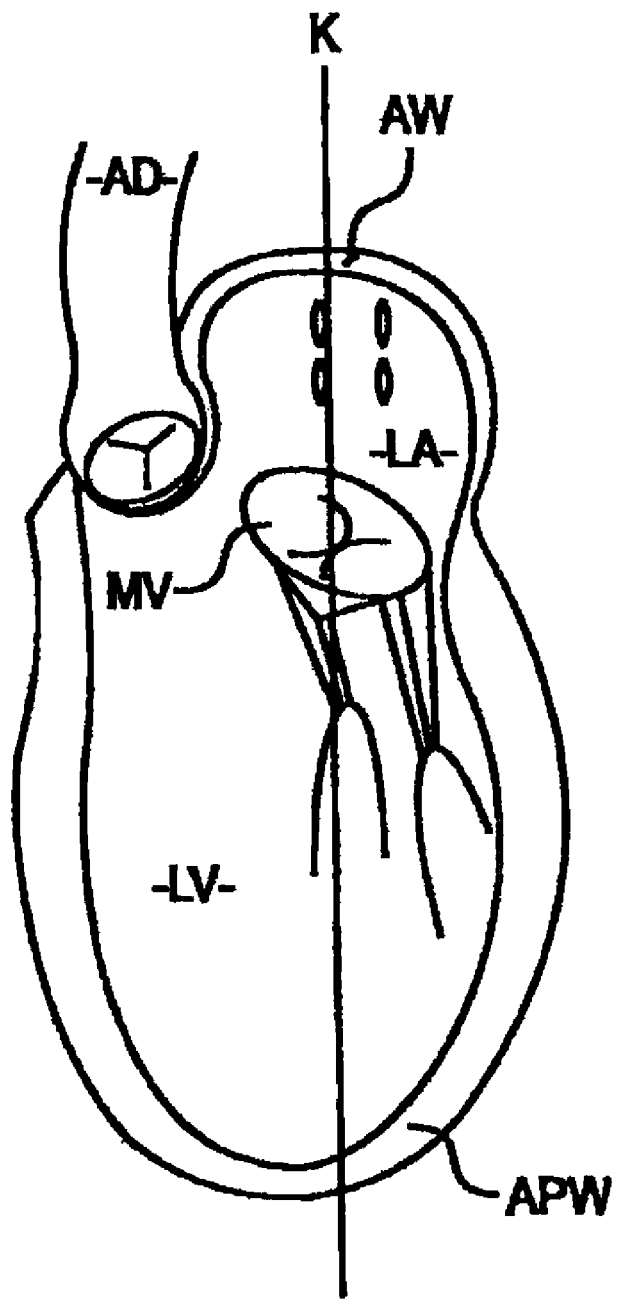
FIG. 13d is a long axis cross-sectional view of the left ventricle and left atrium of a heart showing schematically an exemplary position for a plug device according to an aspect of the invention.

Numerous other implantation positions for the plug devices, discussed above with reference to FIGS. 11*a*-11*m*, are envisioned and are considered within the scope of the invention. Some examples of these positions are shown in FIGS. 13*a*-13*d*. The lines shown in these figures represent the extension of the elongate member (or members) 202, from which the plug member is suspended, between the anchors 203 secured to the exterior portions of the heart wall HW. FIG. 13*a* shows a long axis cross-sectional view (from the lateral side) of the left ventricle LV and left atrium LA. Each of the positions shown by lines A-D represents anterior-to-posterior positioning of a plug device. Line A represents a supra-annular, anterior-to-posterior position; line B represents a sub-annular, anterior-to-posterior position; line C represents a supra-annular, anterior to sub-annular, posterior position, and line D represents a supra-annular, posterior to sub-annular, anterior position. FIG. 13*b* shows various lateral-medial positions for a plug device. The various positions are indicated by lines E-H in FIG. 13*b*. Line E represents an intraventricular septum S to sub-annular, lateral wall LW position; line F represents an intraventricular septum S to supra-annular, lateral wall LW position; line G represents an atrial septum AS to supra-annular, lateral wall LW position; and line H represents an atrial septum AS to sub-annular, lateral wall LW position. FIG. 13*c* shows a basal cut-away, cross-sectional view of the heart with the various positions corresponding to lines A-H in FIGS. 13*a* and 13*b* represented. FIG. 13*c* also shows two additional optional positions, indicated by lines I and J, for the implantation of the plug devices. Line I represents an anterior-medial, supra-annular atrial wall AW to supra-annular atrial wall AW position and line J represents an anterior-medial, supra-annular atrial wall AW to sub-annular atrial wall AW position. FIG. 13*d* shows a long-axis cross-sectional view of the left ventricle LV and left atrium LA with an apical wall APW to atrial wall AW position, indicated by line K.

The particular position selected to implant a plug device may depend on a variety of factors, such as the condition of the patient's heart, including the heart valves, the delivery technique utilized to implant the device, the type of plug device utilized to treat the valve, and other similar factors. Each of the positions shown in FIGS. 13*a*-13*d*, however, permits proper positioning of the plug device to prevent regurgitation and avoids damage to key coronary structure. Further, particular positions may be selected based on factors such as, for example, the geometry, including size and shape, of the valve orifice.

The plug devices of FIGS. 11*a*-11*m(ii)* may be delivered to the heart in several ways, including ways that do not require placing the patient on bypass. Perhaps the most direct approach includes obtaining open chest access to the left ventricular and atrial walls. However, the devices also may be implanted using off-pump surgical techniques or endovascular techniques.

Figure 14A:
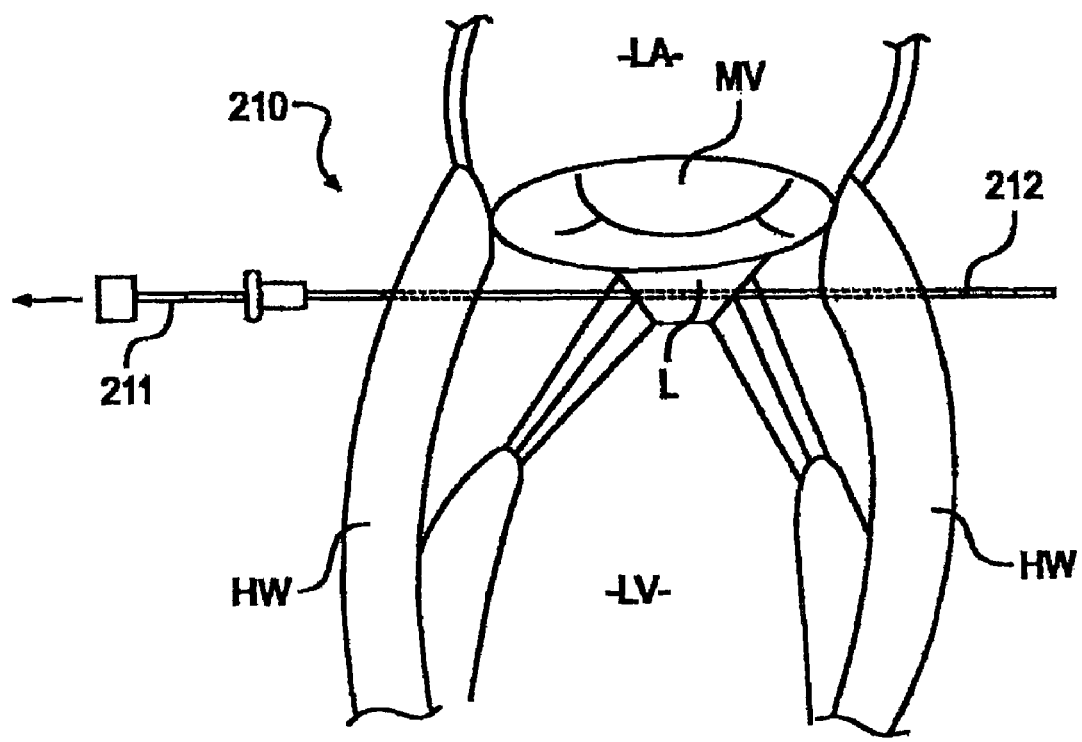
FIG. 14a is a partial perspective view of the left ventricle and left atrium of a heart showing an exemplary embodiment of a needle and stylet assembly for delivering a plug device according to an aspect of the invention.
Figure 14B:
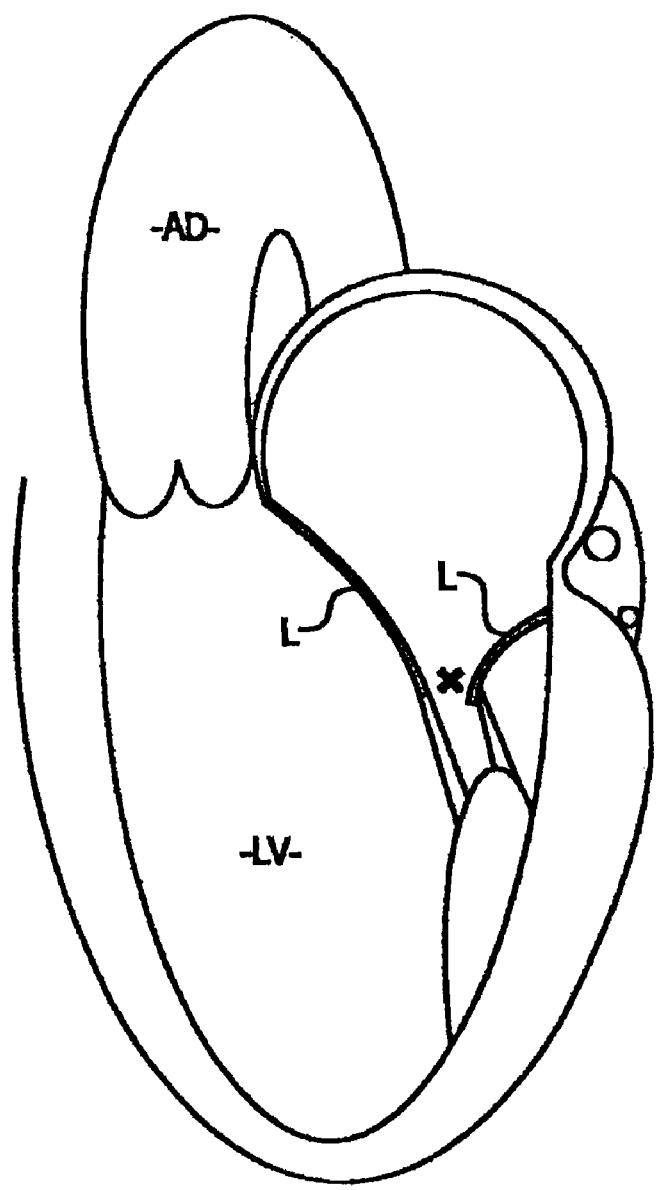
FIG. 14b is a long axis cross-sectional view of the heart showing the placement of the needle and stylet assembly of FIG. 14a relative to the mitral valve leaflets according to, an aspect of the invention.
Figure 14C:
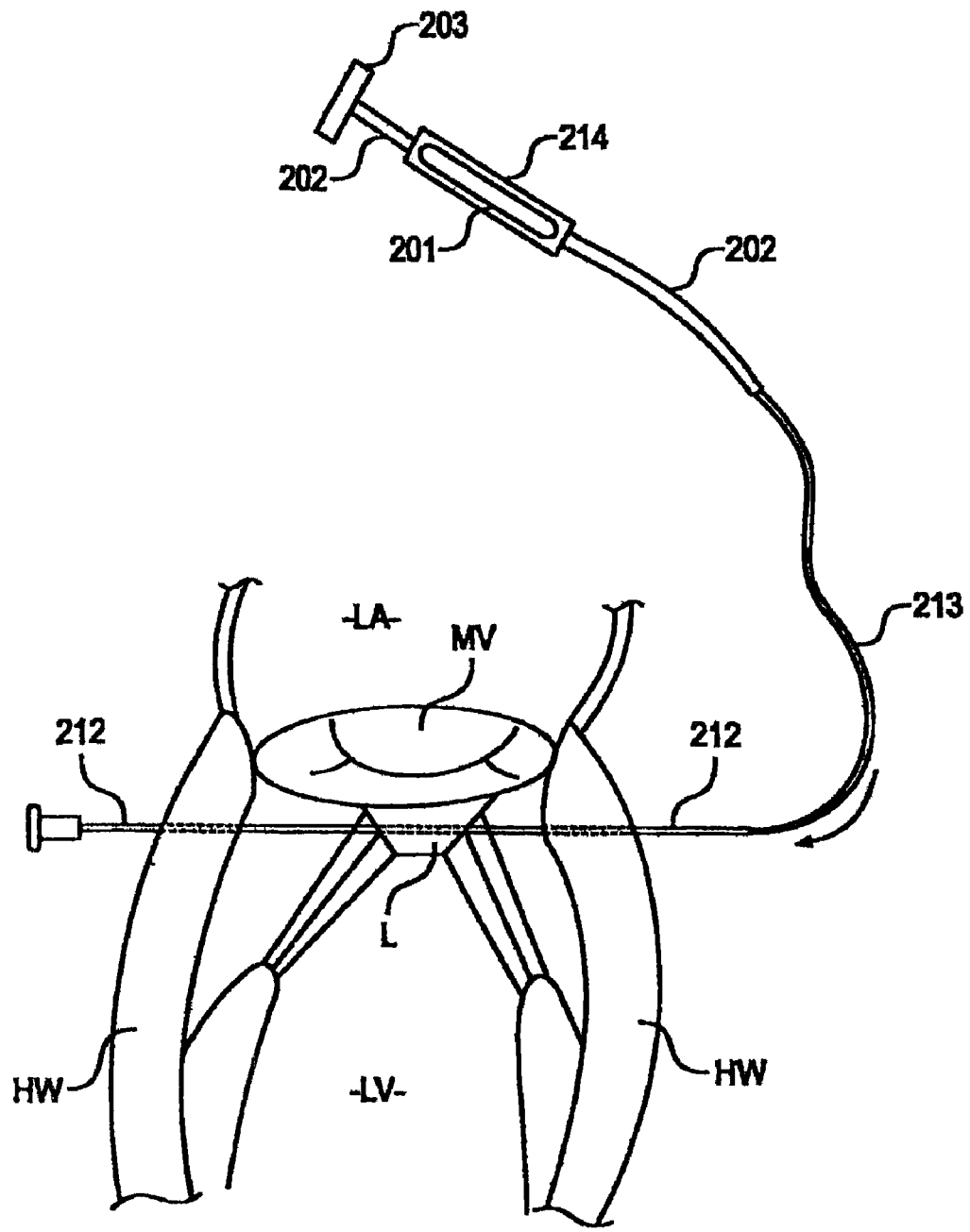
FIG. 14c is a partial perspective view of the left ventricle and left atrium with a leader assembly and sheath retaining a plug device being advanced through the needle of FIG. 14a according to an aspect of the invention.

An example of an approach for delivery of the plug device of FIG. 12 is illustrated in FIGS. 14*a*-14*c*. For exemplary purposes, the position of the plug device resulting from the delivery shown in FIGS. 14*a*-14*c* corresponds to position B, as shown in FIGS. 13*a* and 13*c*. However, other positions for the plug device could be obtained using the delivery approach which will now be described. Moreover, plug devices other than that of FIG. 12 could be implanted via the delivery techniques to be described.

In FIG. 14*a*, a needle and stylet assembly 210 is passed through the left ventricle LV between the mitral valve leaflets L. The stylet 211 is then removed, as shown by the arrow in FIG. 14*a*, leaving only the hollow needle 212 in place. The position of the needle 212 between the leaflets L is represented by the label X in FIG. 14*b*. The plug device may then be delivered through the needle 212. Or, as shown in FIG. 14*c*, a leader assembly 213 may be attached to the elongate member 202 from which the plug member 201 is suspended. The plug member 201 may have a folded configuration or may be a collapsible and expandable member. A sheath 214 may retain the plug member 201 during delivery across the heart chamber. An anchor pad 203 may be attached to the proximal end of the elongate member 202 during delivery. The anchor pad may optionally be either fixed at a predetermined position on the elongate member 202 or it may be movable with respect to the elongate member 202 so that its position is adjustable. The leader assembly 213 may be advanced through the heart wall at the side opposite to the side the needle 212 entered, and the needle 212 may then be removed from the heart. The leader assembly 213 and the elongate member 202 may then be advanced further until the plug member 201 is extracted from the sheath 214. This extraction causes the plug member 201 to unfold. Once the plug member 201 is fully extracted from the sheath 214 and appropriately positioned between the mitral valve leaflets, retaining sheath 214 may be removed from the heart and the leader assembly removed from the elongate member 202. A second anchor pad 203 may be placed on the distal end of the elongate member 202 to hold the plug device in place, as shown in FIG. 12.

Figure 14D:
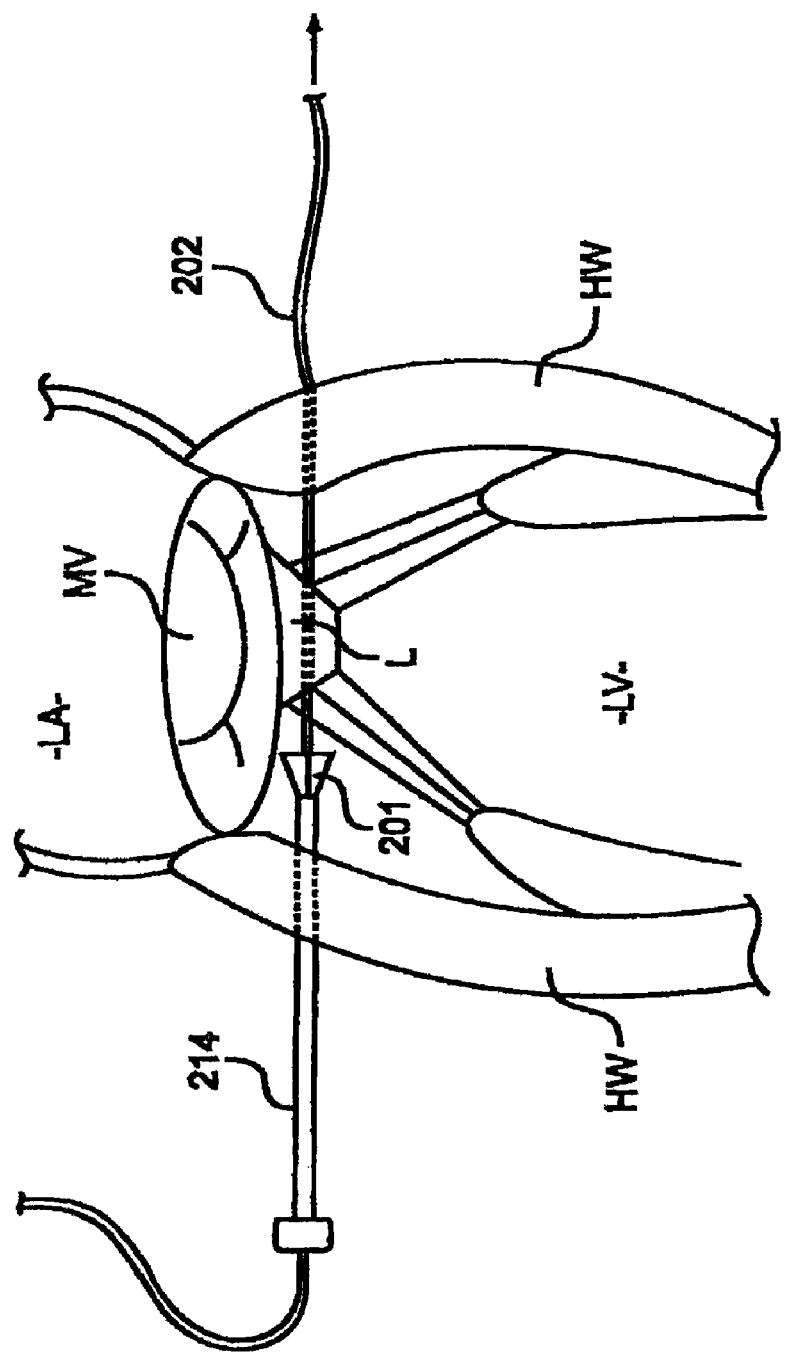
FIG. 14d is a partial perspective view of the left ventricle and left atrium showing an exemplary embodiment of a sheath retaining a plug device being advanced through the heart according to an aspect of the invention.

An exemplary embodiment for delivering a plug device using a retaining sheath is illustrated in FIG. 14*d*. Elongate member 202 may be connected to a leader member (not shown), which may be in the form of a sharpened needle, or the like. The leader member is configured to pass through the heart wall and across the ventricle. As shown in FIG. 14*d*, removal of the plug member 201 from the retaining sheath 214 may occur by advancing the sheath 214 partially through the heart wall HW and pulling the elongate member 202 extending through the heart wall HW opposite to the retaining sheath 214. As the elongate member 202 is pulled, the plug member 201 advances out of the distal end of the sheath 214. Once the plug member 201 advances entirely out of the distal end of the sheath 214, it will have an unfolded or expanded configuration and may be positioned as desired between the mitral valve leaflets L by pulling on the elongate member (in the direction of the arrow shown in FIG. 14d).

Figure 14E:
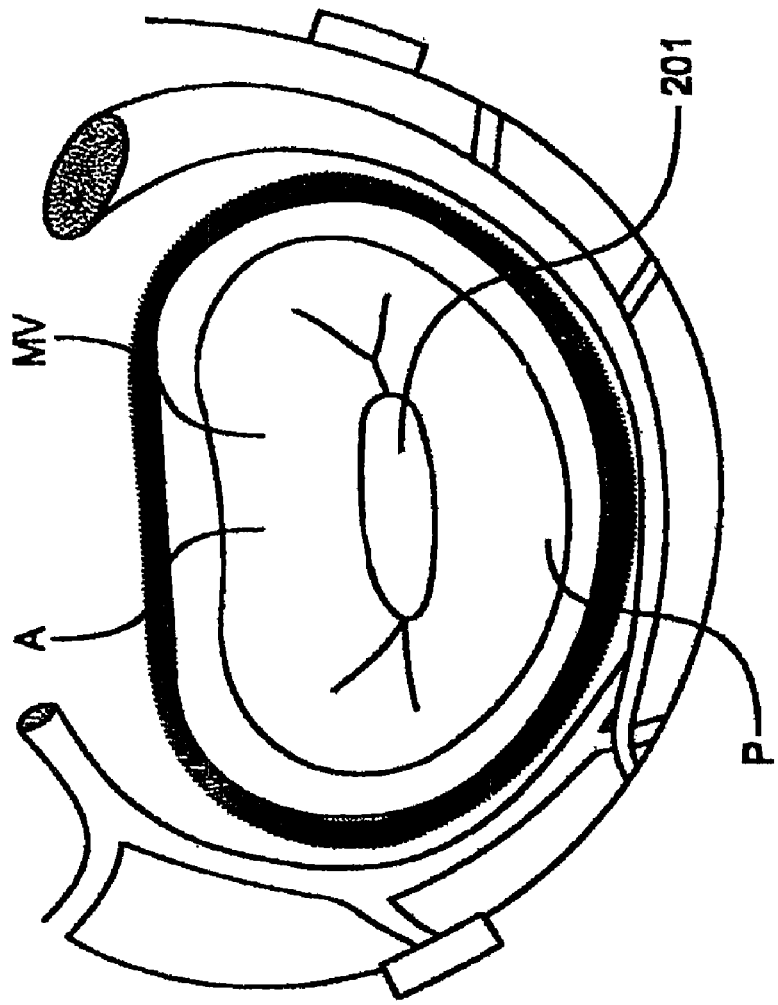
FIG. 14e is a partial short axis cross-sectional view of the heart during systole viewed from the top and showing an exemplary embodiment of a plug device implanted in the valve according to an aspect of the invention.
Figure 14F:
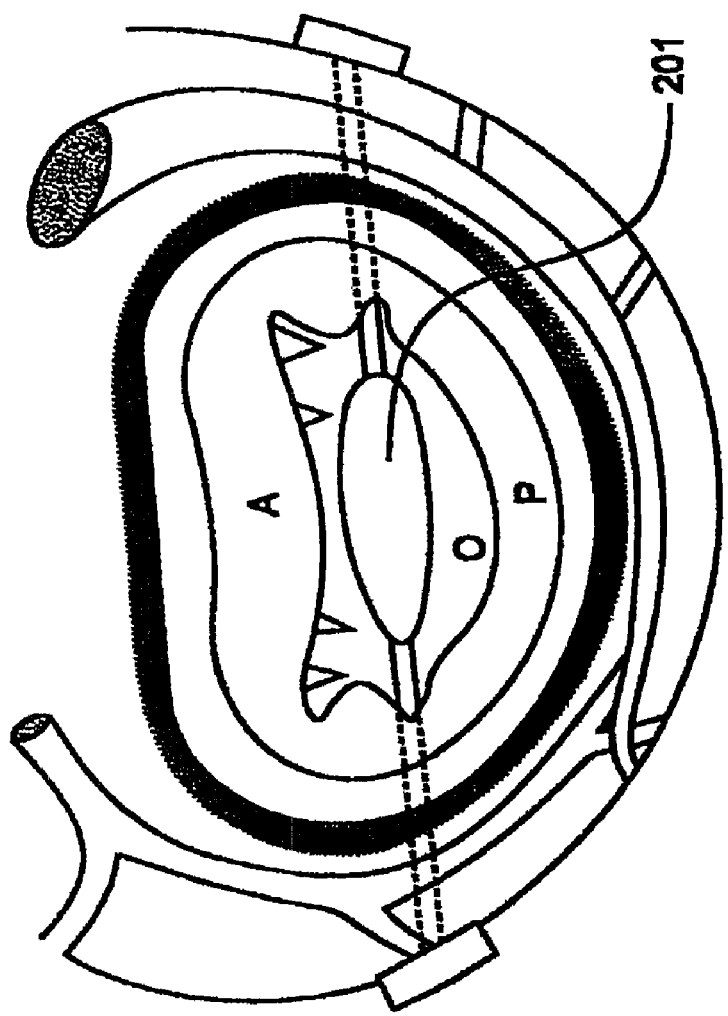
FIG. 14f is a partial short axis cross-sectional view of the heart during diastole viewed from the top and showing an exemplary embodiment of a plug device implanted in the valve according to an aspect of the invention.

FIG. 14e illustrates a top view of an implanted plug device, including plug member 201, during systole, according to an exemplary embodiment of the invention. The plug member 201 is disposed between the valve leaflets L and occupies the position of the valve opening O through which regurgitant flow would occur in the absence of valve treatment. FIG. 14f shows a top view of the implanted plug device during diastole, when the valve leaflets A, P are opened. As shown; flow through the valve O is permitted in the orifice space O between the leaflets A, P and the plug member 201.

Figure 15A:
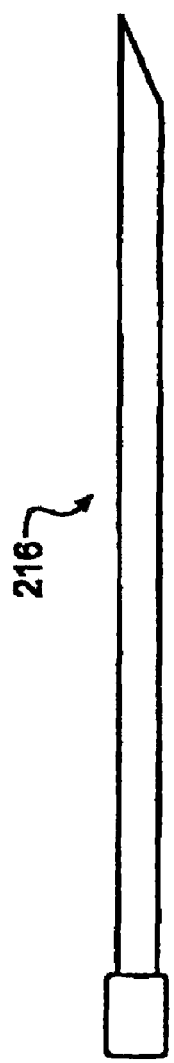
FIG. 15a is a perspective view of an exemplary embodiment of a trocar and needle assembly for delivery of a plug device according to an aspect of the invention.
Figure 15B:
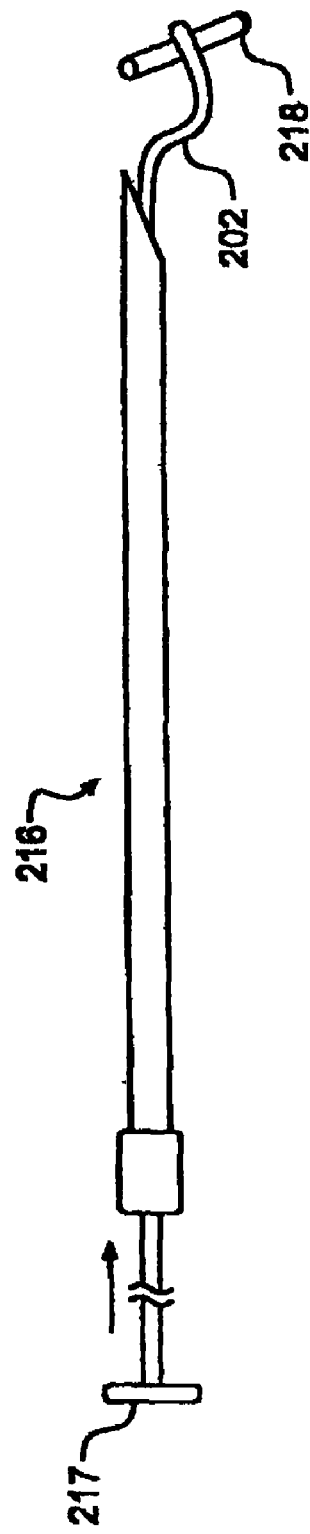
FIG. 15b is a perspective view of the trocar and needle assembly of FIG. 15a with an exemplary embodiment of a pusher assembly used to advance an anchor of a plug device out of the trocar and needle assembly according to an aspect of the invention.

FIGS. 15a-15c illustrate another delivery tool that may be used in lieu of those discussed with reference to FIGS. 14a-14d. In this embodiment, the elongate member 202, the folded plug member 201, and a deployable anchor member 218 may be retained in a tracer and needle assembly 216, as shown in FIG. 15a. The assembly 216 may be inserted across the heart such that it extends out of opposite heart walls and transverse the mitral valve in any of the positions discussed with reference to FIGS. 13a-13d, or other suitable, desired positions. A pusher mechanism 217 may then be inserted through the proximal end of the trocar and needle assembly 216 to advance the plug device 200 from the distal end of the assembly 216. As shown in FIG. 15b, an anchor 218 attached to an elongate member 202 exits the assembly 216 first. The anchor 218 is attached to the elongate member 202 so as to extend substantially perpendicularly to the elongate member 202. However, when placed in the assembly 216, the anchor 218 is turned with respect to the elongate member 202 such that it lies substantially parallel to the elongate member 202.

Once the anchor 218 has advanced out of the assembly 216, the pusher mechanism may be removed and the assembly 216 and plug device 200 may be retracted back through the heart in a direction opposite to the direction of advancement of the assembly 216 into the heart. As the plug device 200 is retracted with the assembly 216, the anchor 218 will catch on the external surface of the heart wall, preventing the plug device 200 from being pulled back through the heart with the assembly 216. The assembly 216 may continue to be retracted out of the heart and off of the plug device 200 until the plug member 201 eventually exits the distal end of the assembly 216, as shown in FIG. 15c. Upon exiting the assembly 216, the plug member 201 unfolds. The plug member 201 may then be positioned appropriately with respect to the mitral valve and, once the assembly 216 has been entirely removed from the plug device 200, an anchor (not shown) may be placed on the free end of the elongate member opposite to the anchor 218 to secure the plug device 200 in position.

Figure 16B:
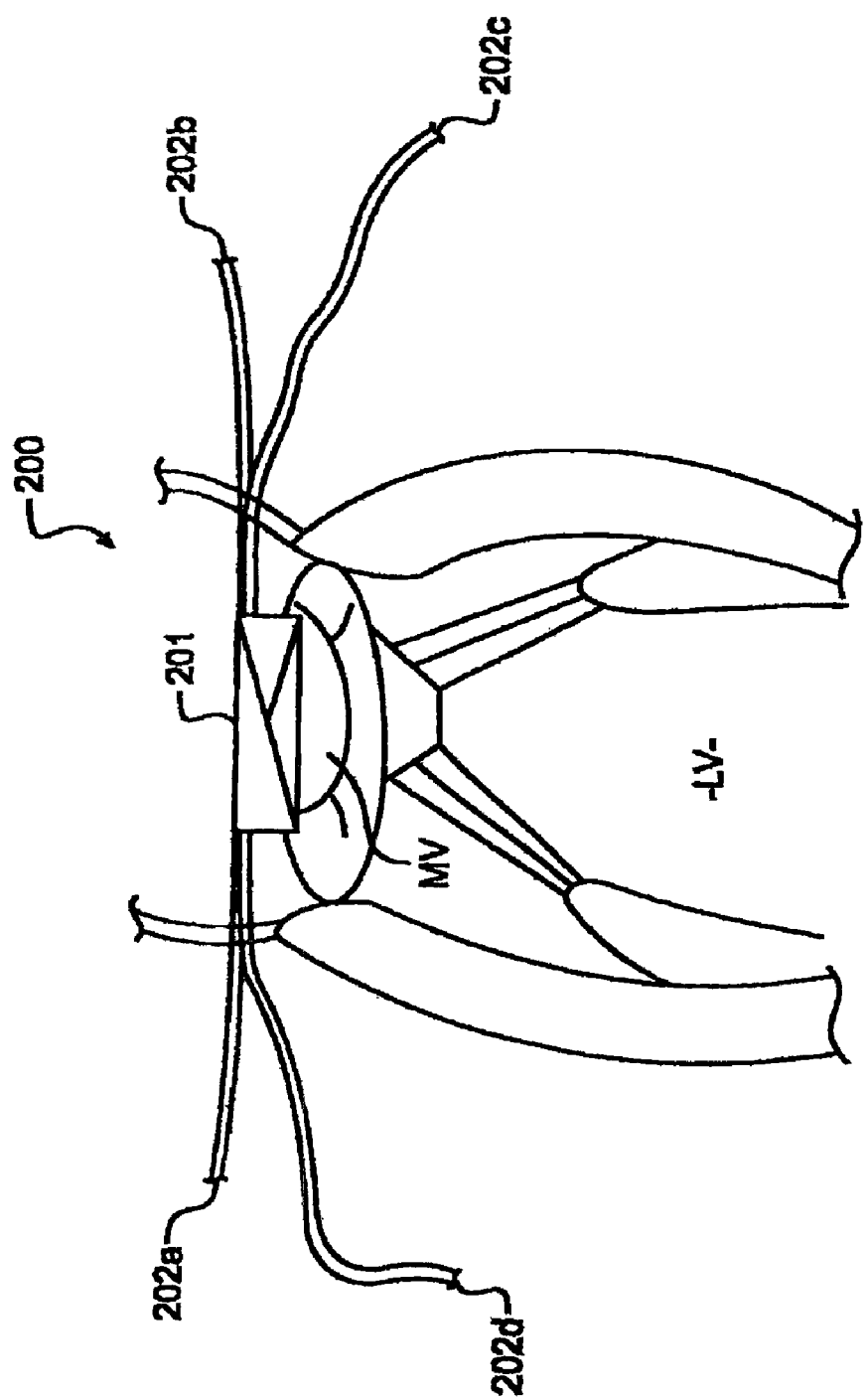
FIG. 16b is a partial perspective view of a left ventricle and left atrium with the plug device of FIG. 16a delivered to the heart in a folded configuration according to an aspect of the invention.

Yet another exemplary embodiment of a delivery technique for a folded plug member is illustrated in FIGS. 16a-16d. In this embodiment, the plug member 201 may have a folded configuration and be attached to a plurality of elongate members 202 (e.g., tethers) for suspending the plug member 201 in the mitral valve orifice between the leaflets, as described above. These elongate members 202 also assist in the unfolding of the plug member 201. FIG. 16a depicts the plug device 200 with the plug member 201 in a folded configuration and attached to four elongate members 202a-202d. The stylet and needle assembly, and the leader assembly described above with reference to FIGS. 14a-14c may be used to deliver the plug device 200 to the valve. In this manner, the elongate members 202a and 202d may be advanced together through the needle assembly, for example, in a supra-annular position, as shown in FIG. 16b. Once advanced, the elongate members 202a and 202d exit one side of the left atrial wall and the elongate members 202b and 202c exit the left atrial wall at an opposite side. The plug member 201, still in a folded configuration, is suspended slightly above the annular level of the mitral valve MV adjacent the valve orifice.

Figure 16C:
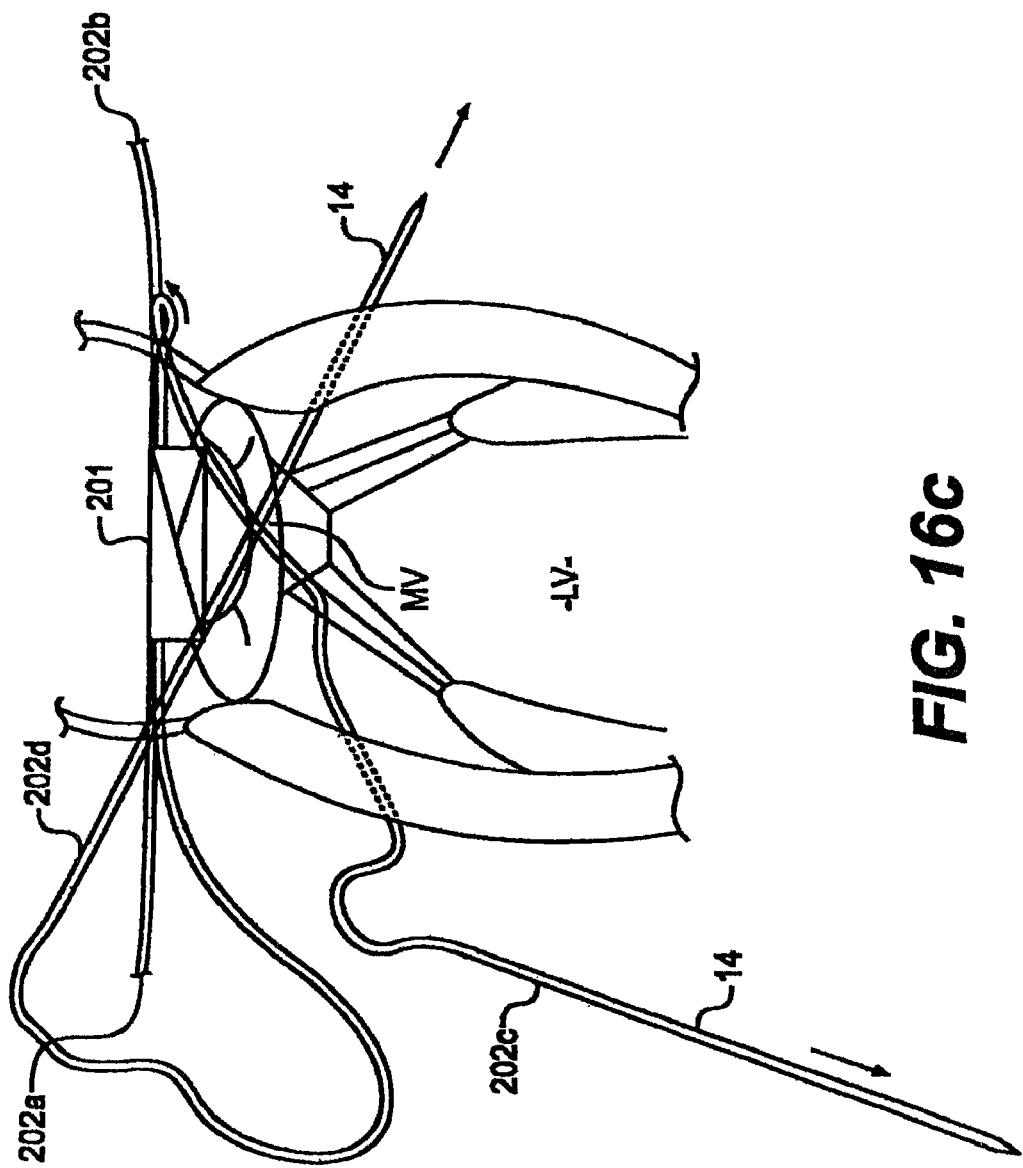
FIG. 16c is a partial perspective view of a left ventricle and left atrium showing an exemplary embodiment for unfolding the plug member of FIG. 16a according to an aspect of the invention.
Figure 16D:
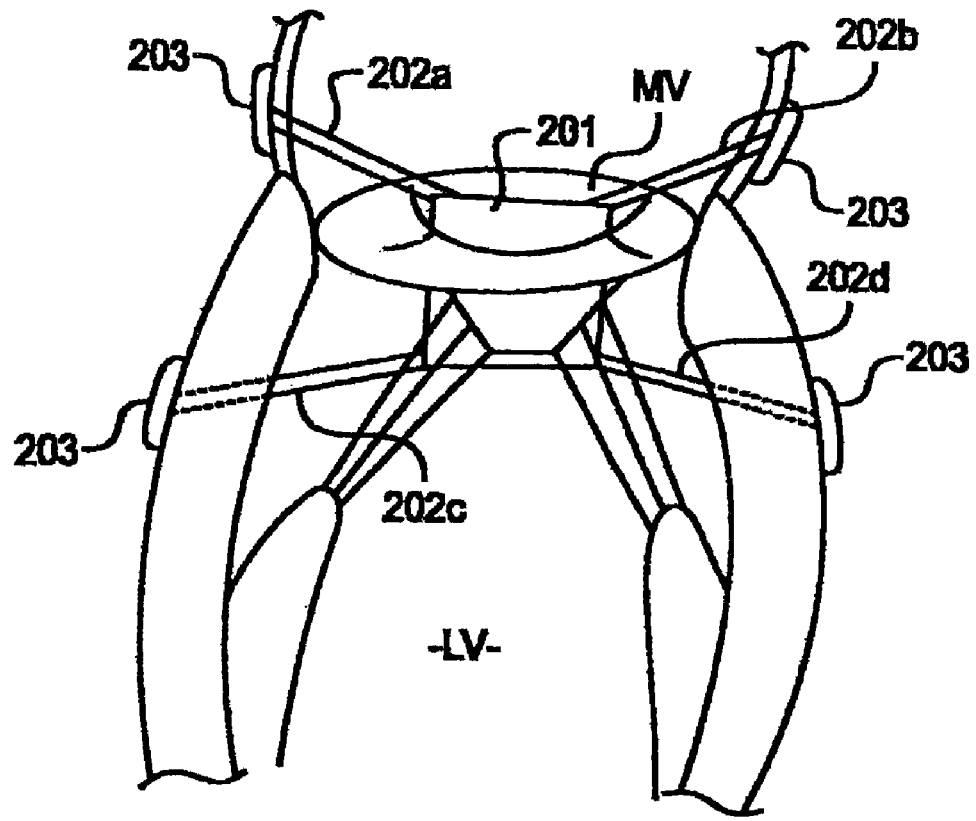
FIG. 16d is a partial perspective view of a left ventricle and left atrium showing the plug device of FIG. 16a implanted in the heart in an unfolded configuration according to an aspect of the invention.

To unfold the plug member 201, stylets 14 are attached to the free ends of the elongate members 202c and 202d. Using the needle stylets 14 to guide the free ends of the elongate members 202c, 202d, as shown in FIG. 16c, each member 202c, 202d is advanced back through the heart to an opposite side and to a sub-annular position, thus exiting through the left ventricular wall on a side opposite to its original exit through the left atrial wall. This action causes the plug member 201 to unfold and extend between the valve leaflets. The elongate members 202a-202d may then be secured with respect to the heart using external anchors 203, as shown in FIG. 16d. The plug device 200 in FIG. 16d thus has a supra-annular, sub-annular position.

Figure 19:
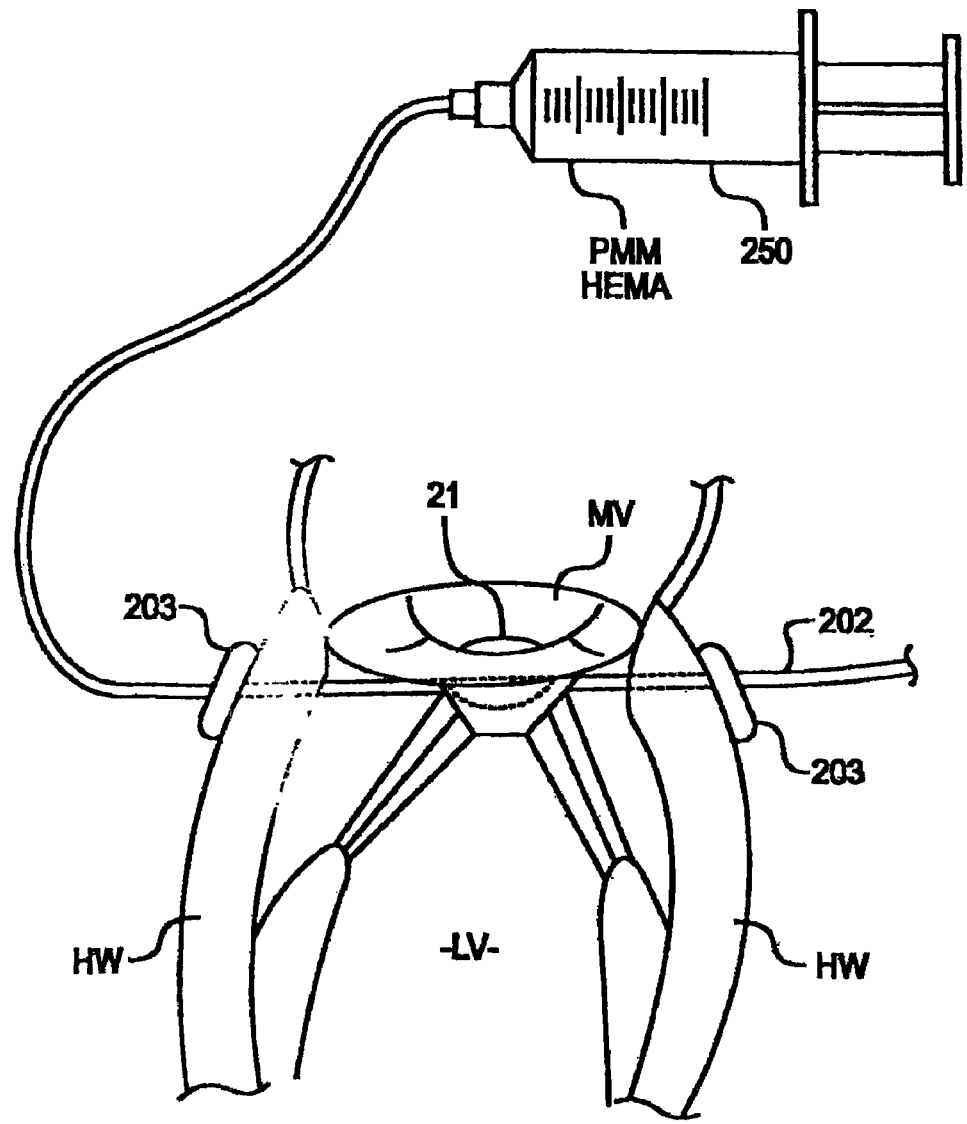
FIG. 19 is a long axis partial cross-sectional view of the heart showing an exemplary embodiment of an inflation device and a plug device having an inflatable plug member and anchors according to an aspect of the invention.

Other techniques for delivery and implantation of the plug devices of the invention are envisioned and are considered to be within the scope of the invention. For example, the plug member and at least one of the anchor members may be inflatable so that during delivery the members can be in a deflated configuration to facilitate passage through the heart wall or through a needle. As shown in FIG. 19, once the plug device 200 (i.e., at least one anchor and the plug member 202) is placed in the desired position relative to the mitral valve MV and heart wall HW, an inflator, which may optionally be in the form of a compressed air device or a needle 250 (as shown in FIG. 19) containing a fluid, such as PMMA (polymethylmethacrylate) P-HEMA (poly (2-hydroxyethyl methacrylate)), for example, may be connected to the elongate member and used to inflate the plug member 201 and the at least one anchor member 203. The elongate member in this case would be configured to allow passage of fluid therethrough to the plug member and at least one anchor member.

Figure 20:
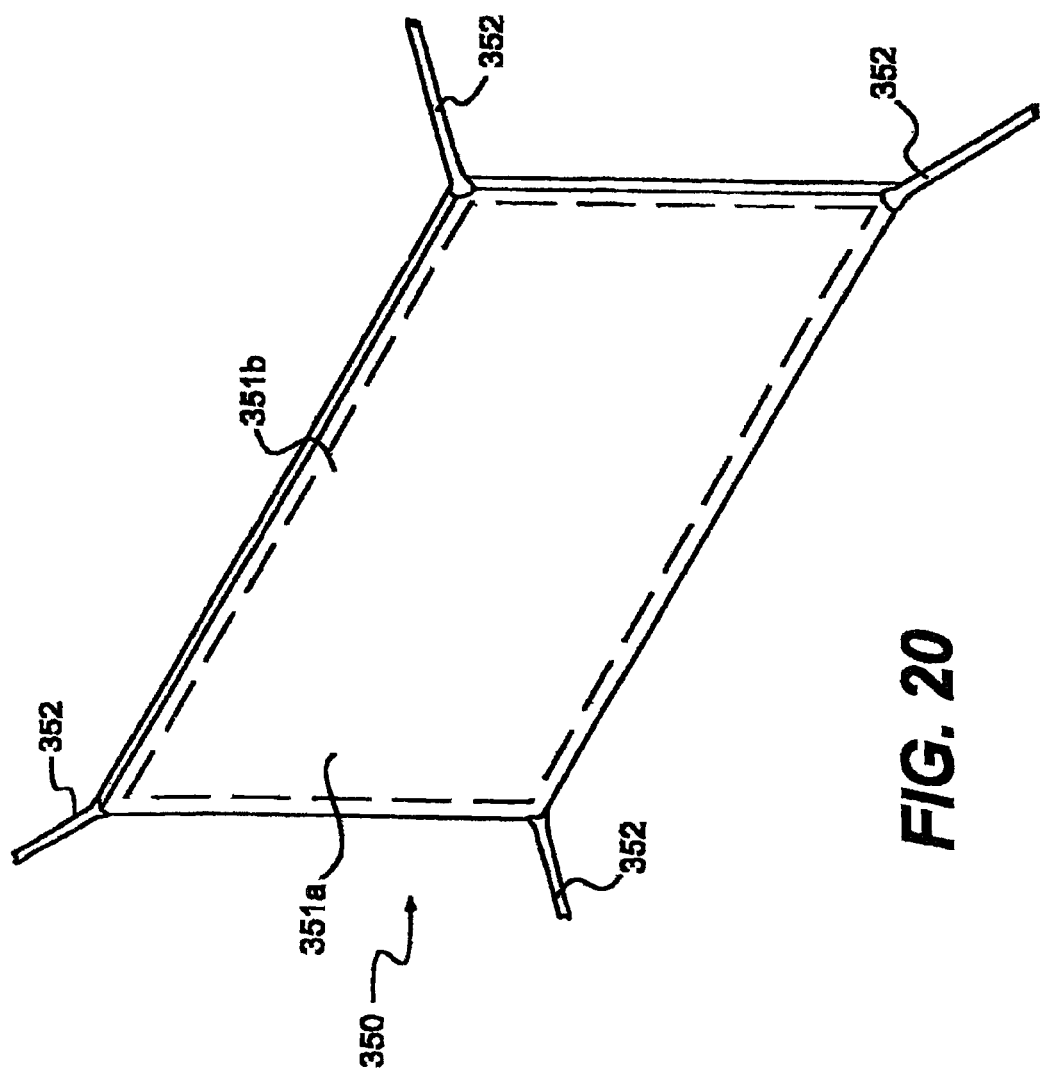
FIG. 20 is a perspective view of an exemplary embodiment of an inflatable plug device according to an aspect of the invention.

FIG. 20 illustrates an additional exemplary embodiment of an inflatable plug device 350. The plug device comprises plug member 351 made of two sheets 351a and 351b attached to each other along the edges. The plug device 350 also comprises tethers 352, for example, four tethers 352 attached to the plug member 351 proximate the corners of the sheets 351a, 351b. At least one of the tethers 352 may define a lumen configured for fluid flow therethrough. The lumen may be in flow communication with the plug member 351 so as to permit inflation of the plug member 351 via the lumen. In this manner, the plug member 351 may be filled to the desired shape and size as is needed to at least substantially prevent regurgitation through the valve.

Figure 17A:
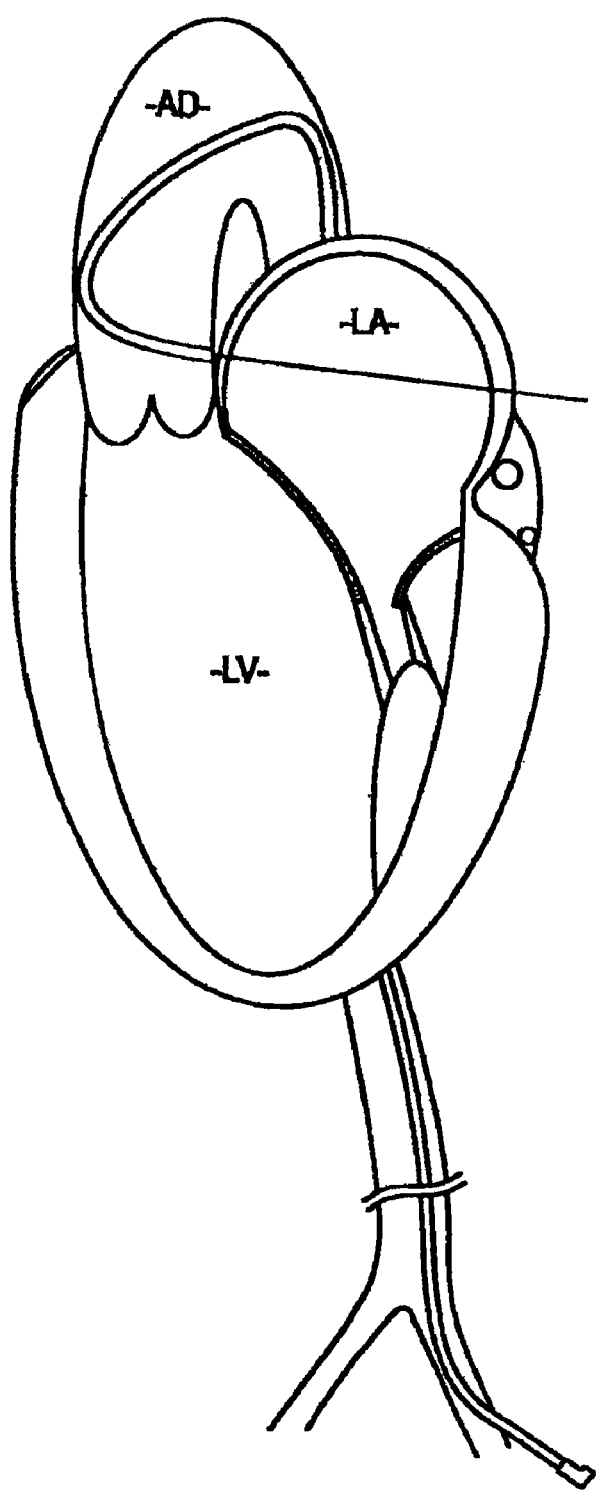
FIG. 17a is a cross-sectional view of the heart showing an exemplary embodiment of an endovascular delivery path for delivering a plug device according to an aspect of the invention.
Figure 17B:
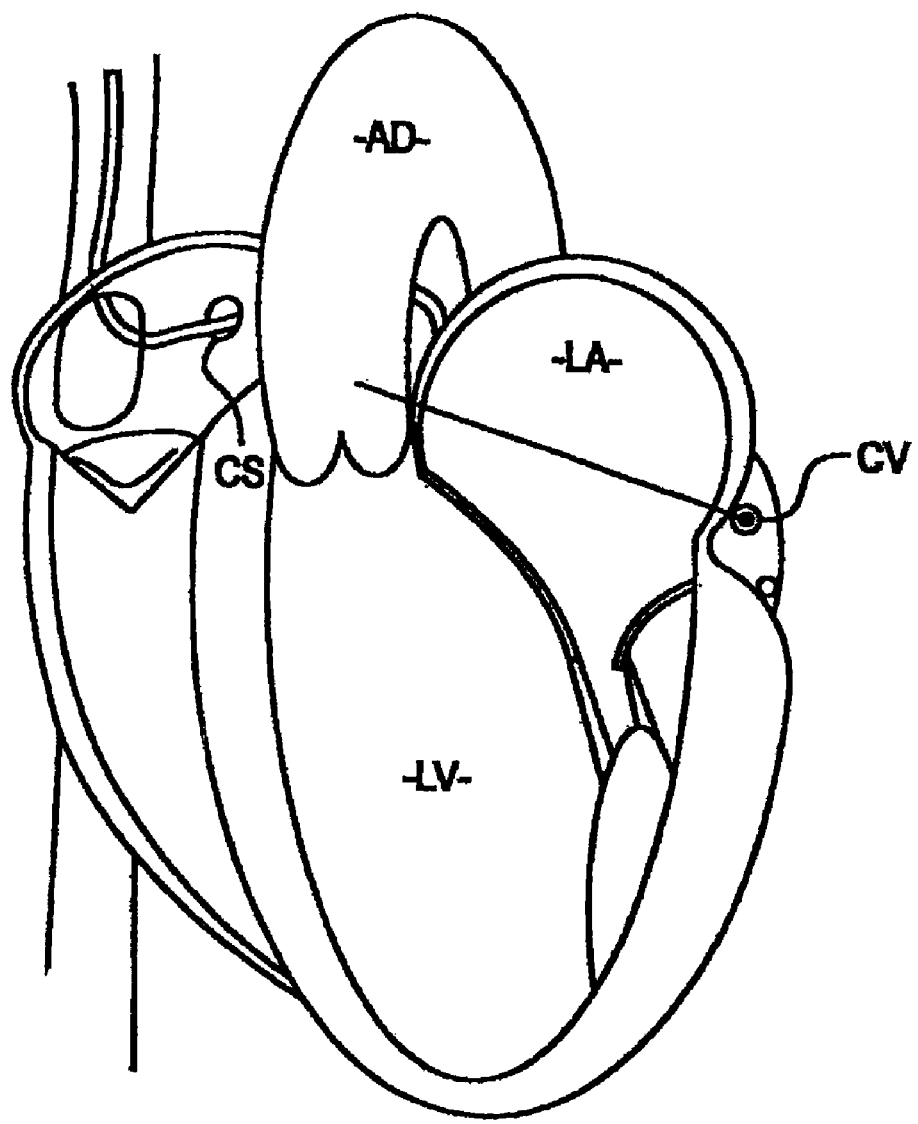
FIG. 17b is a cross-sectional view of the heart showing another exemplary embodiment of an endovascular delivery path for delivering a plug device according to an aspect of the invention.
Figure 17C:
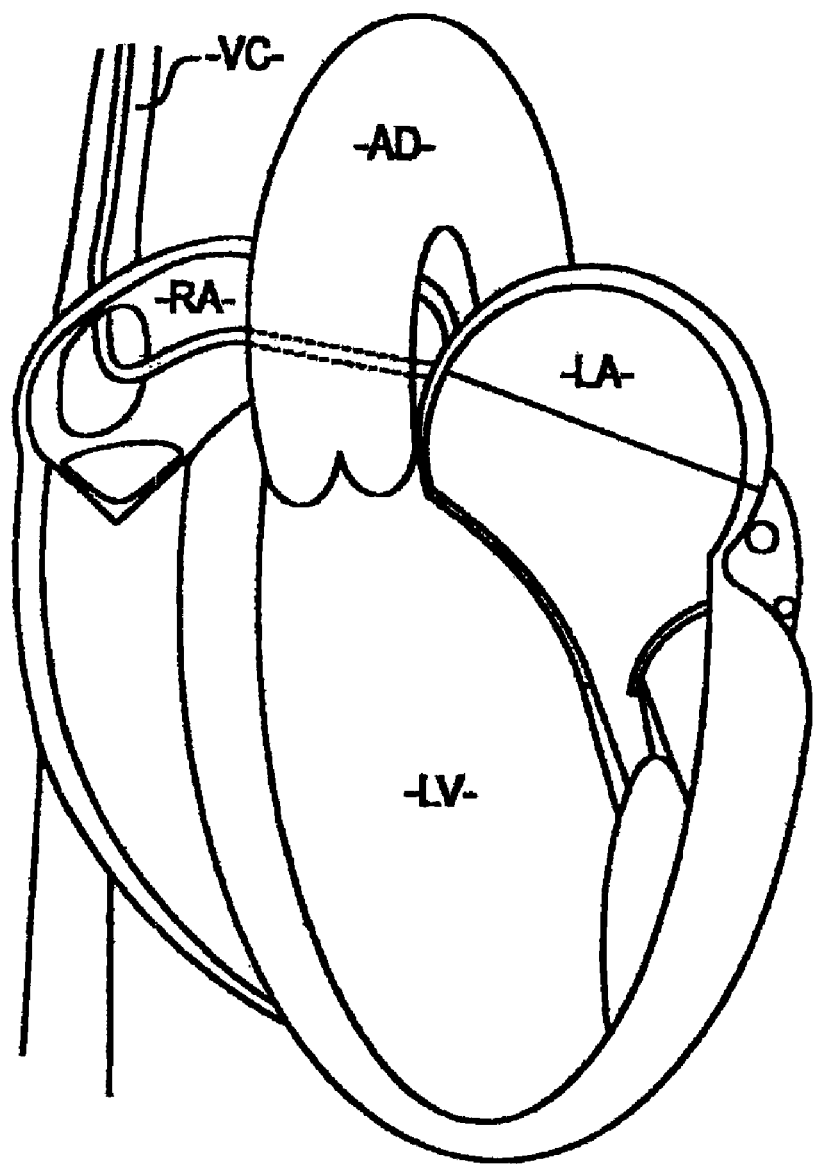
FIG. 17c is a cross-sectional view of the heart showing yet another exemplary embodiment of an endovascular delivery path for delivering a plug device according to an aspect of the invention.

Endovascular delivery techniques, including, for example, catheter-based delivery techniques, also are envisioned as within the scope of the invention. Such endovascular delivery techniques may be utilized in combination with the methods discussed with reference to FIGS. 14a-19. For example, the plug devices may be delivered through a catheter advanced through the lumen of the aorta AO and across the left atrial chamber LA, as shown in FIG. 17a. Alternatively, as shown in FIG. 17b, the delivery path may be through the lumen of the coronary sinus CS and the coronary vein CV, and from the coronary vein CV across the left atrial chamber LA. Yet another embodiment of an endovascular delivery path is shown in FIG. 17c. In this figure, the delivery path is through the lumen of the vena cava CV into the right atrial chamber RA and across the left atrial chamber LA.

The techniques for implanting the plug devices discussed above include extending elongate members, with the plug member suspended therefrom, substantially transversely from one wall of a heart chamber to an opposite wall of a heart chamber. In an alternative embodiment, shown in FIGS. 18a and 18*b*. The plug member may be suspended from an elongate member that engages only on one side of the heart. Such a configuration may alleviate the need to traverse the entire heart chamber, thereby minimizing risk of damaging internal cardiac structure.

Figure 18A:
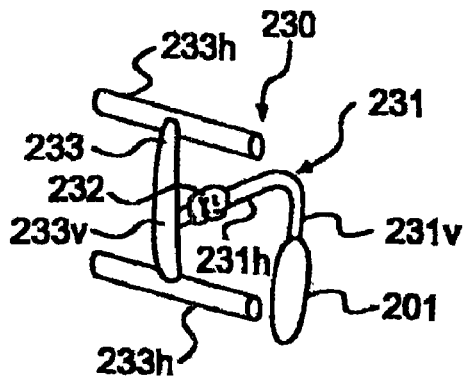
FIG. 18a is a perspective view of an exemplary embodiment of a plug device and anchoring frame according to an aspect of the invention.
Figure 18B:
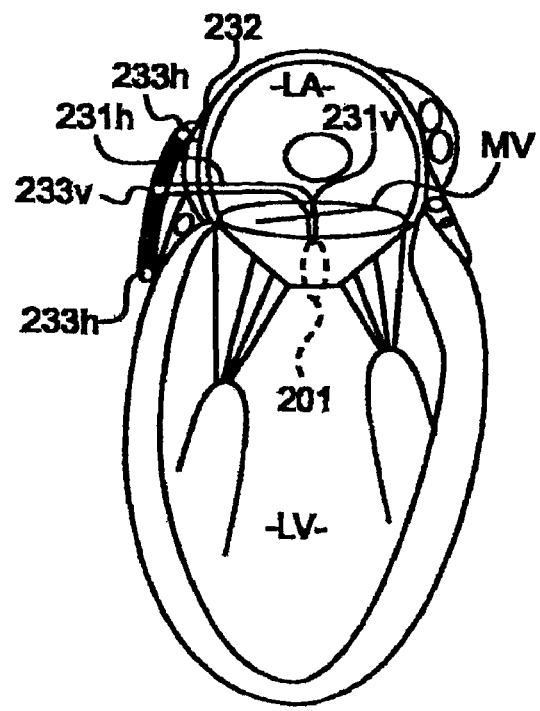
FIG. 18b is a long axis partial cross-sectional view of the heart showing an exemplary embodiment of the implantation of the plug device and anchoring frame of FIG. 18a according to an aspect of the invention.

FIG. 18*a* shows an exemplary embodiment of a plug device 230 and anchoring frame 233 for engaging only one side of the heart to implant the plug device 230. The plug member 201, shown as an ellipsoid plug member in this figure, depends from a beam member 231 having a horizontally extending portion 231*h* and a shorter, vertically extending portion 231*v*. The plug member 201 is connected to the vertically extending portion 231*v* so that the plug member 201 is placed within the valve orifice between the valve leaflets, as shown in FIG. 18*b*. Optionally, a intramuscular ingrowth sleeve 232, made of a Dacron velour, for example, may be placed around the horizontal portion 231*h*. The function of this sleeve 232 will be explained with reference to the discussion of the implantation of the device. The horizontal portion 231*h* connects to the anchoring frame 233 at an end opposite to the plug member 201. The anchoring frame 233 has a substantially I-shaped configuration and the horizontal portion 231*h* of the beam member 231 connects to the vertical leg 233*v* of the anchoring frame 233.

The horizontal legs 233*h* of the anchoring frame are placed on the external surfaces of the atrial wall and the ventricular wall, respectively, as shown in FIG. 18*b*. The vertical leg 233*v* is thus spaced from the heart wall. The horizontal legs 233*h* may be secured to the heart walls by suturing or other suitable, similar attachment mechanisms. The horizontal portion 231*h* of the beam member 231 extends from the vertical leg 233*v* and through the atrial wall so as to suspend the plug member 201 in the appropriate position relative to the mitral valve MV. The sleeve 232 is positioned on the horizontal portion 231*h*, and optionally may be slidable relative thereto, such that the heart wall surrounds the sleeve 232. The sleeve 232 therefore provides a surface that permits ingrowth of the heart wall muscle to assist in stabilizing the device relative to the heart. The ingrowth of the heart wall into the sleeve 232 also may prevent damage to the heart wall which would otherwise occur as a result of relative motion between the heart wall and the horizontal portion 231*h* caused by the heart's beating.

It will be apparent to those skilled in the art that various modifications and variations can be made in the devices and related methods for improving mitral valve function of the present invention and in construction of such devices without departing from the scope or spirit of the invention. As an example, a combination of devices depicted above may be used for achieving improved mitral valve function. Moreover, although reference has been made to treating the mitral valve and to the bloodflow patterns relating to the mitral valve, it is envisioned that other heart valves may be treated using the devices and methods of the present invention. Those having skill in the art would recognize how the devices and methods could be employed and/or modified to treat valves other than the mitral valve, taking into consideration factors such as the desired blood flow patterns through the valve. Other optional embodiments of the invention will be apparent to those skilled in the art from consideration of the specification and practice of the invention disclosed herein. The specification and examples are exemplary only, with a true scope and spirit of the invention being indicated by the following claims.

What is claimed is:

1. A method for treating a heart valve of a patient, comprising:

advancing a catheter having a lumen into a heart chamber, wherein a heart valve treatment device is disposed within the lumen of the catheter, the heart valve treatment device including:
  an elongate member having a first end;
  an anchoring mechanism secured to the first end of the elongate member; and
  a plug member;
disposing the heart valve treatment device proximate the heart valve;
securing the anchoring mechanism to heart tissue; and
positioning the plug member within an orifice of the heart valve so that leaflets of the heart valve contact the plug member during a portion of the cardiac cycle.

2. The method of claim 1, wherein the plug member is expandable.

3. The method of claim 1, wherein the elongate member has a second end, and the plug member is secured to the second end.

4. The method of claim 1, wherein the step of advancing a catheter having a lumen into a heart chamber includes advancing the catheter through a blood vessel, a right atrium, and a left atrium.

5. The method of claim 4, wherein the blood vessel is a vena cava, and the heart valve is a mitral valve.

6. The method of claim 1, wherein the heart tissue is a wall of a ventricle.

7. The method of claim 1, wherein the method does not include placing the patient on cardiopulmonary bypass.

8. A method for reducing regurgitation of a mitral valve of a patient, comprising:

endovascularly advancing a catheter having a lumen to an orifice of the mitral valve, wherein a plug device is disposed within the lumen of the catheter, the plug device including an expandable mitral valve plug and an elongate member;
disposing a portion of the elongate member within a left ventricle of the heart;
securing an end of the elongate member to heart tissue; and
positioning the expandable mitral valve plug within the orifice of the mitral valve so that leaflets of the mitral valve engage the mitral valve plug during a portion of the cardiac cycle, the expandable mitral valve plug being secured to the elongate member.

9. The method of claim 8, wherein endovascularly advancing a catheter having a lumen to an orifice of the mitral valve includes advancing the catheter through a blood vessel, a right atrium, and a left atrium.

10. The method of claim 9, wherein the blood vessel is a vena cava.

11. The method of claim 8, wherein the heart tissue includes a wall of the left ventricle.

12. The method of claim 8, wherein the portion of the cardiac cycle is systole.

13. The method of claim 8, wherein method does not include placing the patient on cardiopulmonary bypass.

14. The method of claim 8, wherein the step of securing an end of the elongate member to heart tissue includes attaching the end of the elongate member to an anchor.

15. A method for reducing regurgitation of a mitral valve of a patient's heart, comprising:

advancing a catheter including a mitral valve plug device through a patient's vena cava, a right atrium, and into a left atrium, the mitral valve plug device including an elongate member having a first end portion and a second end portion, the second end portion including a plug secured thereto;

securing the first end portion of the elongate member to a septal wall with an anchor pad;

disposing the second end portion of the elongate member proximate the mitral valve; and positioning the plug within an orifice of the mitral valve, such that leaflets of the mitral valve engage the plug during a portion of a cardiac cycle.

16. The method of claim 15, wherein the plug is expandable.

17. The method of claim 15, wherein the plug includes a coating.

18. The method of claim 17, wherein the coating includes an agent configured to promote endothelial growth.

19. The method of claim 16, wherein the plug is inflatable.

20. The method of claim 15, wherein the plug includes a first configuration when disposed within the catheter.

21. The method of claim 20, wherein the plug changes to a second configuration different from the first configuration when removed from the catheter.

22. The method of claim 15, wherein the plug includes an elongate configuration when positioned within the orifice of the mitral valve.

23. The method of claim 15, wherein the plug engages leaflets of the mitral valve only during the portion of the cardiac cycle.

24. The method of claim 23, wherein the portion of the cardiac cycle is systole.

* * * * *